(12) United States Patent
Bae et al.

(10) Patent No.: US 11,417,845 B2
(45) Date of Patent: Aug. 16, 2022

(54) ORGANIC COMPOUND, ORGANIC LIGHT-EMITTING DIODE AND ORGANIC LIGHT-EMITTING DEVICE CONTAINING THE COMPOUND

(71) Applicant: LG Display Co., Ltd., Seoul (KR)

(72) Inventors: Suk-Young Bae, Paju-si (KR); In-Ae Shin, Paju-si (KR); Jun-Yun Kim, Paju-si (KR)

(73) Assignee: LG Display Co., Ltd., Seoul (KR)

( * ) Notice: Subject to any disclaimer, the term of this patent is extended or adjusted under 35 U.S.C. 154(b) by 393 days.

(21) Appl. No.: 16/531,584

(22) Filed: Aug. 5, 2019

(65) Prior Publication Data

US 2020/0052222 A1 Feb. 13, 2020

(30) Foreign Application Priority Data

Aug. 7, 2018 (KR) .......................... 10-2018-0091754

(51) Int. Cl.
*H01L 51/00* (2006.01)
*C07D 233/58* (2006.01)
(Continued)

(52) U.S. Cl.
CPC ........ *H01L 51/0067* (2013.01); *C07D 209/88* (2013.01); *C07D 233/58* (2013.01); *C07D 277/22* (2013.01); *C09K 11/06* (2013.01); *H01L 51/0061* (2013.01); *H01L 51/0069* (2013.01); *C09K 2211/1018* (2013.01); *H01L 27/3244* (2013.01); *H01L 51/001* (2013.01); *H01L 51/0072* (2013.01); *H01L 51/5004* (2013.01); *H01L 51/504* (2013.01); *H01L 51/5012* (2013.01); *H01L 51/5056* (2013.01); *H01L 51/5072* (2013.01); *H01L 51/5088* (2013.01);
(Continued)

(58) Field of Classification Search
None
See application file for complete search history.

(56) References Cited

U.S. PATENT DOCUMENTS

2007/0292714 A1  12/2007  Funahashi
2019/0348616 A1  11/2019  Parham et al.

FOREIGN PATENT DOCUMENTS

KR         10-1429035 B1      8/2014
KR     10-2017-0120233 A      10/2017
(Continued)

OTHER PUBLICATIONS

Office Action issued in corresponding Taiwanese patent application No. 108127061 dated Apr. 15, 2020.
(Continued)

*Primary Examiner* — Jay Yang
(74) *Attorney, Agent, or Firm* — Morgan, Lewis & Bockius LLP

(57) ABSTRACT

An organic compound having a spiro-anthracene core and an aromatic or heteroaromatic group and/or an amino group bonded to the core, and an organic light-emitting diode and an organic light-emitting device including the organic compound are disclosed. Since the organic compound of the present disclosure has a rigid structure and a substantially narrow full width at half maximum (FWHM), it is possible to manufacture an organic light-emitting diode and an organic light-emitting device with lowered driving voltages and enhanced luminous efficiency and color purity using the organic compound.

29 Claims, 9 Drawing Sheets

(51) Int. Cl.
  *C09K 11/06* (2006.01)
  *C07D 277/22* (2006.01)
  *C07D 209/88* (2006.01)
  *H01L 27/32* (2006.01)
  *H01L 51/50* (2006.01)
  *H01L 51/56* (2006.01)
(52) U.S. Cl.
  CPC ...... *H01L 51/5092* (2013.01); *H01L 51/5096* (2013.01); *H01L 51/56* (2013.01); *H01L 2251/552* (2013.01); *H01L 2251/558* (2013.01)

(56) References Cited

FOREIGN PATENT DOCUMENTS

| TW | 200808683 A | 2/2008 |
|---|---|---|
| WO | 2018138039 A1 | 8/2018 |

OTHER PUBLICATIONS

European Search Report issued in corresponding European Application No. 19189379 dated Dec. 13, 2019.

ORGANIC COMPOUND, ORGANIC LIGHT-EMITTING DIODE AND ORGANIC LIGHT-EMITTING DEVICE CONTAINING THE COMPOUND

CROSS-REFERENCE TO RELATED APPLICATIONS

This application claims the priority benefit under 35 U.S.C. § 119(a) of Korean Patent Application No. 10-2018-0091754, filed in the Republic of Korea on Aug. 7, 2018, which is incorporated herein by reference in its entirety.

BACKGROUND

Technical Field

The present disclosure relates to an organic compound, and more specifically, to an organic compound enhancing luminous efficiency and color purity, an organic light-emitting diode and an organic light-emitting device including the compound.

Description of the Related Art

As display devices become larger, there exists a need for a flat display device with a lower spacing occupation. Among the flat display devices, a display device using an organic light-emitting diode (OLED) has come into the spotlight.

In the OLED, when electrical charges are injected into an emitting layer between an electron injection electrode (i.e., cathode) and a hole injection electrode (i.e., anode), electrical charges are combined to be paired, and then emit light as the combined electrical charges are disappeared.

The OLED can be formed even on a flexible transparent substrate such as a plastic substrate. In addition, the OLED can be driven at a lower voltage of 10 V or less. Moreover, the OLED has relatively lower power consumption for driving compared to the plasma display panels and inorganic electroluminescent devices, and color purity thereof is very high. Further, since the OLED can display various colors such as green, blue, red and the like, the OLED display device has attracted a lot of attention as a next-generation display device that can replace a liquid crystal display device (LCD).

The OLED may have a mono-layered emitting material layer between the anode and the cathode, Alternatively, the OLED may have a multiple-layered emitting layer that includes a hole injection layer (HIL), a hole transport layer (HTL), an emitting material layer (EML), an electron transport layer (ETL) and an electron injection layer (EIL) between the anode and the cathode so that the OLED can enhance luminous efficiency. The multiple-layered emitting layer may further include an exciton blocking layer such as an electron blocking layer (EBL) between the HTL and the EML and/or a hole blocking layer (HBL) between the EML and the ETL so as to prevent the excitons from disappearing.

The EML conventionally comprises a host and a dopant, and the actual emission is carried out at the dopant. Since material used as blue dopant must have a wider band energy gap compared to green and/or red dopant, there have been difficulties in developing blue dopant. US Patent Publication No. 2007/0292714 discloses blue luminous materials with a pyrene core and diphenyl amino substituent. However, the prior art luminous material had low luminous efficiency and short lifespan and showed low color purity and caused limitation in implementing full-color display.

BRIEF SUMMARY

Accordingly, the present disclosure is directed to an organic compound, an organic light-emitting diode and an organic light-emitting device including the organic compounds that substantially obviate one or more of the problems due to the limitations and disadvantages of the related art.

An object of the present disclosure is to provide an organic compound, an organic light-emitting diode and an organic light-emitting device that can enhance luminous efficiency and color purity.

Another object of the present disclosure is to provide an organic light-emitting diode and an organic light-emitting device that can lower driving voltage and power consumption, and can improve life span.

Additional features and advantages of the disclosure will be set forth in the description which follows, and in part will be apparent from the description, or may be learned by practice of the disclosure. The objectives and other advantages of the disclosure will be realized and attained by the structure particularly pointed out in the written description and claims herein as well as the appended drawings.

According to an aspect, the present disclosure provides an organic compound represented by the following Chemical Formula 1:

Chemical Formula 1

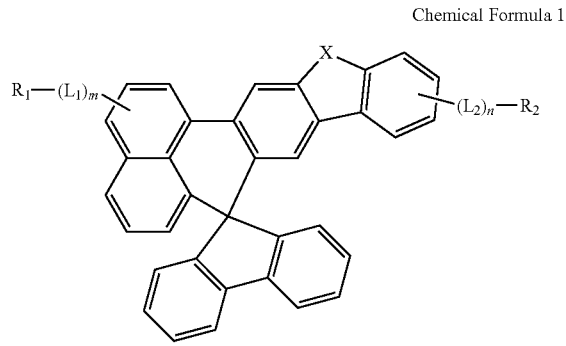

wherein each of $R_1$ and $R_2$ is independently selected from the group consisting of hydrogen, an amino group unsubstituted or substituted with a $C_4$-$C_{30}$ aromatic or heteroaromatic group, a $C_5$-$C_{30}$ aryl group unsubstituted or substituted with a $C_4$-$C_{30}$ aromatic or heteroaromatic group, a $C_4$-$C_{30}$ heteroaryl group unsubstituted or substituted with a $C_4$-$C_{30}$ aromatic or heteroaromatic group, a $C_5$-$C_{30}$ aralkyl group unsubstituted or substituted with a $C_4$-$C_{30}$ aromatic or heteroaromatic group, a $C_4$-$C_{30}$ heteroaralkyl group unsubstituted or substituted with a $C_4$-$C_{30}$ aromatic or heteroaromatic group, a $C_5$-$C_{30}$ aryloxyl group unsubstituted or substituted with a $C_4$-$C_{30}$ aromatic or heteroaromatic group and a $C_4$-$C_{30}$ heteroaryloxyl group unsubstituted or substituted with a $C_4$-$C_{30}$ aromatic or heteroaromatic group and at least one of $R_1$ and $R_2$ is not hydrogen, deuterium and tritium; each of $L_1$ and $L_2$ is independently selected from the group consisting of a $C_5$-$C_{30}$ arylene group unsubstituted or substituted with a $C_4$-$C_{30}$ aromatic or heteroaromatic group, a $C_4$-$C_{30}$ heteroarylene group unsubstituted or substituted with a $C_4$-$C_{30}$ aromatic or heteroaromatic group, a $C_5$-$C_{30}$ aralkylene group unsubstituted or substituted with a $C_4$-$C_{30}$ aromatic or heteroaromatic group, a $C_4$-$C_{30}$ heteroaralkylene group unsubstituted or substituted with a $C_4$-$C_{30}$ aromatic or heteroaromatic group, a $C_5$-$C_{30}$ aryloxylene group unsubstituted or substituted with a $C_4$-$C_{30}$ aromatic or heteroaromatic group and a $C_4$-$C_{30}$ heteroaryloxylene group unsubstituted or substituted with a $C_4$-$C_{30}$ aromatic or heteroaromatic group; each of m and n is independently 0 (zero) or 1; X is $CR_3R_4$, NRs, O or S, wherein each of $R_3$ to $R_5$ is independently selected from the group consisting of hydrogen, a linear or branched $C_1$-$C_{20}$ alkyl group, a $C_5$-$C_{30}$ aryl group unsubstituted or substituted with a $C_4$-$C_{30}$ aromatic or heteroaromatic group, a $C_4$-$C_{30}$ heteroaryl group unsubstituted or substituted with a $C_4$-$C_{30}$ aromatic or heteroaromatic group, a $C_5$-$C_{30}$ aralkyl group unsubstituted or substituted with a $C_4$-$C_{30}$ aromatic or heteroaromatic group, a $C_4$-$C_{30}$ heteroaralkyl group unsubstituted or substituted with a $C_4$-$C_{30}$ aromatic or heteroaromatic group, a $C_5$-$C_{30}$ aryloxyl group unsubstituted or substituted with a $C_4$-$C_{30}$ aromatic or heteroaromatic group, a $C_4$-$C_{30}$ heteroaryloxyl group unsubstituted or substituted with a $C_4$-$C_{30}$ aromatic or heteroaromatic group, a $C_5$-$C_{30}$ arylamino group unsubstituted or substituted with a $C_4$-$C_{30}$ aromatic or heteroaromatic group and a $C_4$-$C_{30}$ heteroarylamino group unsubstituted or substituted with a $C_4$-$C_{30}$ aromatic or heteroaromatic group.

According to another aspect, the present disclosure provides an organic light-emitting diode (OLED) that comprises a first electrode; a second electrode facing the first electrode; and a first emitting material layer between the first and second electrode, wherein the first emitting material layer comprises the above organic compound.

According to still another aspect, the present disclosure provides an organic light-emitting device that comprises a substrate and the OLED disposed over the substrate, as described above.

It is to be understood that both the foregoing general description and the following detailed description are examples and are intended to provide further explanation of the disclosure as claimed.

BRIEF DESCRIPTION OF THE SEVERAL VIEWS OF THE DRAWINGS

The accompanying drawings, which are included to provide a further understanding of the disclosure, illustrate implementations of the disclosure and together with the description serve to explain the principles of various embodiments of the disclosure.

DETAILED DESCRIPTION

Figure 1:
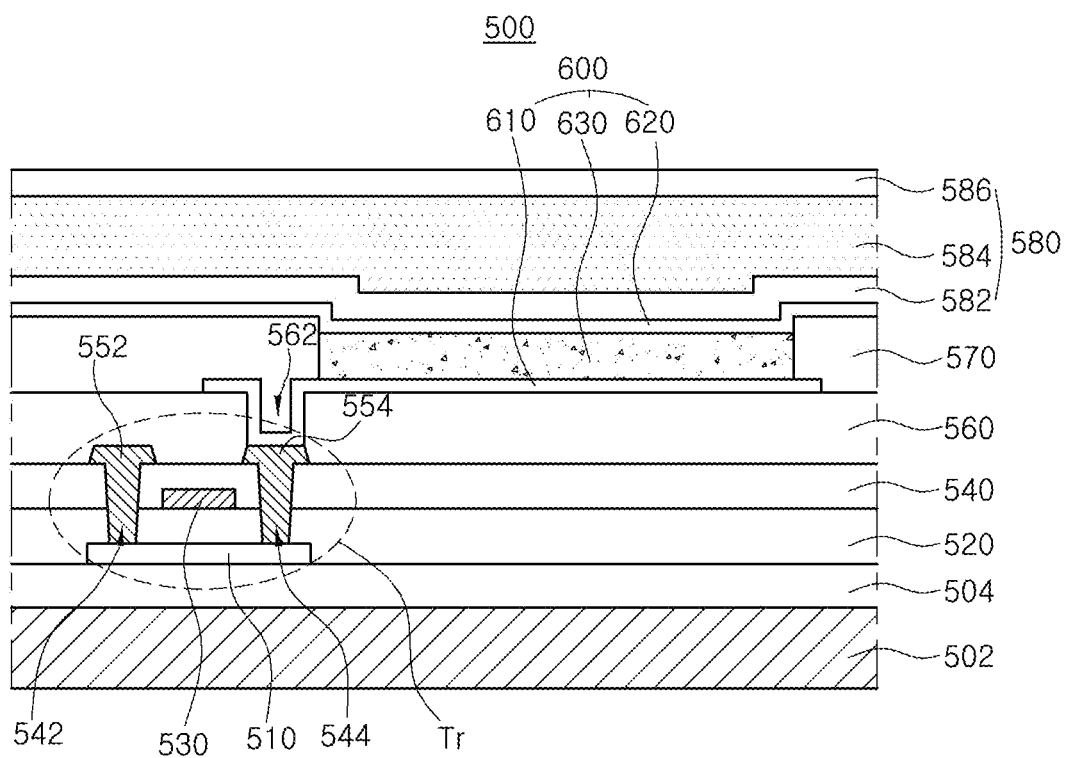
FIG. 1 is a schematic cross-sectional view illustrating an organic light-emitting display device of the present disclosure.

Reference will now be made in detail to aspects of the disclosure, examples of which are illustrated in the accompanying drawings.

Organic Compound

An organic light emitting diode (OLED) emits light as holes injected from the anode and electrons injected from the cathode are combined to form excitons in an EML and then unstable excited state excitons return to a stable ground state. The external quantum efficiency (EQE; $\eta_{ext}$) of the luminous material applied into the EML can be calculated by the following Equation (1):

$$\eta_{ext} = \eta_{S/T} \times \Gamma \times \Phi \times \eta_{out\text{-}coupling} \tag{1}$$

In Equation (1), "$\eta_{S/T}$" is an exciton generation efficiency (singlet/triplet ratio); "Γ" is a charge balance factor; "Φ" is a radiative quantum efficiency; "$\eta_{out\text{-}coupling}$" is out-coupling efficiency.

"$\eta_{S/T}$" is a transformation ratio from exciton to light and has maximum value of 0.25 in case of fluorescent materials. Theoretically, when electrons meet holes to form exciton, a singlet exciton of a paired spin and a triplet exciton of an unpaired spin are produced by a ratio of 1:3 by spin arrangements. Only the singlet exciton among the excitons can only be involved in emission process in case of the fluorescent materials.

Charge balance factor "Γ" is a balance between holes and electrons both of which form excitons and generally has a value of "1" assuming 1:1 matching of 100%. "Φ" is a value related with luminous efficiency of actual luminous materials and depends upon photoluminescence of dopant in a host-dopant system.

"$\eta_{out\text{-}coupling}$" is a ratio of light extracted outwardly among the emitted light in a luminous materials. When isotropic luminous material is thermally deposited to form a thin film, each of luminous molecules does not have specific orientation, but exists with random states. The out-coupling efficiency in such random orientation is generally assumed to be "0.2". Accordingly, when combining 4 parameters of Equation (1) above, the OLED may exhibit 5% luminous efficiency by maximum in case of using the prior art fluorescent material.

In contrast, phosphorescent materials use different luminous mechanism of converting both singlet excitons and triplet exciton into light. The phosphorescent materials convert singlet excitons into triplet excitons through intersystem crossing (ISC). Therefore, it is possible to enhance luminous efficiency in case of applying the phosphorescent materials that use both the singlet excitons and the triplet excitons during the luminous process compared to the fluorescent materials.

In case of using metal complexes having a heavy metal such as Ir, Pt, and the like as the phosphorescent materials, it is possible to convert triplet state to singlet state through strong spin-orbital bonds by the heavy metal. However, the prior art blue phosphorescent materials do not have sufficient color purity for the display device and exhibit a very short luminous lifespan, and therefore have not been used in commercial display devices.

Accordingly, there is need to develop a luminous compound having enhancing luminous efficiency and color purity, and a light-emitting diode including the luminous compound. The organic compound according to the present disclosure has a spiro-anthracene core with a rigid chemical conformation, and at least one substituent bonded to the spiro-anthracene core. The organic compound according to the present disclosure may be represented by Chemical Formula 1 below:

Chemical Formula 1

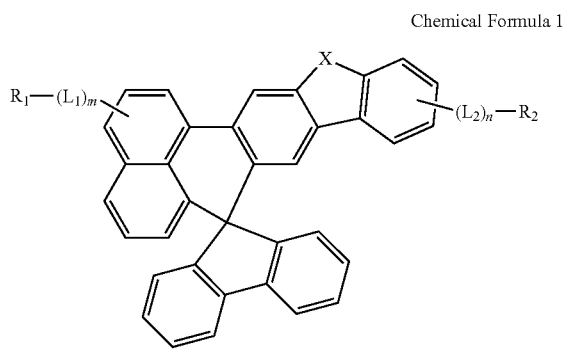

In Chemical Formula 1, each of $R_1$ and $R_2$ is independently selected from the group consisting of hydrogen, deuterium, tritium, an amino group unsubstituted or substituted with a $C_4$-$C_{30}$ aromatic or heteroaromatic group, a $C_5$-$C_{30}$ aryl group unsubstituted or substituted with a $C_4$-$C_{30}$ aromatic or heteroaromatic group, a $C_4$-$C_{30}$ heteroarylgroup unsubstituted or substituted with a $C_4$-$C_{30}$ aromatic or heteroaromatic group, a $C_5$-$C_{30}$ aralkyl group unsubstituted or substituted with a $C_4$-$C_{30}$ aromatic or heteroaromatic group, a $C_4$-$C_{30}$ heteroaralkyl group unsubstituted or substituted with a $C_4$-$C_{30}$ aromatic or heteroaromatic group, a $C_5$-$C_{30}$ aryloxyl group unsubstituted or substituted with a $C_4$-$C_{30}$ aromatic or heteroaromatic group and a $C_4$-$C_{30}$ heteroaryloxyl group unsubstituted or substituted with a $C_4$-$C_{30}$ aromatic or heteroaromatic group, and at least one of $R_1$ and $R_2$ is not hydrogen, deuterium and tritium, Each of $L_1$ and $L_2$ is independently selected from the group consisting of a $C_5$-$C_{30}$ arylene group unsubstituted or substituted with a $C_4$-$C_{30}$ aromatic or heteroaromatic group, a $C_4$-$C_{30}$ heteroarylene group unsubstituted or substituted with a $C_4$-$C_{30}$ aromatic or heteroaromatic group, a $C_5$-$C_{30}$ aralkylene group unsubstituted or substituted with a $C_4$-$C_{30}$ aromatic or heteroaromatic group, a $C_4$-$C_{30}$ heteroaralkylene group unsubstituted or substituted with a $C_4$-$C_{30}$ aromatic or heteroaromatic group, a $C_5$-$C_{30}$ aryloxylene group unsubstituted or substituted with a $C_4$-$C_{30}$ aromatic or heteroaromatic group and a $C_4$-$C_{30}$ heteroaryloxylene group unsubstituted or substituted with a $C_4$-$C_{30}$ aromatic or heteroaromatic group, and each of m and n is independently 0 (zero) or 1, and X is $CR_3R_4$, $NRs$, O or S. Each of $R_3$ to $R_5$ is independently selected from the group consisting of hydrogen, deuterium and tritium, a linear or branched $C_1$-$C_{20}$ alkyl group, a $C_5$-$C_{30}$ aryl group unsubstituted or substituted with a $C_4$-$C_{30}$ aromatic or heteroaromatic group, a $C_4$-$C_{30}$ heteroaryl group unsubstituted or substituted with a $C_4$-$C_{30}$ aromatic or heteroaromatic group, a $C_5$-$C_{30}$ aralkyl group unsubstituted or substituted with a $C_4$-$C_{30}$ aromatic or heteroaromatic group, a $C_4$-$C_{30}$ heteroaralkyl group unsubstituted or substituted with a $C_4$-$C_{30}$ aromatic or heteroaromatic group, a $C_5$-$C_{30}$ aryloxyl group unsubstituted or substituted with a $C_4$-$C_{30}$ aromatic or heteroaromatic group, a $C_4$-$C_{30}$ heteroaryloxyl group unsubstituted or substituted with a $C_4$-$C_{30}$ aromatic or heteroaromatic group, a $C_5$-$C_{30}$ arylamino group unsubstituted or substituted with a $C_4$-$C_{30}$ aromatic or heteroaromatic group and a $C_4$-$C_{30}$ heteroaryl amino group unsubstituted or substituted with a $C_4$-$C_{30}$ aromatic or heteroaromatic group.

As used herein, the term "unsubstituted" means that hydrogen atom is bonded, and in this case hydrogen atom comprises a protium, deuterium and tritium.

As used herein, the term "hetero" described n "heteroaromatic ring", "heteroaromatic group", "heteroalicyclic ring", "heterocyclic alkyl group", "heteroaryl group", "heteroaralkyl group", "heteroaryloxyl group", "heteroaryl amino group", "heteroarylene group", "heteroaralkylene group", "heteroaryloxylene group", and the like means that at least one carbon atoms, for example 1 to 5 carbon atoms, forming such aromatic or alicyclic rings are substituted with at least one hetero atom selected from the group consisting of N, O, S and combination thereof.

The $C_4$-$C_{30}$ aromatic or heteroaromatic group, which may be substituted with at least one of an amino group, a $C_5$-$C_{30}$ aryl group, a $C_4$-$C_{30}$ heteroaryl group, a $C_5$-$C_{30}$ aralkyl group, a $C_4$-$C_{30}$ heteroaralkyl group, a $C_5$-$C_{30}$ aryloxyl group, a $C_4$-$C_{30}$ heteroaryloxyl group, a $C_5$-$C_{30}$ arylene group, a $C_5$-$C_{30}$ arylamino group and a $C_4$-$C_{30}$ heteroaryl amino group, of $R_1$, $R_2$, $R_3$, $R_4$ and/or $R_5$, and/or at least one of a $C_5$-$C_{30}$ arylene group, a $C_4$-$C_{30}$ heteroarylene group, a $C_5$-$C_{30}$ aralkylene group, a $C_4$-$C_{30}$ heteroaralkylene group, a $C_5$-$C_{30}$ aryloxylene group and a $C_4$-$C_{30}$ heteroaryloxylene group of $L_1$ and/or $L_2$, may be unsubstituted or substituted with another at least one function groups. For example, the $C_4$-$C_{30}$ aromatic or heteroaromatic group may be substituted with, but is not limited to, a $C_1$-$C_{20}$ alkyl group unsubstituted or substituted with halogen atom(s), cyano group(s) and/or nitro group(s); a $C_1$-$C_{20}$ alkoxy group unsubstituted or substituted with cyano group(s) and/or nitro group(s); an alkyl halide group such as —$CF_3$; a hydroxyl group, a carboxyl group, a carbonyl group and an amino group, each of which is respectively unsubstituted or substituted with halogen atom(s), cyano group(s) and/or nitro group(s); an amino group substituted with a $C_1$-$C_{10}$ alkyl group; an amino group substituted with a $C_5$-$C_{30}$ aryl group and/or a $C_4$-$C_{30}$ heteroaryl group; a nitro group; a hydrazyl group; a sulfonyl group; a $C_1$-$C_{20}$ alkyl silyl group; a $C_1$-$C_{20}$ alkoxy silyl group; a $C_3$-$C_{30}$ cycloalkyl silyl group; a $C_5$-$C_{30}$ aryl silyl group; a $C_5$-$C_{30}$ aryl group; a $C_4$-$C_{30}$ heteroaryl group;

a $C_5$-$C_{30}$ aralkyl group; a $C_4$-$C_{30}$ heteroaralkyl group; a $C_5$-$C_{30}$ aryloxyl group; a $C_4$-$C_{30}$ heteroaryloxyl group; and the like.

The $C_4$-$C_{30}$ aromatic or heteroaromatic group may comprise, but is not limited to, a $C_5$-$C_{30}$ aryl group, a $C_4$-$C_{30}$ heteroaryl group, a $C_5$-$C_{30}$ aralkyl group, a $C_4$-$C_{30}$ heteroaralkyl group, a $C_5$-$C_{30}$ aryloxyl group, a $C_4$-$C_{30}$ heteroaryloxyl group, a $C_5$-$C_{30}$ arylamino group and/or a $C_4$-$C_{30}$ heteroaryl amino group.

For example, the $C_4$-$C_{30}$ aromatic or heteroaromatic group, which may form at least one of $R_1$ to $R_5$ of Chemical Formula 1 or be substituted with at least one of $R_1$ to $R_5$ of Chemical Formula 1, may independently comprise, but is not limited to, an unfused or fused aromatic group such as phenyl, biphenyl, terphenyl, tetraphenyl, naphthyl, anthracenyl, indenyl, phenalenyl, phenanthrenyl, azulenyl, pyreneyl, fluorenyl, tetracenyl, indacenyl or spiro fluorenyl, each of which may be unsubstituted or substituted, or an unfused or fused heteroaromatic group such as unsubstituted or substituted furanyl, thiophenyl, pyrrolyl, pyridyl, pyrimidyl, imidazolyl, pyrazolyl, oxazolyl, iso-oxazolyl, thiazolyl, iso-thiazoyl, pyridinyl, pyrimidinyl, pyrazinyl, pyridazinyl, triazinyl, tetrazinyl, indolyl, carbazolyl, benzothieno carbazolyl, quinolinyl, iso-quinolinyl, phthalazinly, quinoxalinyl, cinnolinyl, quinazolinyl or salinyl, each of which may be unsubstituted or substituted.

In this case, when the number of the aromatic or heteroaromatic rings forming respectively $R_1$ to $R_5$ in Chemical Formula 1 becomes larger, the entire organic compound may have a long conjugated structure such that its energy band gap may be significantly reduced. For Example, each of $R_1$ to $R_5$ in Chemical Formula 1 may have 1 to 4 aromatic rings, preferably 1 or 2 aromatic rings. Beside, each of $R_1$ to $R_5$ may be respectively 5-membered ring, 6-membered ring or 7-membered so that the organic compound may have narrow full width at half maximum (FWHM).

In an exemplary embodiment, $L_1$ and/$L_2$ as a linker in Chemical Formula 1 may be an unsubstituted or substituted aromatic linker. For example, in the case where $L_1$ and/or $L_2$ is an unsubstituted or substituted $C_5$-$C_{30}$ arylene group, each of $L_1$ and/or $L_2$ may be independently selected from the group, but is not limited to, phenylene, biphenylene, terphenylene, tetraphenylene, indenylene, naphthylene, azulenylene, indacenylene, acenaphthylene, florenylene, spiro-fluorenylene, anthracenylene, fluoranthrenylene, triphenylene, pyrenylene, chrysenylene, naphtacenylene, picenylene, perylenylene, pentaphenylene and hexacenylene, each of which is respectively unsubstituted or substituted with a $C_4$-$C_{30}$ aromatic or heteroaromatic group.

In an alternative embodiment, in the case where $L_1$ and/or $L_2$ is an unsubstituted or substituted $C_4$-$C_{30}$ heteroarylene group, each of $L_1$ and/or $L_2$ may be independently selected from the group, but is not limited to, pyrrolylene, imidazolylene, pyrazolylene, pyridinylene, pyrazinlylene, pyrimidinylene, pyridazinlylene, indolylene, iso-indolylene, indazolyelen, purinylene, quinolinylene, iso-quinolinylene, benzo-quinolinylene, phthalazinylene, naphthyridinylene, quinoxalinylene, quinazolinylene, benzo-iso-quinolinylene, benzo-quinazolinylene, benzo-quinoxalinylene, cinnlinylene, phenathridinylene, acridinylene, phenanthrolinylene, phenazinylene, benzoxazolylene, benaimidazolylene, furanylene, benzo-furanylene, dibenzo-furanylene, thiophenylene, benzo-thiophenylene, thiazolylene, iso-thiazolylene, benzo-thiazolylene, oxazolylene, iso-oxazolylene, triazolylene, tetrazolylene, oxadiazolylene, triazinylene, benzofuro-dibezno-furanylene, benzothieno-benzo-furanylene, benzothieno-dibenzo-furanylene, benzo-thiophenylene, dibenzo-thiophenylene, benzothieno-benzo-thiophenylene, benzothieno-dibenzo-thiophenylene, carbazolylene, bezno-carbazolylene, dibenzo-carbazolylene, indolo-carbazolylene, indeno-carbazolylene, benzofuro-carbazolylene, benzothieno-carbazolylene, imidazo-pyrimidinylene and imidazo-pyridinylne, each of which is respectively unsubstituted or substituted with a $C_4$-$C_{30}$ aromatic or heteroaromatic group.

In one exemplary embodiment, when the number of the aromatic or heteroaromatic rings forming respectively $L_1$ and/or $L_2$ becomes larger, the entire organic compound may have long conjugated structures such that its energy band gap may be significantly reduced. Preferably, the number of aromatic or heteroaromatic rings forming respectively $L_1$ and/or $L_2$ in Chemical Formula 1 may be 1 or 2, and more preferably one. In addition, each of $L_1$ and/or $L_2$ may be respectively a 5-membered ring, 6-membering ring or a 7-membered ring with regard to charge injection and/or transport, and preferably a 6-membered ring. For example, each of $L_1$ and/or $L_2$ may be independently, but is not limited to, unsubstituted or substituted phenylene, biphenylene, pyrrolylene, imidazolylene, pyrazolylene, pyridinylene, pyrazinlylene, pyrimidinylene, pyridazinlylene, furanylene or thiophenylene.

In an exemplary embodiment, each of $R_1$ and $R_2$ may be bonded to an -ortho position, a -metha position or a -para position, preferably a meta position or a para position of the spiro-anthracene core directly or via linker $L_1$ and $L_2$.

Since the organic compound represented by Chemical Formula 1 has a conformationally rigid spiro-anthracene core bonded by amino group and/or aromatic or heteroaromatic group, it can enhance its color purity. Particularly, it is possible to implement a light-emitting diode or device that lowers their driving voltage and enhance their luminous efficiency using the organic compound according to the present disclosure. For example, the organic compound according to the present disclosure may be used as dopant of emitting material layer of an organic light-emitting diode.

In one exemplary embodiment, the organic compound of the present disclosure may be an organic compound having a spiro-anthracene core and an aromatic or heteroaromatic group bonded (connected or combined) to the spiro-anthracene core. The aromatic or heteroaromatic group may be directly boned to the spiro-anthracene core or bonded to the spiro-anthracene core via an aromatic or heteroaromatic linker. Such an organic compound may have the following structure of Chemical Formula 2:

Chemical Formula 2

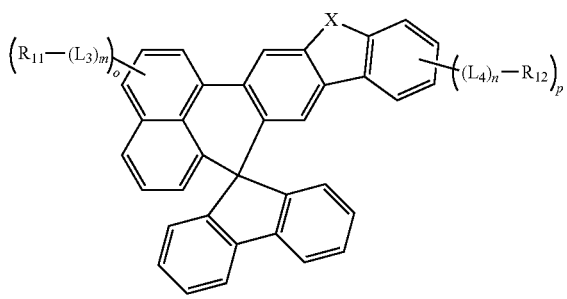

In Chemical Formula 2, each of $R_{11}$ and $R_{12}$ is independently selected from the group consisting of a $C_5$-$C_{30}$ aryl group unsubstituted or substituted with a $C_4$-$C_{30}$ aromatic or heteroaromatic group and a $C_4$-$C_{30}$ heteroaryl group unsubstituted or substituted with a $C_4$-$C_{30}$ aromatic or heteroaromatic group, Each of $L_3$ and $L_4$ is independently selected from the group consisting of a $C_5$-$C_{30}$ arylene group unsubstituted or substituted with a $C_4$-$C_{30}$ aromatic or heteroaromatic group and a $C_4$-$C_{30}$ heteroarylene group unsubstituted or substituted with a $C_4$-$C_{30}$ aromatic or heteroaromatic group. Each of o and p is independently 0 (zero) or 1, and at least one of o and p is 1. Each of m, n and X is identical as defined in Chemical Formula 1.

In an exemplary embodiment, each of the aryl group and the heteroaryl group of $R_{11}$ and/or $R_{12}$ in Chemical Formula 2 may respectively comprise the aryl group and the heteroaryl group as explained in Chemical Formula 1, and each of the arylene group and the heteroarylene group of $L_3$ and/or $L_4$ in Chemical Formula 2 may respectively comprise the arylene group and the heteroarylene group as explained in Chemical Formula 1. In addition, one of o and p in Chemical Formula 2 may be, but is not limited to, 0 (zero). In an exemplary embodiment, each of $R_{11}$ and $R_{12}$ may be bonded to an -ortho position, a -meta position or a -para position, preferably a meta position or a para position on the outer six-membered ring in the spiro-anthracene core directly or via linker $L_3$ or $L_4$.

In alternatively exemplary embodiment, the organic compound of the present disclosure may be an organic compound having a spiro-anthracene core bonded by aromatic or heteroaromatic amino groups. Such an organic compound may have the following structure of Chemical Formula 3:

Chemical Formula 3

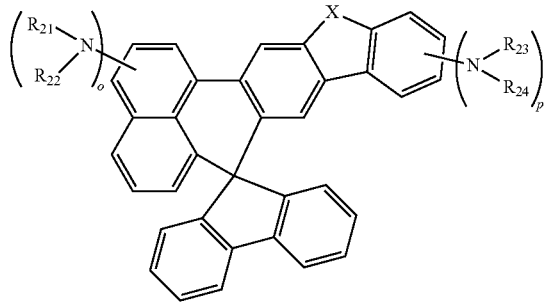

In Chemical Formula 3, each of $R_{21}$ to $R_{24}$ is independently selected from the group consisting of a $C_5$-$C_{30}$ aryl group unsubstituted or substituted with a $C_4$-$C_{30}$ aromatic or heteroaromatic group and a $C_4$-$C_{30}$ heteroaryl group unsubstituted or substituted with a $C_4$-$C_{30}$ aromatic or heteroaromatic group. Each of o and p is independently 0 (zero) or 1, and at least one of o and p is 1. X is identical as defined in Chemical Formula 1.

In an exemplary embodiment, each of the aryl group and the heteroaryl group of $R_{21}$ to $R_{24}$ in Chemical Formula 3 may respectively comprise the aryl group and the heteroaryl group as explained in Chemical Formula 1. Besides, one of o and p in Chemical Formula 3 may be, but is not limited to, 0 (zero). In an exemplary embodiment, each of the amino group substituted with aromatic or heteroaromatic group may be bonded to an -ortho position, a meta position or a para position, preferably meta position or para position of the spiro-anthracene core.

As an example, each of $R_{11}$ and $R_{12}$ in Chemical Formula 2 may comprise imidazolyl and thizaolyl each of which is unsubstituted or substituted with phenyl and each of $R_{21}$ to $R_{24}$ in Chemical Formula 3 may comprise phenyl. Particularly, the organic compound of the present disclosure may have one of the following structures of Chemical Formula 4:

Chemical Formula 4

Compound 1

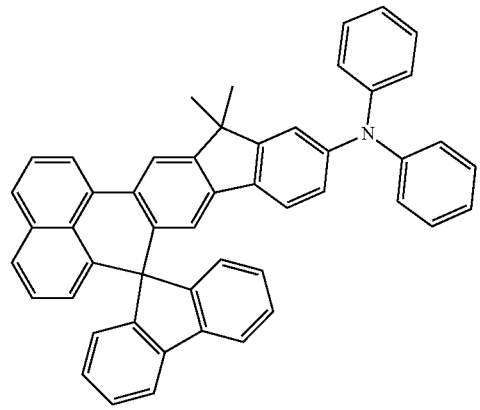

compound 2

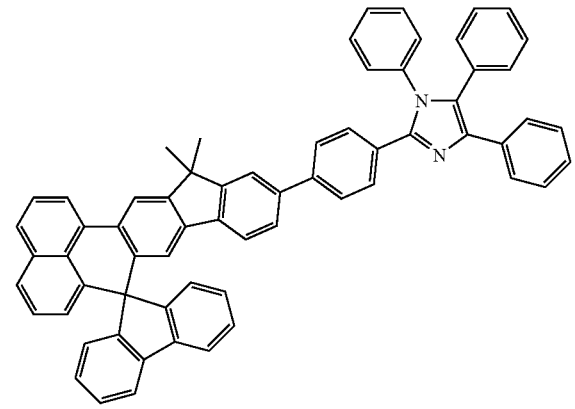

compound 3

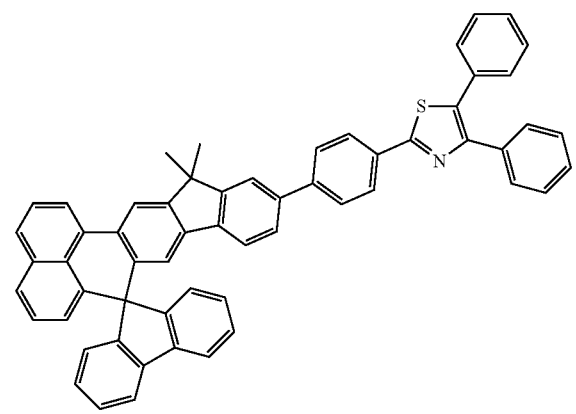

-continued
compound 4
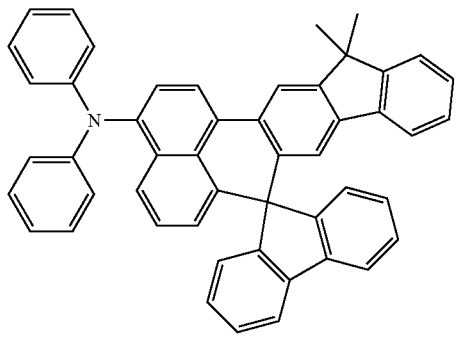
compound 5
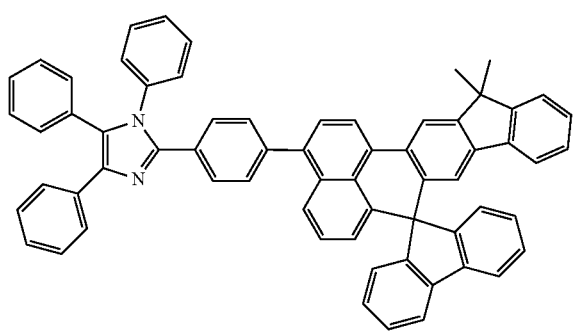
compound 6
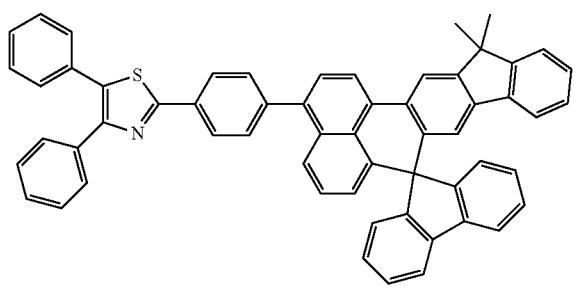
compound 7
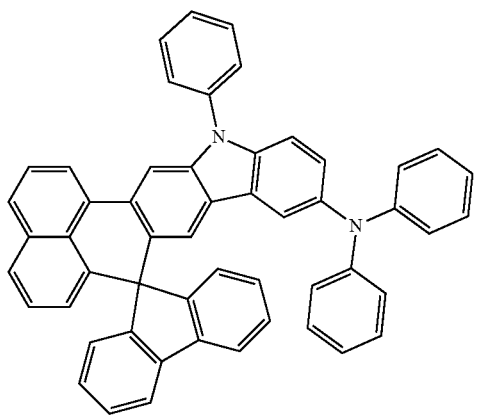
-continued
compound 8
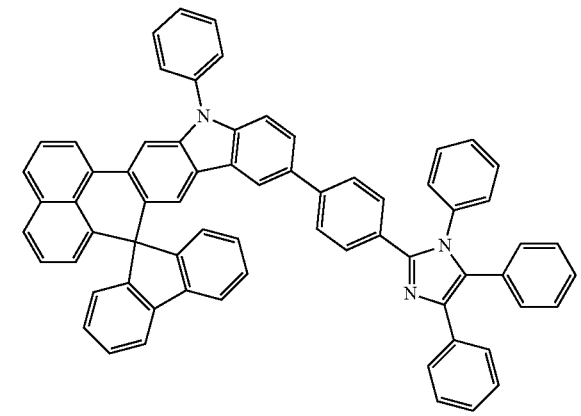
compound 9
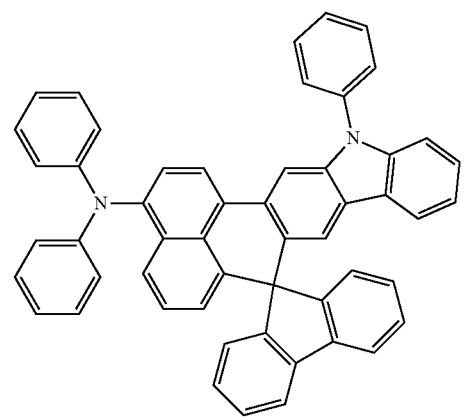
compound 10
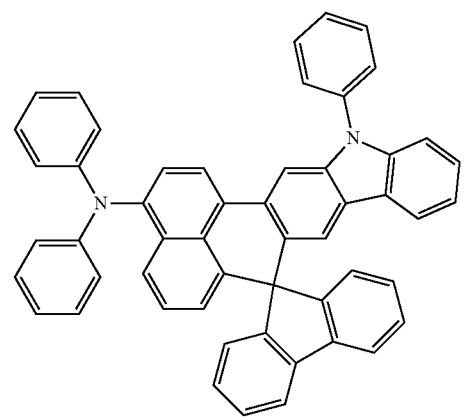

compound 11
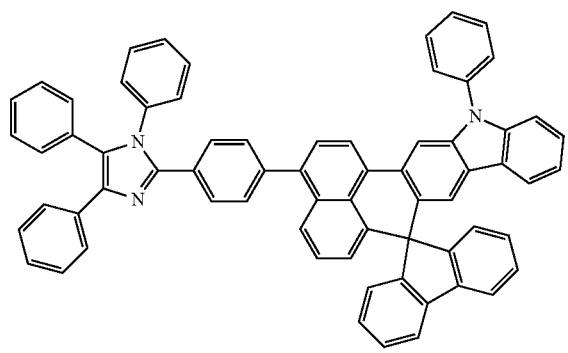
compound 12
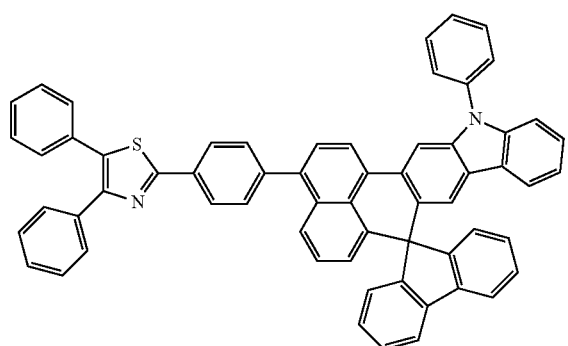
compound 13
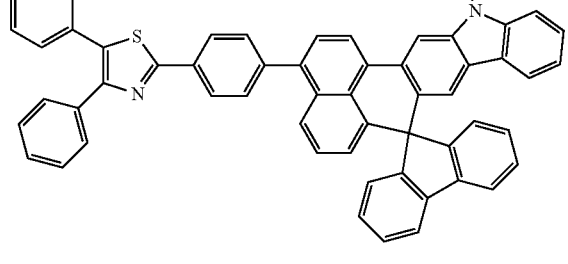
compound 14
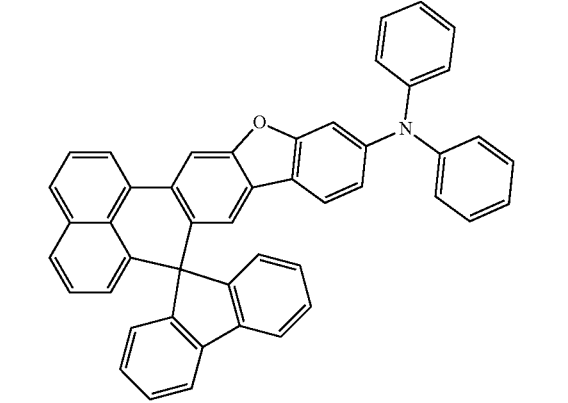
compound 15
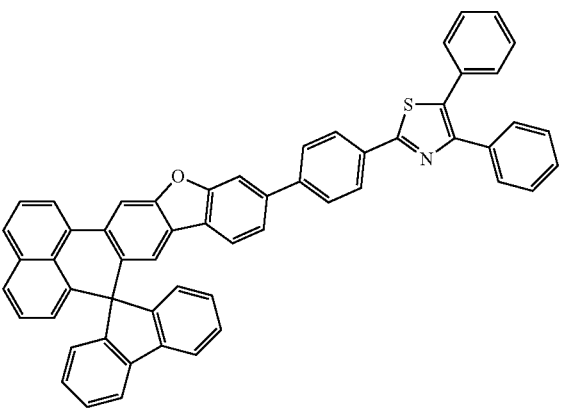
compound 16
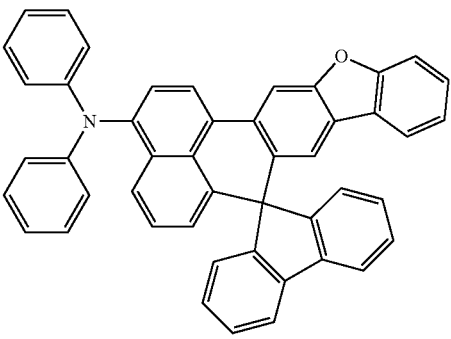
compound 17
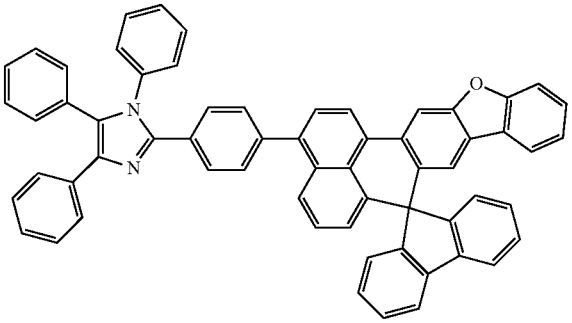
compound 18
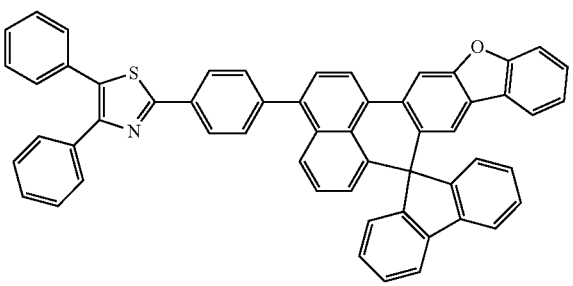

compound 19
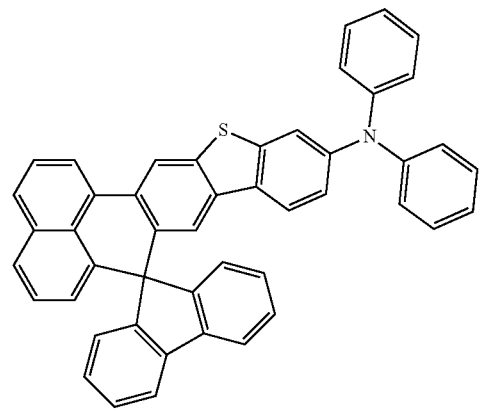
compound 20
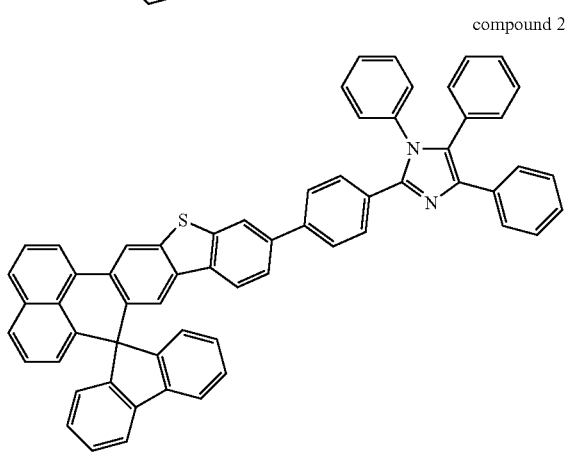
compound 21
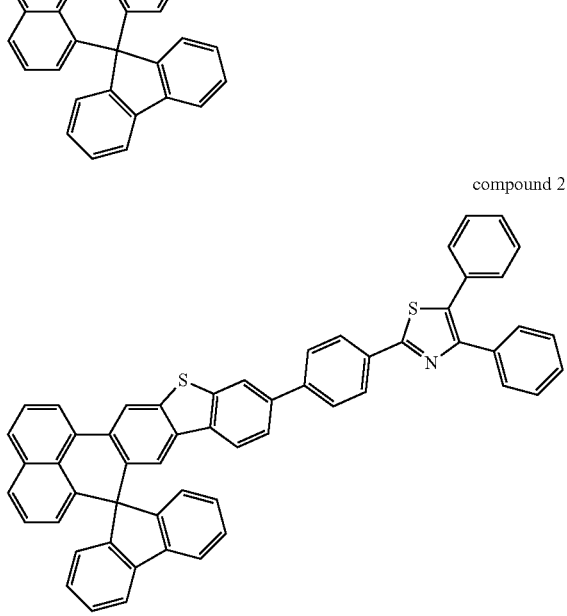
compound 22
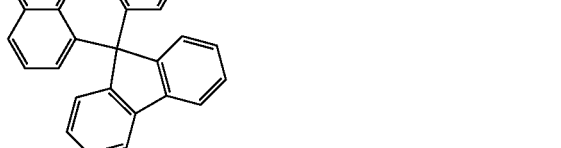
compound 23
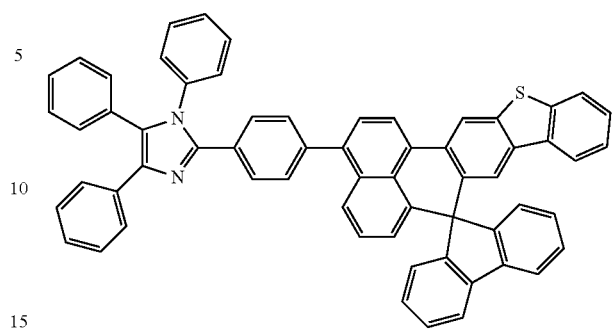
compound 24
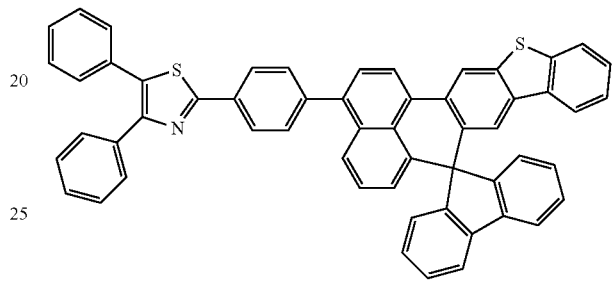
compound 25
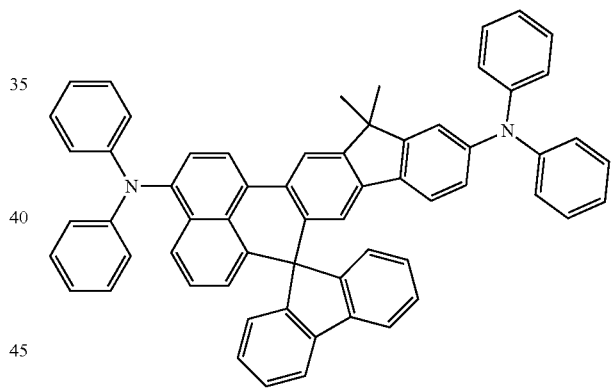
compound 26
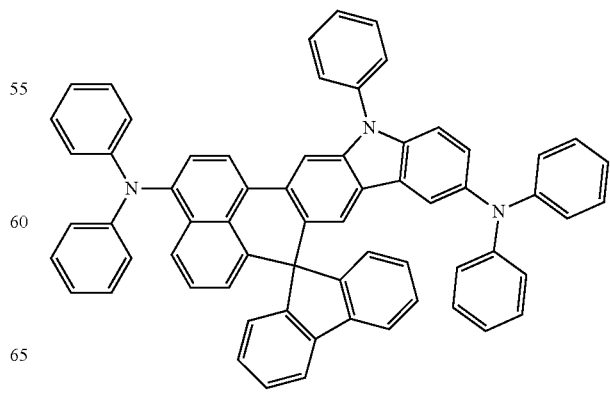

compound 27
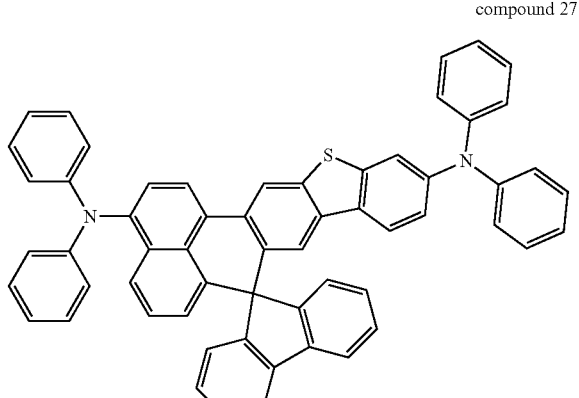
compound 28
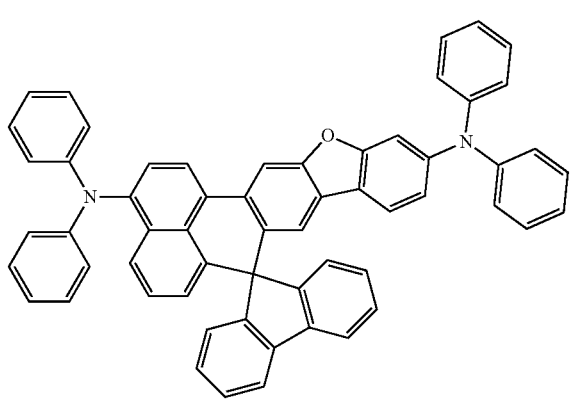
compound 29
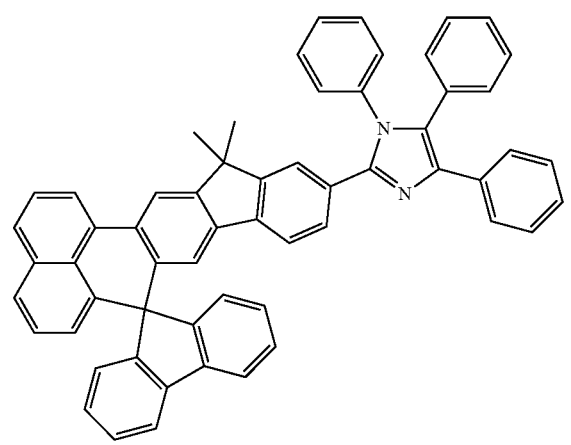
compound 30
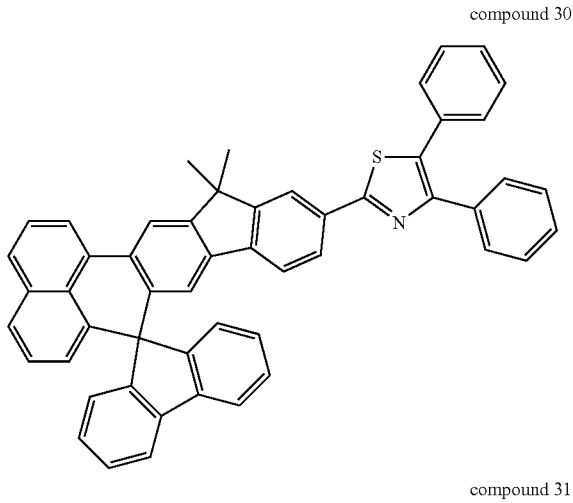
compound 31
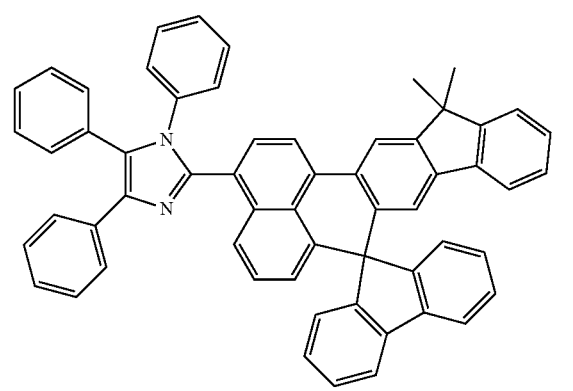
compound 32
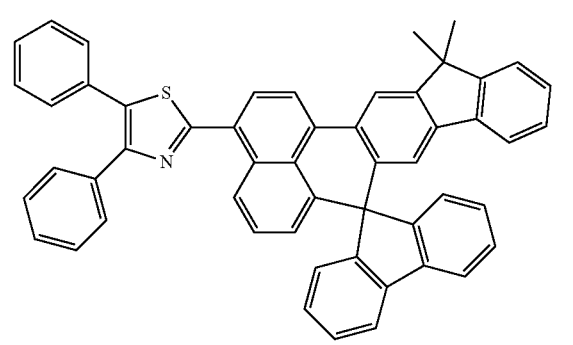
compound 33
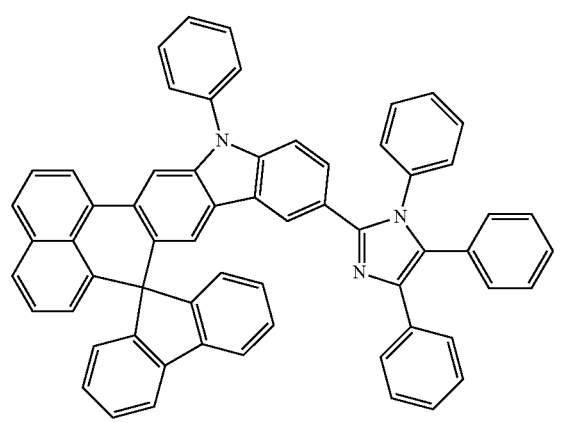

compound 34
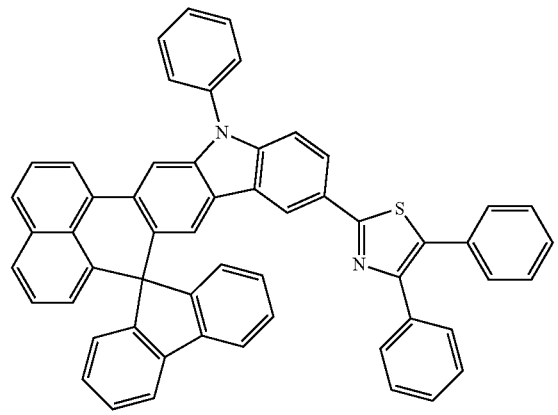
compound 35
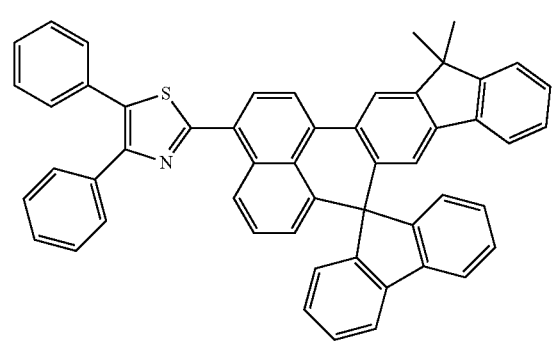
compound 36
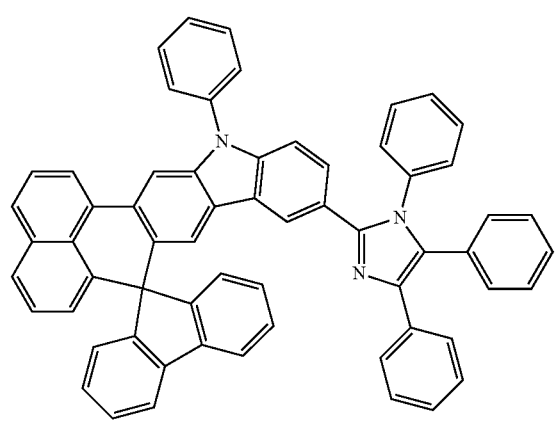
compound 37
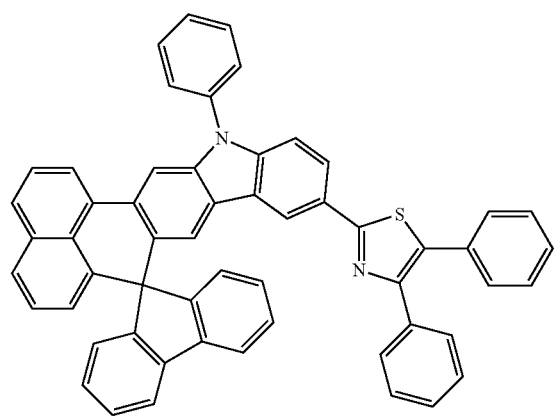
compound 38
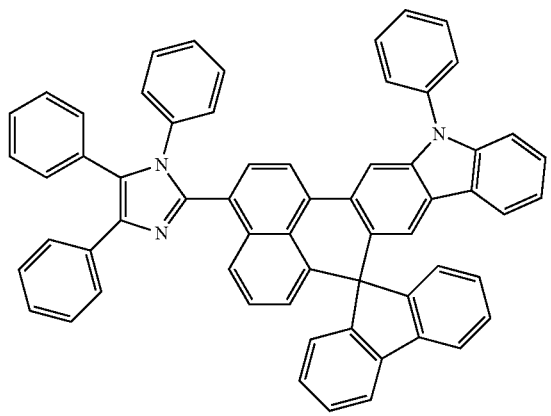
compound 39
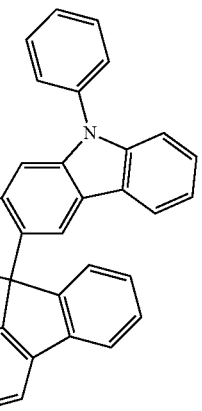
compound 40
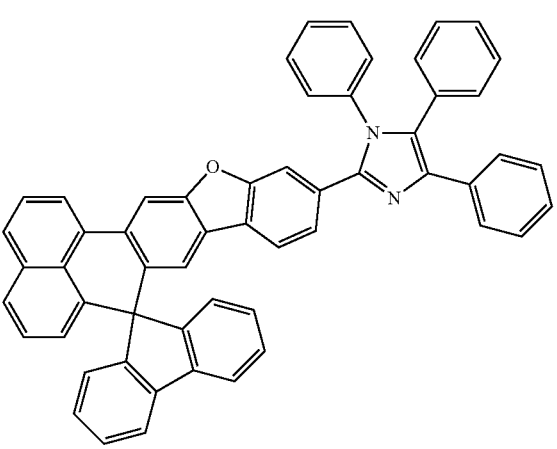

compound 41
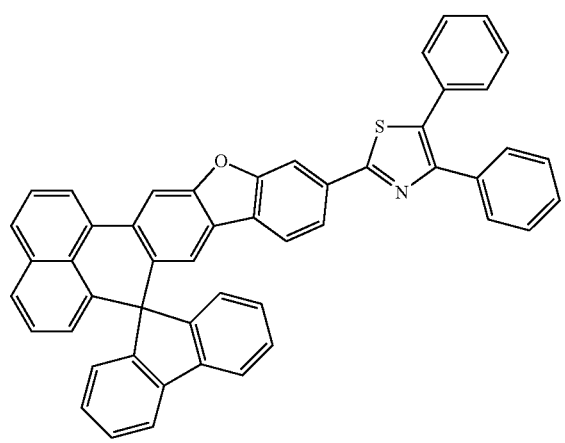
compound 42
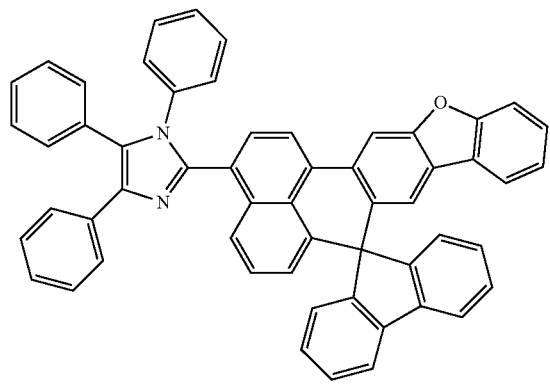
compound 43
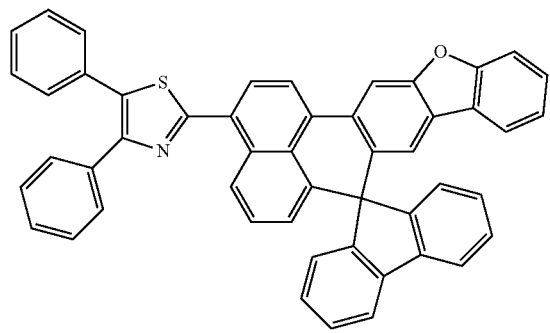
compound 44
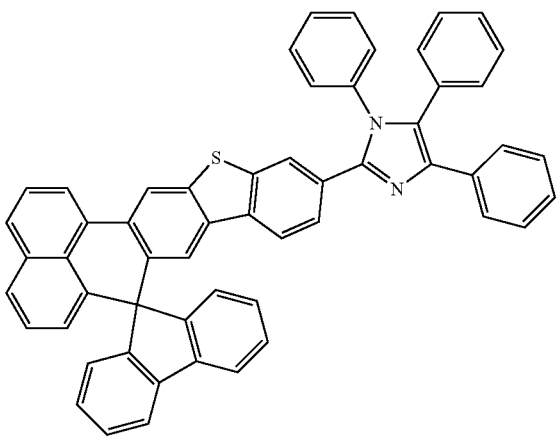
compound 45
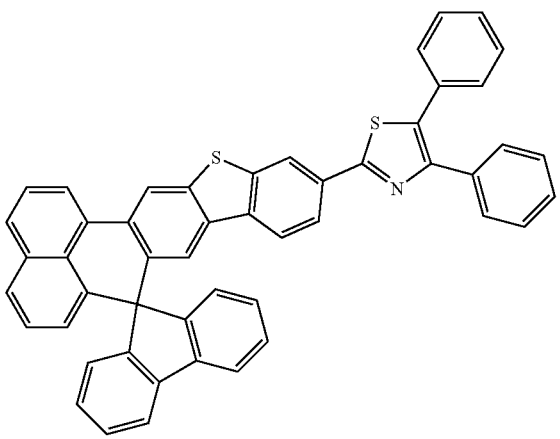
compound 46
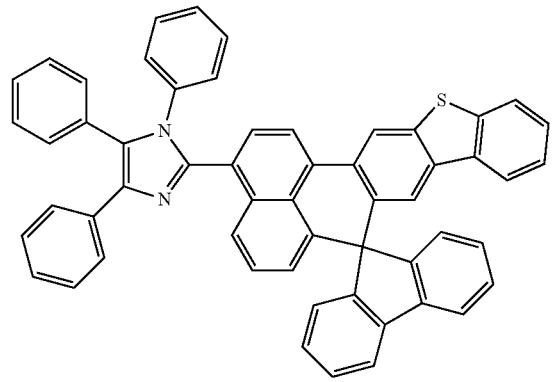

-continued compound 47

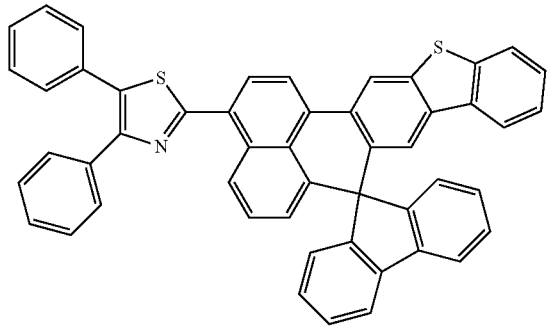

Each of the organic compounds represented by the above Chemical Formulae 2 to 4 has a conformationally rigid spiro-anthracene core bonded by aromatic or heteroaromatic groups or amino groups substituted with aromatic or heteroaromatic groups. Each of the organic compounds has enhanced color purity and may be used a luminous compound for improving luminous efficiency of an organic light-emitting diode or an organic light-emitting device.

[Organic Light-Emitting Diode and Device]

As explained above, the organic compound represented by the Chemical Formulae 1 to 4 may be applied to an emitting material layer of an organic light-emitting diode which has high color purity, low driving voltage and high luminous efficiency. The organic light-emitting diode of the present disclosure may be applied to an organic light-emitting device such as an organic light-emitting display device and an organic lighting device. A display device having the organic light-emitting diode of the present disclosure will be explained. FIG. 1 is a schematic cross-sectional view of illustrating an organic light-emitting display device of the present disclosure.

As illustrated in FIG. 1, the organic light-emitting display device 500 comprises a substrate 502, a thin-film transistor Tr on the substrate 502, and an organic light-emitting diode 600 connected to the thin film transistor Tr.

The substrate 502 may include, but is not limited to, glass, thin flexible material and/or polymer plastics. For example, the flexible material may be selected from the group, but is not limited to, polyimide (PI), polyethersulfone (PES), polyethylenenaphthalate (PEN), polyethylene terephthalate (PET), polycarbonate (PC) and combination thereof. The thin film transistor Tr, and the substrate 502, over which the organic light-emitting diode 600 is arranged, form an array substrate.

A buffer layer 504 may be disposed over the substrate 502, and the thin film transistor Tr is disposed over the buffer layer 504. The buffer layer 504 may be omitted.

A semiconductor layer 510 is disposed over the buffer layer 504. In one exemplary embodiment, the semiconductor layer 510 may comprise oxide semiconductor materials. In this case, a light-shied pattern (not shown) may be disposed under the semiconductor layer 510, and the light-shied pattern (not shown) can prevent light from being incident toward the semiconductor layer 510, and thereby, preventing the semiconductor layer 510 from being deteriorated by the light. Alternatively, the semiconductor layer 510 may comprise, but is not limited to, polycrystalline silicon. In this case, opposite edges of the semiconductor layer 510 may be doped with impurities.

A gate insulating layer 520 formed of an insulating material is disposed on the semiconductor layer 510. The gate insulating layer 520 may include an inorganic insulating material such as silicon oxide (SiO$_x$) or silicon nitride (SiN$_x$).

A gate electrode 530 made of a conductive material such as a metal is disposed over the gate insulating layer 520 so as to correspond to a center of the semiconductor layer 510. While the gate insulating layer 520 is disposed over a whole area of the substrate 502 in FIG. 1, the gate insulating layer 520 may be patterned identically as the gate electrode 530.

An interlayer insulating layer 540 formed of an insulating material is disposed on the gate electrode 530 with covering overran entire surface of the substrate 502. The interlayer insulating layer 540 may comprise an inorganic insulating material such as silicon oxide (SiO$_x$) or silicon nitride (SiN$_x$), or an organic insulating material such as benzocyclobutene or photo-acryl.

The interlayer insulating layer 540 has first and second semiconductor layer contact holes 542 and 544 that expose both sides of the semiconductor layer 510. The first and second semiconductor layer contact holes 542 and 544 are disposed over opposite sides of the gate electrode 530 with spacing apart from the gate electrode 530. The first and second semiconductor layer contact holes 542 and 544 are formed within the gate insulating layer 520 in FIG. 1. Alternatively, the first and second semiconductor layer contact holes 542 and 544 are formed only within the interlayer insulating layer 540 when the gate insulating layer 520 is patterned identically as the gate electrode 530.

A source electrode 552 and a drain electrode 544, which are formed of a conductive material such as a metal, are disposed on the interlayer insulating layer 540. The source electrode 552 and the drain electrode 544 are spaced apart from each other with respect to the gate electrode 530 and contact both sides of the semiconductor layer 510 through the first and second semiconductor layer contact holes 542 and 544, respectively.

The semiconductor layer 510, the gate electrode 530, the source electrode 552 and the drain electrode 554 constitute the thin film transistor Tr, which acts as a driving element. The thin film transistor Tr in FIG. 1 has a coplanar structure in which the gate electrode 530, the source electrode 552 and the drain electrode 554 are disposed over the semiconductor layer 510. Alternatively, the thin film transistor Tr may have an inverted staggered structure in which a gate electrode is disposed under a semiconductor layer and source and drain electrodes are disposed over the semiconductor layer. In this case, the semiconductor layer may comprise amorphous silicon.

Although not shown in FIG. 1, a gate line and a data line, which cross each other to define a pixel region, and a switching element, which is connected to the gate line and the data line, may be further formed in the pixel region. The switching element is connected to the thin film transistor Tr, which is a driving element. In addition, a power line is spaced apart in parallel from the gate line or the data line, and the thin film transistor Tr may further include a storage capacitor configured to constantly keep a voltage of the gate electrode for one frame.

In addition, the organic light-emitting display device 500 may include a color filter (not shown) for absorbing a part of the light emitted from the organic light-emitting diode 600. For example, the color filter (not shown) may absorb a light of specific wavelength such as red (R), green (G) or blue (B). In this case, the organic light-emitting display device 600 can implement full-color through the color filter (not shown).

For example, when the organic light-emitting display device 500 is a bottom-emission type, the color filter (not shown) may be disposed on the interlayer insulating layer 540 with corresponding to the organic light-emitting diode 600. Alternatively, when the organic light-emitting display device 500 is a top-emission type, the color filter (not shown) may be disposed over the organic light-emitting diode 600, that is, a second electrode 620.

A passivation layer 560 is disposed on the source and drain electrodes 552 and 554 over the whole substrate 502. The passivation layer 560 has a flat top surface and a drain contact hole 562 that exposes the drain electrode 554 of the thin film transistor Tr. While the drain contact hole 562 is disposed on the second semiconductor layer contact hole 554, it may be spaced apart from the second semiconductor layer contact hole 554.

The organic light-emitting diode 600 includes a first electrode 610 that is disposed on the passivation layer 560 and connected to the drain electrode 554 of the thin film transistor Tr. The organic light-emitting diode 600 further includes an emitting layer 630 and a second electrode 620 each of which is disposed sequentially on the first electrode 610.

The first electrode 610 is disposed in each pixel region. The first electrode 610 may be an anode and include a conductive material having a relatively high work function value. For example, the first electrode 610 may include, but is not limited to, a transparent conductive material such as indium tin oxide (ITO), indium zinc oxide (IZO), indium tin zinc oxide (ITZO), SnO, ZnO, indium cerium oxide (ICO), aluminum doped zinc oxide (AZO), and the like.

In one exemplary embodiment, when the organic light-emitting display device 500 is a top-emission type, a reflective electrode or a reflective layer (not shown) may be disposed under the first electrode 610. For example, the reflective electrode or the reflective layer (not shown) may include, but is not limited to, aluminum-palladium-copper (APC) alloy.

In addition, a bank layer 570 is disposed on the passivation layer 560 in order to cover edges of the first electrode 610. The bank layer 570 exposes a center of the first electrode 610.

An emitting layer 630 is disposed on the first electrode 610. In one exemplary embodiment, the emitting layer 630 may have a mono-layered structure of an emitting material layer. Alternatively, the emitting layer 630 may have a multiple-layered structure of a hole injection layer, a hole transport layer, an electron blocking layer, an emitting material layer, a hole blocking layer, an electron transport layer and/or an electron injection layer (See, FIGS. 2, 4, 7, 8 and 10). The emitting layer 630 includes the organic compound represented by any one of Chemical Formulae 1 to 4. For example, the organic compound represented by any one of Chemical Formulae 1 to 4 may be used as a dopant of the emitting layer 630, and the emitting layer 630 may include a host and other dopants.

The second electrode 620 is disposed over the substrate 502 above which the emitting layer 630 is disposed. The second electrode 620 may be disposed over a whole display area and may include a conductive material having a relatively low work function value compared to the first electrode 610. The second electrode 620 may be a cathode. For example, the second electrode 620 may include, but is not limited to, aluminum (Al), magnesium (Mg), calcium (Ca), silver (Ag), alloy thereof or combination thereof such as aluminum-magnesium alloy (Al—Mg).

In addition, an encapsulation film 580 may be disposed over the second electrode 620 in order to prevent outer moisture from penetrating into the organic light-emitting diode 600. The encapsulation film may have, but is not limited to, a laminated structure of a first inorganic insulating film 582, an organic insulating film 584 and a second inorganic insulating film 586.

The emitting layer 630 of the organic light-emitting diode 600 may include the organic compound represented by any one of Chemical Formulae 1 to 4 as a dopant, as described above. Such organic compound has rigid spiro-anthracene core and at least one of aromatic or heteroaromatic group(s) and/or amino group(s) bonded to the spiro-anthracene core. It is possible to manufacture an organic light emitting diode 600 and an organic light-emitting display device that can enhance their color purity and luminous efficiency as well as lower their driving voltage.

Figure 2:
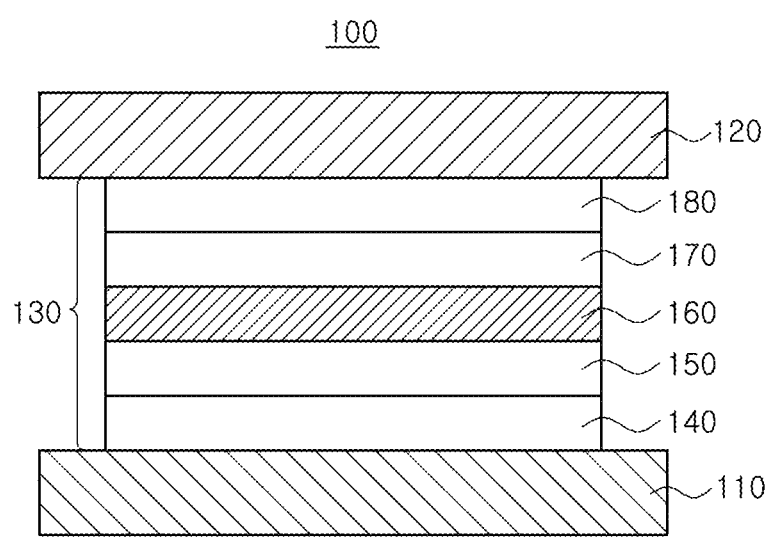
FIG. 2 is a schematic cross-sectional view illustrating an organic light-emitting diode according to an exemplary embodiment of the present disclosure.

FIG. 2 is a schematic cross-sectional view illustrating an organic light-emitting diode having an organic compound as a fluorescent dopant in a single EML in accordance with an exemplary embodiment of the present disclosure.

illustrated in FIG. 2, the organic light-emitting diode (OLED) 100 in accordance with an exemplary embodiment of the present disclosure includes first and second electrodes 110 and 120 facing each other, an emitting layer 130 disposed between the first and second electrodes 110 and 120. In one exemplary embodiment, the emitting layer 130 include a hole injection layer (HIL) 140, a hole transport layer (HTL) 150, an emitting material layer (EML) 160, an electron transport layer (ETL) 170 and an electron injection layer (EIL) 180 each of which is laminated sequentially from the first electrode 110.

The first electrode 110 may be an anode that provides a hole into the EML 160. As described above, the first electrode 110 may include a conductive material having a relatively high work function value, for example, a transparent conductive oxide (TCO). In an exemplary embodiment, the first electrode 110 may include, but is not limited to ITO, IZO, ITZO, SnO, ZnO, ICO, AZO, and the like.

The second electrode 120 may be a cathode that provides an electron into the EML 160. As described above, the second electrode 120 may include a conductive material having a relatively low work function values, i.e., a highly reflective material such as Al, Mg, Ca, Ag, alloy thereof, combination thereof, and the like.

The HIL 140 is disposed between the first electrode 110 and the HTL 150 and improves an interface property between the inorganic first electrode 110 and the organic HTL 150. In one exemplary embodiment, the HIL 140 may include, but is not limited to, 4,4'4"-Tris(3-methylphenylamino)triphenylamine (MTDATA), 4,4',4"-Tris(N,N-diphenyl-amino)triphenylamine (NATA), 4,4',4"-Tris(N-(naphthalene-1-yl)-N-phenyl-amino)triphenylamine (1T-NATA), 4,4',4"-Tris(N-(naphthalene-2-yl)-N-phenyl-amino)triphenylamine (2T-NATA), Copper phthalocyanine (CuPc), Tris(4-carbazoyl-9-yl-phenyl)amine (TCTA), N,N'-Diphenyl-N,N'-bis(1-naphthyl)-1,1'-biphenyl-4,4"-diamine (NPB; NPD), 1,4,5,8,9,11-Hexaazatriphenylenehexacarbonitrile (Dipyrazino[2,3-f: 2'3'-h]quinoxaline-2,3,6,7,10,11-hexacarbonitrile; HAT-CN), 1,3,5-tris[4-(diphenylamino)phenyl]benzene (TDAPB), poly(3,4-ethylenedioxythiophene)polystyrene sulfonate (PEDOT/PSS) and/or N-(biphenyl-4-yl)-9,9-dimethyl-N-(4-(9-phenyl-9H-carbazol-3-yl)phenyl)-9H-fluoren-2-amine. The HIL 140 may be omitted in compliance with a structure of the OLED 100.

The HTL 150 is disposed adjacently to the EML 160 between the first electrode 110 and the EML 160. In one exemplary embodiment, the HTL 150 may include, but is not limited to, N,N'-Diphenyl-N,N'-bis(3-methylphenyl)-1, 1'-biphenyl-4,4'-diamine (TPD), NPB, 4,4'-bis(N-carbazolyl)-1,1'-biphenyl (CBP), Poly[N,N'-bis(4-butylpnehyl)-N,N'-bis(phenyl)-benzidine](Poly-TPD), Poly[(9,9-dioctylfluorenyl-2,7-diyl)-co-(4,4'-(N-(4-sec-butylphenyl) diphenylamine))] (TFB), Di-[4-(N,N-di-p-tolyl-amino)-phenyl]cyclohexane (TAPC), N-(biphenyl-4-yl)-9,9-dimethyl-N-(4-(9-phenyl-9H-carbazol-3-yl)phenyl)-9H-fluoren-2-amine and/or N-(biphenyl-4-yl)-N-(4-(9-phenyl-9H-carbazol-3-yl)phenyl)biphenyl-4-amine.

The EML 160 may include a host and a dopant. In this exemplary embodiment, the EML 160 may include a host (a first host) and the organic compound represented by any one of Chemical Formulae 1 to 4 as a fluorescent dopant (a first fluorescent dopant). The EML 160 may include the fluorescent dopant by about 1 to about 50% by weight and can emit blue color.

The host of the EML 160 may be, but is not limited to, 9-(3-(9H-carbazol-9-yl)phenyl)-9H-carbazole3-carbonitrile (mCP-CN), CBP, 3,3'-bis(N-carbazolyl)-1,1'-biphenyl (mCBP), 1,3-Bis(carbazol-9-yl)benzene (mCP), Oxybis(2, 1-phenylene))bis(diphenylphosphine oxide (DPEPO), 2,8-Bis(diphenylphosphoryl)dibenzothiophene (PPT), 1,3,5-Tri [(3-pyridyl)-phen3-yl]benzene (TmPyPB), 2,6-Di(9H-carbazol-9-yl)pyridine (PYD-2Cz), 2,8-di(9H-carbazol-9-yl)dibenzothiophene (DCzDBT), 3,5'-Di(carbazol-9-yl)[1, 1'-bipheyl]-3,5-dicarbonitrile (DCzTPA), 4'-(9H-carbazol-9-yl)biphenyl-3,5-dicarbonitrile (pCzB-2CN), 3'-(9H-carbazol-9-yl)biphenyl-3,5-dicarbonitrile (mCzB-2CN), Diphenyl-4-triphenylsilylphenyl-phosphine oxide (TPSO1), 9-(9-phenyl-9H-carbazol-6-yl)-9H-carbazole (CCP), 4-(3-(triphenylen-2-yl)phenyl)dibenzo[b,d]thiophene, 9-(4-(9H-carbazol-9-yl)phenyl)-9H-3,9'-bicarbazole, 9-(3-(9H-carbazol-9-yl)phenyl)-9H-3,9'-bicarbazole and/or 9-(6-(9H-carbazol-9-yl)pyridin-3-yl)-9H-3,9'-bicabazole.

Particularly, the host that can be used in the EML 160 may include, but is not limited to, one of H1 to H5 represented by the following structures of Chemical Formula 5:

Chemical Formula 5

H1
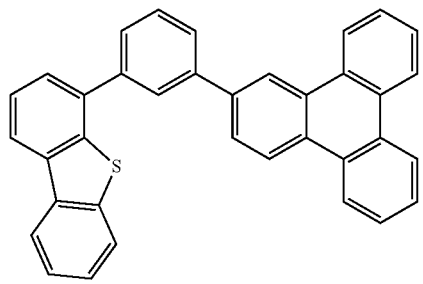

H2
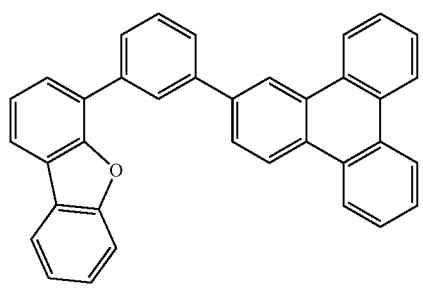

-continued

H3
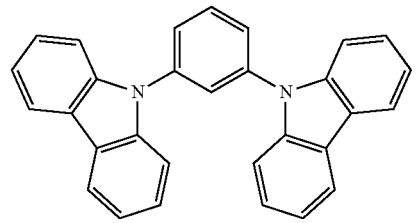

H4
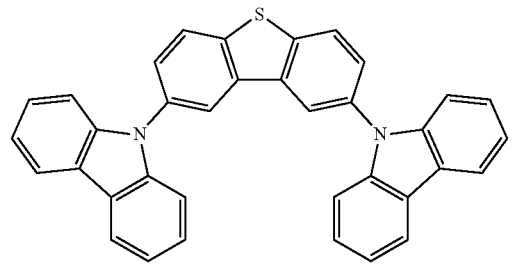

H5
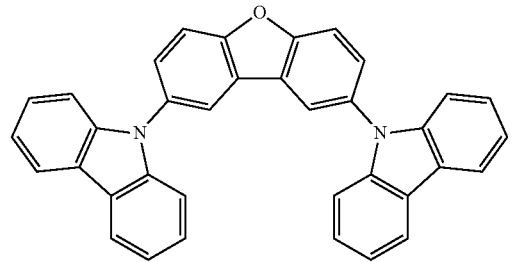

Figure 3:
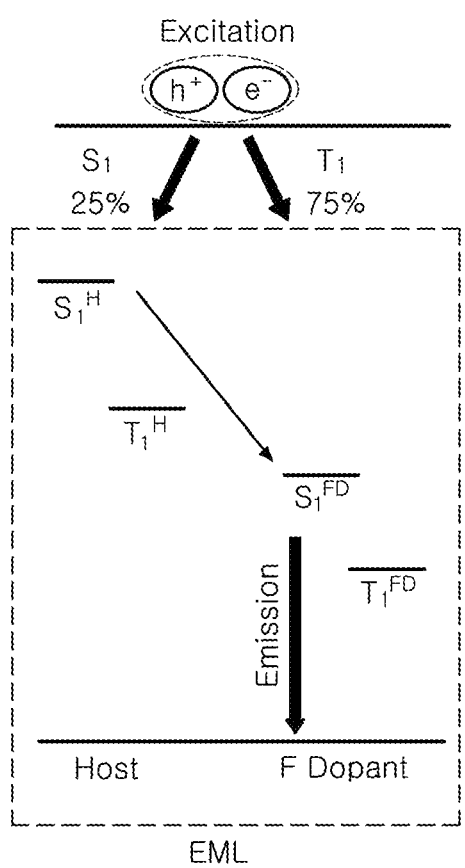
FIG. 3 is s schematic diagram illustrating a luminous mechanism by an energy level bandgap between a host and an organic compound as a fluorescent dopant in a single-layered EML in accordance with an exemplary embodiment of the present disclosure.

In this case, an excited state singlet energy level $S_1^H$ and/or an excited state triplet energy level $T^1{}_H$ of the host is higher than an excited state singlet energy level $S_1^{FD}$ and/or an excited state triplet energy level $T_1^{FD}$ of the first fluorescent dopant (See, FIG. 3).

The ETL 170 and the EIL 180 are laminated sequentially between the EML 160 and the second electrode 120. The ETL 170 includes a material having high electron mobility so as to provide electrons stably with the EML 160 by fast electron transportation.

In one exemplary embodiment, the ETL 170 may include, but is not limited to, oxadiazole-based compounds, triazole-based compounds, phenanthroline-based compounds, benzoxazole-based compounds, benzothiazole-based compounds, benzimidazole-based compounds, triazine-based compounds, and the like.

For example, the ETL 170 may include, but is not limited to, tris-(8-hydroxyquinoline aluminum ($Alq_3$), 2-biphenyl-4-yl-5-(4-t-butylphenyl)-1,3,4-oxadiazole (PBD), spiro-PBD, lithium quinolate (Liq), 1,3,5-Tris(N-phenylbenzimidazol-2-yl)benzene (TPBi), Bis(2-methyl-8-quinolinolato-N1,O8)-(1,1-biphenyl-4-olato)aluminum (BAlq), 4,7-diphenyl-1,10-phenanthroline (Bphen), 2,9-Bis (naphthalene-2-yl)4,7-diphenyl-1,10-phenanthroline (NBphen), 2,9-Dimethyl-4,7-diphenyl-1,10-phenathroline (BCP), 3-(4-Biphenyl)-4-phenyl-5-tert-butylphenyl-1,2,4-triazole (TAZ), 4-(Naphthalen-1-yl)-3,5-diphenyl-4H-1,2,4-triazole (NTAZ), 1,3,5-Tri(p-pyrid3-yl-phenyl)benzene (TpPyPB), 2,4,6-Tris(3'-(pyridin-3-yl)biphenyl-3-yl)1,3,5-triazine (TmPPPyTz), Poly[9,9-bis(3'-((N,N-dimethyl)-N-ethylammonium)-propyl)-2,7-fluorene]-alt-2,7-(9,9-dioctylfluorene)](PFNBr) and/or tris(phenylquinoxaline) (TPQ).

The EIL 180 is disposed between the second electrode 120 and the ETL 170, and can improve physical properties of the second electrode 120 and therefore, can enhance the life span of the OLED 100. In one exemplary embodiment, the EIL 180 may include, but is not limited to, an alkali halide such as LiF, CsF, NaF, $BaF_2$ and the like, and/or an organic metal compound such as lithium benzoate, sodium stearate, and the like.

In one exemplary embodiment, when the EML 160 includes the host and the first fluorescent dopant that may be the organic compound represented by any one of Chemical Formulae 1 to 4, it is necessary to adjust excited state singlet energy levels and/or excited state triplet energy levels between the host and the first fluorescent dopant. FIG. 3 is a schematic diagram illustrating luminous mechanism by energy level bandgap between a host and a fluorescent dopant in a single EML in accordance with an exemplary embodiment of the present disclosure.

As illustrated in FIG. 3, each of the excited state singlet energy level $S_1^H$ and the excited state triplet energy level $T_1^H$ of the host is higher than the excited state singlet energy level $S_1^{FD}$ and the excited state triplet energy level $T_1^{FD}$ of the first fluorescent dopant, respectively, so that exciton energy generated in the host can transfer to the first fluorescent dopant. In one exemplary embodiment, an emission wavelength range of the host can overlap much more with an absorption wavelength range of the first fluorescent dopant so that the exciton energy can transfer efficiently from the host to the first fluorescent dopant.

Since the EML 160 includes the organic compound represented by any one of Chemical Formulae 1 to 4, which has a rigid anthracene core bonded by amino group substituted with aromatic or heteroaromatic group and/or by aromatic or heteroaromatic group, as a fluorescent dopant, its color purity can be enhanced. In addition, it is possible to lower driving voltage and to improve luminous efficiency and life span of the OLED 100 using the structurally-stable fluorescent dopant.

Figure 4:
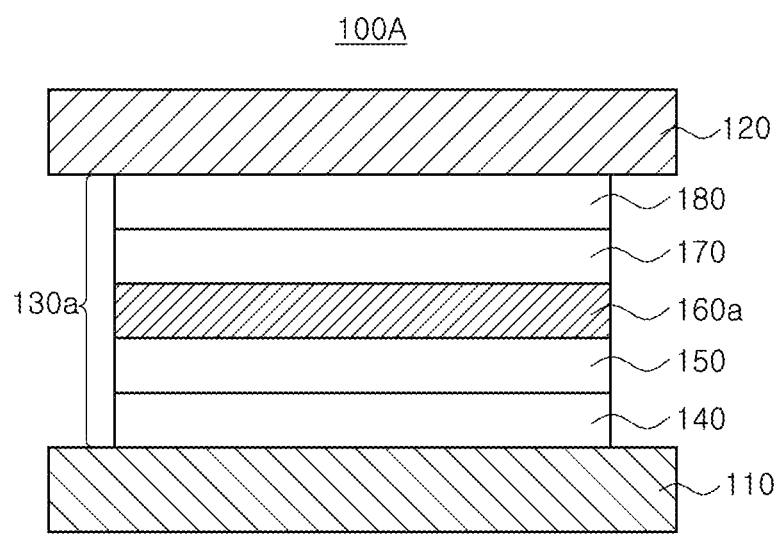
FIG. 4 is a schematic cross-sectional view illustrating an organic light-emitting diode in accordance with another exemplary embodiment of the present disclosure.

While the EML 160 includes only a host and a fluorescent dopant in the above embodiment, the EML may have two or more dopants. FIG. 4 is a schematic cross-sectional view illustrating an OLED having a host, a delayed fluorescent material as a first dopant, and the organic compound represented by any one of Chemical Formulae 1 to 4 as a second dopant in a single EML in accordance with another exemplary embodiment of the present disclosure. As illustrated in FIG. 4, the OLED 100A in accordance with another embodiment of the present disclosure includes first and second electrodes 110 and 120 facing each other and an emitting layer 130a disposed between the first and second electrodes 110, 120.

In one exemplary embodiment, the emitting layer 130a may include an HIL 140, an HTL 150, an EML 160a, an ETL 170 and an EIL 180 each of which is laminated sequentially from the first electrode 110.

In this embodiment, the EML 160a may include a host (a first host), a first dopant and a second dopant. The first dopant may be a delayed fluorescent dopant (T dopant) such as thermally activated delayed fluorescent dopant, and the second dopant may be a fluorescent dopant (F dopant). For example, the organic compound represented by any one of Chemical Formulae 1 to 4 may be used as the second dopant. When the EML 160a further include the delayed fluorescent dopant as the first dopant, it is possible to implement OLED 100A that improve luminous efficiency remarkably by adjusting the energy levels among the host and the dopants.

The delayed fluorescence can be classified into thermally activated delayed fluorescence (TADF) and filed activated delayed fluorescence (FADF). Triplet exciton can be activated by heat or electrical field in the delayed fluorescence so that super-fluorescence beyond the maximal luminous efficiency by conventional fluorescent material can be implemented.

Figure 5:
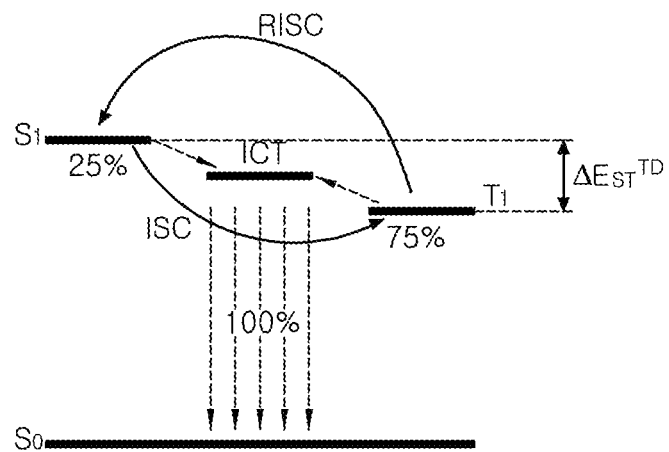
FIG. 5 is a schematic diagram illustrating a luminous mechanism of the delayed fluorescent material in accordance with another exemplary embodiment of the present disclosure.

Since the triplet excitons within the delayed fluorescent material can be activated by heat or electrical field generated during driving the diode, the triplet excitons can be involved in emission processes, as illustrated in FIG. 5, which is a schematic diagram showing luminous mechanism of the delayed fluorescent material in EML in accordance with another exemplary embodiment of the present disclosure.

Since the delayed fluorescent material generally has both an electron donor moiety and an electron acceptor moiety, it can be converted to an intramolecular charge transfer (ICT) state. In case of using the delayed fluorescent material, which can be converted to an ICT state, as a dopant, both the excitons of singlet energy level $S_1$ and the excitons of triplet energy level $T_1$ can move to an intermediate energy level state, i.e. ICT state, and then the intermediate stated excitons can be transferred to a ground state ($S_0$; $S_1 \rightarrow ICT \leftarrow T_1$). Since both the excitons of singlet energy level $S_1$ and the excitons of triplet energy level $T_1$ in the delayed fluorescent material is involved in the emission process, the delayed fluorescent material can improve internal quantum efficiency and luminous efficiency.

Since both the Highest Occupied Molecular Orbital (HOMO) and the Lowest Unoccupied Molecular orbital (LUMO) are widely distributed over the entire molecule within the common fluorescent material, it is not possible to inter-convert between the single energy level and the triplet energy level within it (selection rule). In contrast, since the delayed fluorescent material, which can be converted to an ICT state, has little orbital overlaps between HOMO and LUMO, there is little interaction between the HOMO state molecular orbital and the LUMO state molecular orbital within the delayed fluorescent material. As a result, the changes of spin states of electrons does not have an influence on other electrons, and a new charge transfer band (CT band) that does not follow the selection rule is formed in the delayed fluorescent material.

In other words, since the delayed fluorescent material has the electron acceptor moiety spacing apart from the electron donor moiety within the molecule, it exists as a polarized state having a large dipole moment within the molecule. As the interaction between HOMO molecular orbital and LUMO molecular orbital becomes little with the polarized state of the dipole moment, both the triplet energy level excitons and the singlet energy level excitons can be converted to ICT state. Accordingly, both the excitons of triplet energy level $T_1$ as well as the excitons of singlet energy level $S_1$ can participate in the emission process.

In case of driving a diode that includes the delayed fluorescent material, 25% excitons of singlet energy level $S_1$ and 75% excitons of triplet energy level $T_1$ are converted to ICT state by heat or electrical field, and then the converted excitons transfer to the ground state $S_0$ with luminescence. Therefore, the delayed fluorescent material may have 100% internal quantum efficiency in theory.

The delayed fluorescent material must has an energy bandgap $\Delta EST^{TD}$ equal to or less than about 0.3 eV, for example, from about 0.05 to about 0.3 eV, between the singlet energy level $S_1$ and the triplet energy level $T_1$ so that exciton energy in both the singlet energy level and the triplet energy level can be transferred to the ICT state. The material having little energy level bandgap between the singlet energy level $S_1$ and the triplet energy level $T_1$ can exhibit common fluorescence with Inter system Crossing (ISC) in which the excitons of singlet energy level $S_1$ can be transferred to the excitons of triplet energy level $T_1$, as well as delayed fluorescence with Reverser Inter System Crossing (RISC) in which the excitons of triplet energy level $T_1$ can be transferred upwardly to the excitons of single energy level $S_1$, and then the exciton of singlet energy level $S_1$ can be transferred to the ground state $S_0$.

Since the delayed fluorescent material can exhibit 100% internal quantum efficiency in theory, it can implement as high luminous efficiency as the conventional phosphorescent material including a heavy metal. However, due to the bond conformation between the electron acceptor-electron donor and the sterical twists in the delayed fluorescent material, and additional charge transfer transition (CT transition) caused by them, the delayed fluorescent material shows broad spectrum in the course of emission, which results in poor color purity.

In one exemplary embodiment of the present disclosure, the EML 160a includes the compound represented by any one of Chemical Formulae 1 to 4 as the second dopant (fluorescent dopant) so as to prevent the color purity of the OLED 100A from being lowered in spite of using the delayed fluorescent material as the first dopant. The excitons of triplet energy level $T_1$ can be transferred to the excitons of the singlet energy level $S_1$ in the delayed fluorescent dopant by RISC, and the singlet energy of the delayed fluorescent dopant can be transferred to the fluorescent dopant in the same EML by Dexter energy transfer that depends upon wave function overlaps among adjacent molecules by inter-molecular electron exchanges and exciton diffusions.

In this case, since the ultimate emission in the EML 160a is done at the second dopant, i.e., the organic compound represented by any one of Chemical Formulae 1 to 4, which has a narrow FWHM (full width at half maximum) during transferring the exciton energy from the excited state to the ground state, the OLED 100A can enhance its color purity. In addition, since the OLED 100A can significantly improve the luminous efficiency, it is possible to implement hyper-fluorescent diode.

In an exemplary embodiment, the host in the EML 160a may be, but is not limited to, mCP-CN, CBP, mCBP, mCP, DPEPO, TmPyPB, PYD-2Cz, DCzDBT, DCzTPA, pCzB-2CN, mCzB-2CN, TPSO1, CCP, 4-(3-(triphenylen-2-yl)phenyl)dibenzo[b,d]thiophene, 9-(4-(9H-carbazol-9-yl)phenyl)-9H-3,9'-bicarbazole, 9-(3-(9H-carbazol-9-yl)phenyl)-9H-3,9'-bicarbazole and/or 9-(6-(9H-carbazol-9-yl)pyridin-3-yl)-9H-3,9'-bicabazole.

In another exemplary embodiment, the first dopant (delayed fluorescent dopant) used in the EML 160a may be, but is not limited to, bis(4-(9H-carbazol-9-yl)phenyl)methanone (Cz2BP), 9-(3-(9H-Carbazol-9-yl)-5-(4,6-diphenyl-1,3,5-triazin-2-yl)phenyl)-9H-carbazole (DcrTrZ), 3-(9H-Carbazol-9-yl)-9-(4-(4,6-diphenyl-1,3,5-triazin-2-yl)phenyl)-9H-carbazole (4-DcrTrZ), 10-(4-(4,6-diphenyl-1,3,5-triazin-2-yl)phenyl)-10H-spiro[acridine-9,9'-xanthene], 4,5-di(9H-carbazol-9-yl) phthalonitrile (2CzPN), 2,4,5,6-Tetra(9H-carbazol-9-yl)isophthalonitile (4CzIPN), 3,4,5,6-Tetrakis(carbazol-9-yl)-1,2-dicyanobenzene (4CzPN), 4,4''-Di(10H-phenoxazin-10-yl)-[1,1':2',1''-terphenyl]-4,5-dicarbonitrile (Px-VPN), 9,9',9''-(5-(4,6-diphenyl-1,3,5-triazin-2-yl)benzene-1,2,3-triyl) tris(9H-carbazole (TczTRZ) and/or 12-(4-(4,6-diphenyl-1,3,5-triazin-2-yl)phenyl-5-phenyl-5,12-dihydroindolo[3,2-a]carbazole (32alCTRZ). Particularly, the delayed fluorescent dopant can be used as the first dopant in EML 160a may be any one of the following structures of Chemical Formula 6:

Chemical Formula 6

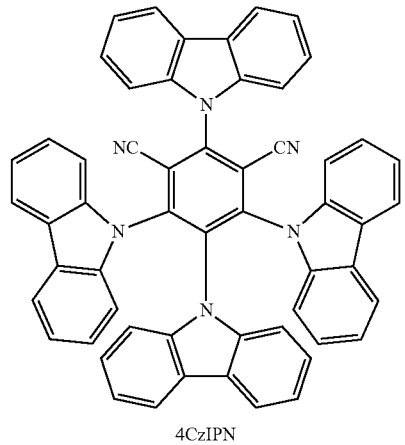

4CzIPN

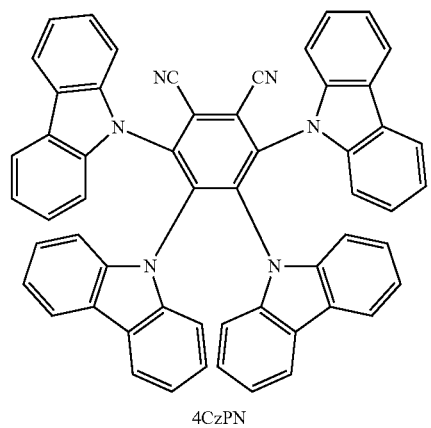

4CzPN

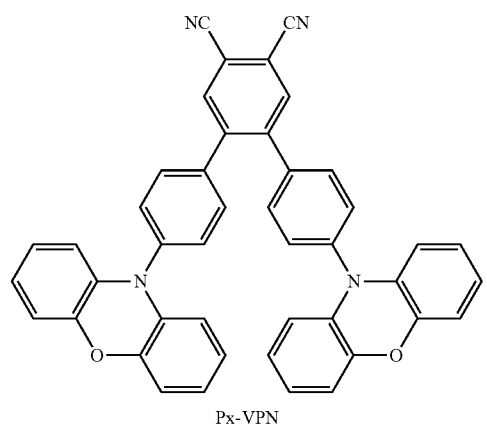

Px-VPN

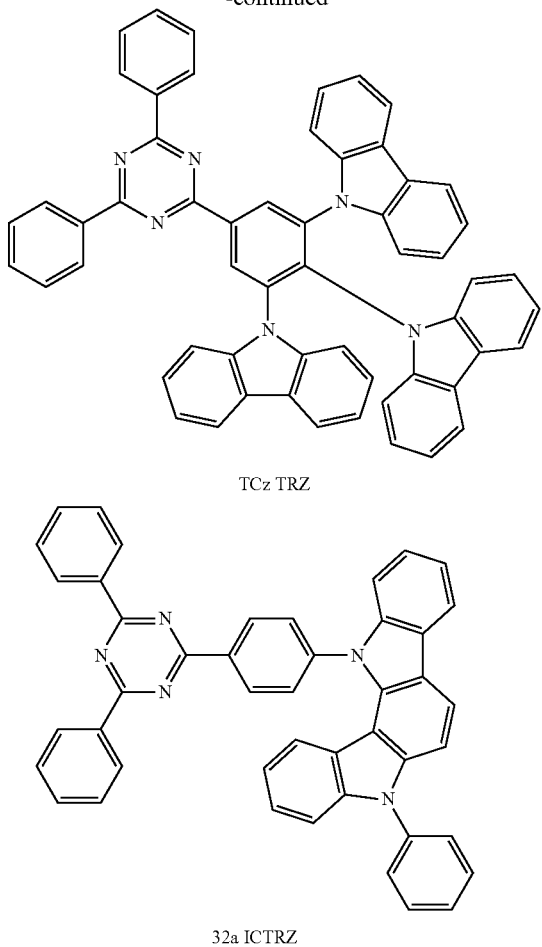

TCz TRZ

32a ICTRZ

As such, when the EML 160a includes a host (first host), a delayed fluorescent dopant (first dopant) and the organic compound represented by any one of Chemical Formulae 1 to 4 as a fluorescent dopant (second dopant), it is possible to implement hyper fluorescence and to improve color purity by adjusting energy levels among the host, the first dopant and the second dopant.

In other words, the EML 160a in accordance with second embodiment of the present disclosure includes the organic compound represented by any one of Chemical Formulae 1 to 4 as the second dopant. The organic compound has a structurally rigid spiro-anthracene core bonded by at least one of the aromatic or heteroaromatic group and amino group substituted with aromatic or heteroaromatic group and a narrow FWHM. Accordingly, it is possible to implement an OLED that enables it to drive at lower voltage and enhance its luminous efficiency and color purity using the organic compound represented by any one of Chemical Formulae 1 to 4. In addition, it is also possible to maximize the luminous efficiency and the life span of the OLED 100A when the EML 160a includes the delayed fluorescent dopant.

Figure 6:
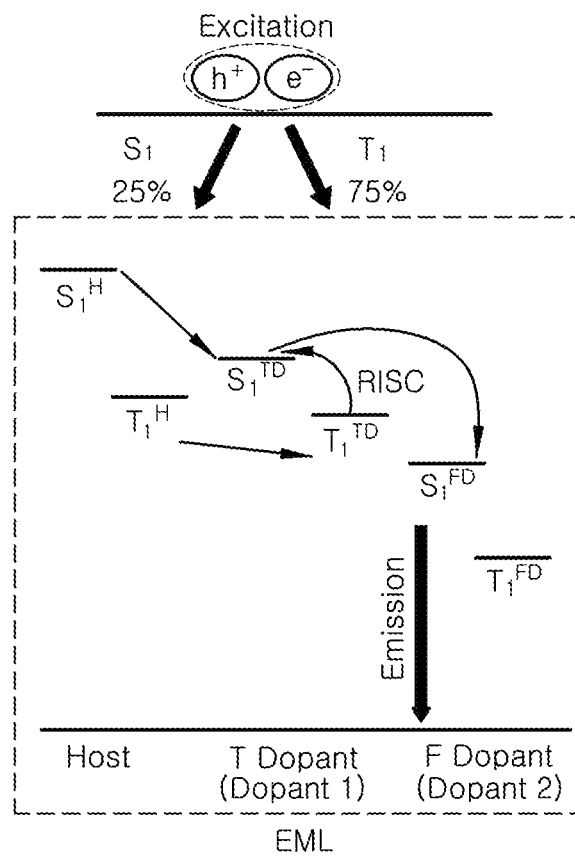
FIG. 6 is a schematic diagram illustrating a luminous mechanism by an energy level bandgap among a host, a fluorescent dopant and a delayed fluorescent dopant in a single-layered EML in accordance with another exemplary embodiment of the present disclosure.

FIG. 6 is a schematic diagram illustrating luminous mechanism by energy level bandgap among the host, the first dopant (delayed fluorescent dopant) and the second dopant (fluorescent dopant) in EML in accordance with another exemplary embodiment of the present disclosure. With referring to FIG. 6, each of an excited state singlet energy level $S_1^H$ and an excited state triplet energy $T_1^H$ of the host must be higher than each of an excited state singlet energy level $S_1^{TD}$ and an excited state triplet energy level $T_1^{TD}$ of the delayed fluorescent dopant, respectively, so that the exciton energy generated within the host can be transferred to the delayed fluorescent dopant in advance.

When the excited state triplet energy level $T_1^H$ of the host is not higher enough than the excited state triplet energy level $T_1^{TD}$ of the delayed fluorescent dopant, the excitons of the triplet state of the delayed fluorescent dopant can be transferred to the excited state triplet energy level $T_1^H$ of the host. Accordingly, the excitons of the triplet state $T_1^{TD}$ of the delayed fluorescent dopant may be disappeared as a non-emission and they cannot contribute to the emission. For example, the excited state triplet energy level $T_1^H$ of the host may be high by at least 0.2 eV compared to the excited state triplet energy level $T_1^{TD}$ of the first dopant.

In addition, it is necessary to adjust property Highest Occupied Molecular Orbital (HOMO) energy levels and Lowest Unoccupied Molecular Orbital (LUMO) energy levels of the host and the delayed fluorescent dopant. For example, it is preferable that an energy level bandgap ($|HOMO^H - HOMO^{TD}|$) between a Highest Occupied Molecular Orbital energy level ($HOMO^H$) of the host and a Highest Occupied Molecular Orbital energy level ($HOMO^{TD}$) of the delayed fluorescent dopant, or an energy level bandgap ($|LUMO^H - LUMO^{TD}|$) between a Lowest Unoccupied Molecular Orbital energy level ($LUMO^H$) of the host and a Lowest Unoccupied Molecular Orbital energy level ($LUMO^{TD}$) of the first dopant may be equal to or less than about 0.5 eV, for example, between about 0.1 eV to about 0.5 eV. In this case, the charges can be moved efficiently from the host to the delayed fluorescent dopant and thereby enhancing an ultimate luminous efficiency.

In addition, it is necessary to implement OLED that enables transfer energies from the delayed fluorescent dopant, which has been converted to ICT complex state by RISC, to the second dopant of the fluorescent material in EML 160a, and has high luminous efficiency and color purity. In order to implement such an OLED, each of the excited state singlet energy level $S_1^{TD}$ and/or the excited state triplet energy level $T_1^{TD}$ of the first dopant must be higher than an excited state singlet energy level $S_1^{FD}$ and/or an excited state triplet energy level $T_1^{FD}$ of the second dopant.

When the EML 160a includes the host, the delayed fluorescent dopant (first dopant) and the fluorescent dopant (second dopant), it may include the host more than the dopants by weight ratio. In one embodiment, the EML 160a may include the first dopant more than the second dopant by weight ration. For example, the contents of the host may be larger than the contents of the first dopant by weight in the EML 160a, and the contents of the first dopant may be larger than the contents of the second dopant by weight in the EML 160a. In this case, the exciton energy can be transferred efficiently from the first dopant to the second dopant in the EML 160a. For example, when the EML 160a includes the host, the delayed fluorescent dopant (first dopant) and the fluorescent dopant (second dopant), the first and second dopants may comprise by about 1 to about 50% by weight in the EML 160a.

Figure 7:
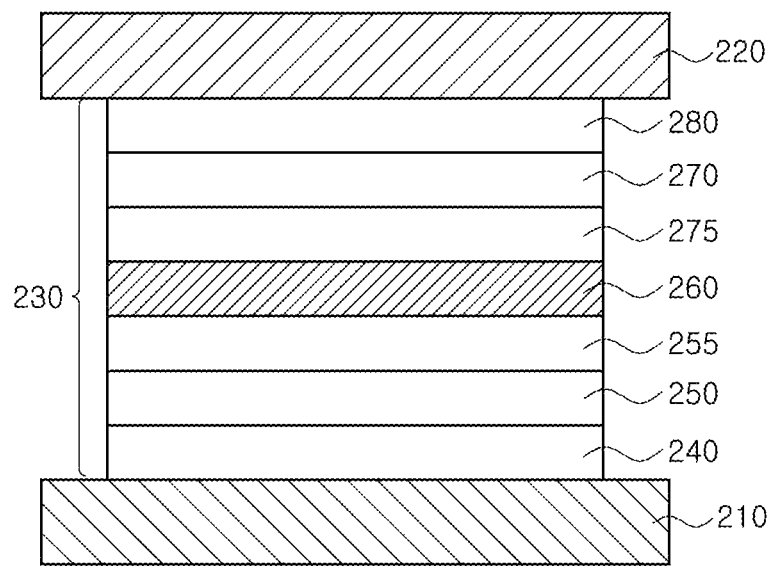
FIG. 7 is a schematic cross-sectional view illustrating an organic light-emitting diode in accordance with another exemplary embodiment of the present disclosure.

In addition, an OLED in accordance with the present disclosure may further include one or more exciton blocking layers. FIG. 7 is a schematic cross-sectional view illustrating an organic light-emitting diode having an organic compound as a fluorescent dopant in a single EML in accordance with another exemplary embodiment of the present disclosure. As illustrated in FIG. 7, an OLED 200 in accordance with the third embodiment of the present disclosure includes first and second electrodes 210 and 220, and an emitting layer 230 disposed between the first and second electrodes 210 and 220.

In an exemplary embodiment, the emitting layer 230 includes an HIL 240, an HTL 250, an EML 260, an ETL 270 and an EIL 280 each of which is laminated sequentially above the first electrode 210. In addition, the emitting layer 230 further include a first exciton blocking layer, i.e. an electron blocking layer (EBL) 255 disposed between the HTL 250 and the EML 260 and/or a second exciton blocking layer, i.e., a hole blocking layer (HBL) 275 disposed between the EML 260 and the ETL 270.

As mentioned above, the first electrode 210 may be a anode and include, but is not limited to, a conductive material having a relatively large work function values such as ITO, IZO, SnO, ZnO, ICO, AZO, and the like. The second electrode 220 may be a cathode and may include, but is not limited to, a conductive material having a relatively small work function values such as Al, Mg, Ca, Ag, alloy thereof or combination thereof.

The HIL 240 is disposed between the first electrode 210 and the HTL 250. The HIL 240 may include, but is not limited to, MTDATA, NATA, 1T-NATA, 2T-NATA, CuPc, TCTA, NPB(NPD), HAT-CN, TDAPB, PEDOT/PSS and/or N-(biphenyl-4-yl)-9,9-dimethyl-N-(4-(9-phenyl-9H-carbazol3-yl)phenyl)-9H-fluoren-2-amine. The HIL 240 may be omitted in compliance with the structure of the OLED 200.

The HTL 250 is disposed adjacent to the EML 260 between the first electrode 210 and the EML 260. The HTL 250 may include, but is not limited to, aromatic amine compounds such as TPD, NPD(NPB), CBP, poly-TPD, TFB, TAPC,), N-(biphenyl-4-yl)-9,9-dimethyl-N-(4-(9-phenyl-9H-carbazol3-yl)phenyl)-9H-fluoren-2-amine and/or N-(biphenyl-4-yl)-N-(4-(9-phenyl-9H-carbazol-3-yl)phenyl)biphenyl-4-amine.

The EML 260 may include a host (first host) and at least one dopant. In an exemplary embodiment, the EML 260 may include a host and the organic compound represented by any one of Chemical Formulae 1 to 4 as the fluorescent dopant (first fluorescent dopant). For example, the EML 260 may include the fluorescent dopant by about 1% to 50% by weight. In an exemplary embodiment, the excited state triplet energy level $T_1^H$ and/or the excited state singlet energy level $S_1^H$ of the host is higher than the excited state triplet energy level $T_1^{FD}$ and/or the excited state singlet energy level $S_1^{FD}$ of the first fluorescent dopant (See, FIG. 3).

In another exemplary embodiment, the EML 260 may include a host (first host), a first dopant and a second dopant. The first dopant may be a delayed fluorescent dopant, and the second dopant may be a fluorescent dopant. The organic compound represented by any one of Formulae 1 to 4 may be used as the second dopant.

In one exemplary embodiment, the host may be, but is not limited to, mCP-CN, CBP, mCBP, MCP, DPEPO, PPT, TmPyPB, PYD-2CZ, DCzDBT, DCzTPA, pCzB-2CN, mCzB-2CN, TPSO1, CCP, 4-(3-(triphenylen-2-yl)phenyl)dibenzo[b,d]thiophene, 9-(4-(9H-carbazol-9-yl)phenyl)-9H-3,9'-bicarbazole, 9-(3-(9H-carbazol-9-yl)phenyl)-9H-3,9'-bicarbazole and/or 9-(6-(9H-carbazol-9-yl)pyridin3-yl)-9H-3,9'-bicabazole. Particularly, the host may comprise, but is not limited to, any one of H1 to H5 represented by Chemical Formula 5 above.

The first dopant may be, but is not limited to, Cz2BP, DcrTrZ, 4-DcrTrZ, 10-(4-(4,6-diphenyl-1,3,5-triazin-2-yl)phenyl)-10H-spiro[acridine-9,9'-xanthene], 2CzPN, 4CzIPN, 4CzPN, Px-VPN, TczTRZ and/or 32alCTRZ). Particularly, the delayed fluorescent dopant may be, but is not limited to, any one of Chemical Formula 6 above.

In this case, an energy bandgap between the excited state singlet energy level $S_1^{TD}$ and the excited state triplet energy level $T_1^{TD}$ of the first dopant may be equal to or less than about 0.3 eV. In addition, the excited state singlet energy level $S_1^H$ and/or the excited state triplet energy level $T_1^H$ of the host are higher than the excited state singlet energy level $S_1^{TD}$ and/or the excited state triplet energy level $T_1^{TD}$ of the first dopant. For example, the excited state triplet energy level $T_1^H$ of the host may be higher than the excited state triplet energy level $T_1^{TD}$ of the first dopant by at least about 0.2 eV. In addition, the excited state singlet energy level $S_1^{TD}$ and/or the excited state triplet energy level $T_1^{TD}$ of the first dopant are higher than the excited state singlet energy level $S_1^{FD}$ and/or the excited state triplet energy level $T_1^{FD}$ of the second dopant.

Also, an energy level bandgap ($|HOMO^H-HOMO^{TD}|$) between a Highest Occupied Molecular Orbital energy level ($HOMO^H$) of the host and a Highest Occupied Molecular Orbital energy level ($HOMO^{TD}$) of the first dopant, or an energy level bandgap ($|LUMO^H-LUMO^{TD}|$) between a Lowest Unoccupied Molecular Orbital energy level (LUMO$^H$) of the first host and a Lowest Unoccupied Molecular Orbital energy level (LUMO$^{TD}$) of the first dopant may be equal to or less than about 0.5 eV. In case the EML 260 includes the host, the first dopant and the second dopant, the EML 260 may comprise the first and second dopants about 1 to about 50% by weight.

The ETL 270 is disposed between the EML 260 and the EIL 280. For example, the ETL 270 may include, but is not limited to, oxadiazole-based compounds, triazole-based compounds, phenanthroline-based compounds, benzoxazole-based compounds, benzothiazole-based compounds, benzimidazole-based compounds, triazine-based compounds, and the like. For example, the ETL 270 may include, but is not limited to, Alq$_3$, PBD, spiro-PBD, Liq, TPBi, BAlq, Bphen, NBphen, BCP, TAZ, NTAZ, TpPyPB, TmPPPyTz, PFNBr and/or TPQ.

The EIL 280 is disposed between the second electrode 220 and the ETL 270. The ETL 280 may include, but is not limited to, an alkali halide such as LiF, CsF, NaF, BaF$_2$ and the like, and/or an organic metal compound such as lithium benzoate, sodium stearate, and the like.

When holes are transferred to the second electrode 220 via the EML 260 and/or electrons are transferred to the first electrode 210 via the EML 260, the OLED 300 may have short lifespan and reduced luminous efficiency. In order to prevent these phenomena, the OLED 200 in accordance with the third embodiment of the present disclosure has at least one exciton blocking layer adjacent to the EML 260.

For example, the OLED 200 of the exemplary embodiment includes the EBL 255 between the HTL 250 and the EML 260 so as to control and prevent electron transfers. In one exemplary embodiment, the EBL 255 may include, but is not limited to, TCTA, Tris[4-(diethylamino)phenyl]amine, N-(bipnehyl-4-yl)-9,9-dimethyl-N-(4-(9-phenyl-9H-carbazol3-yl)phenyl)-9H-fluorene-2-amine, TAPC, MTDATA, mCP, mCBP, CuPc, N,N'-bis[4-(bis(3-methylphenyl)amino)phenyl]-N,N'-diphenyl-[1,1'-biphenyl]-4,4'-diamine (DNTPD) and/or TDAPB.

In addition, the OLED 200 further includes the HBL 275 as a second exciton blocking layer between the EML 260 and the ETL 270 so that holes cannot be transferred from the EML 260 to the ETL 270. In one exemplary embodiment, the HBL 275 may include, but is not limited to, oxadiazole-based compounds, triazole-based compounds, phenanthroline-based compounds, benzoxazole-based compounds, benzothiazole-based compounds, benzimidazole-based compounds, and triazine-based compounds.

For example, the HBL 275 may include a compound having a relatively low HOMO energy level compared to the emitting material in EML 260. The HBL 275 may include, but is not limited to, BCP, BAlq, Alq₃, PBD, spiro-PBD, Liq, Bis-4,5-(3,5-di3-pyridylphenyl)-2-methylpyrimidine (B3PYMPM) and combination thereof.

The OLED 200 in accordance with the third embodiment of the present disclosure include the organic compound represented by any one of Chemical Formulae 1 to 4 as the dopant in the EML 260. It is possible to manufacture an OLED 200 that enable it to drive at lower voltage and enhance its luminous efficiency and color purity. In addition, when the EML 260 includes the delayed fluorescent dopant, it is possible to significantly improve the luminous efficiency (hyper-fluorescence) and the life span of the diode. In addition, the OLED 200 further includes at least one exciton blocking layers 255 and 275. Since such exciton blocking layers 255 and 275 can prevent emissions at interfaces between the charge transport layers 250 and 270 and the EML 260, the OLED 270 can enhance further luminous efficiency and life span.

Figure 8:
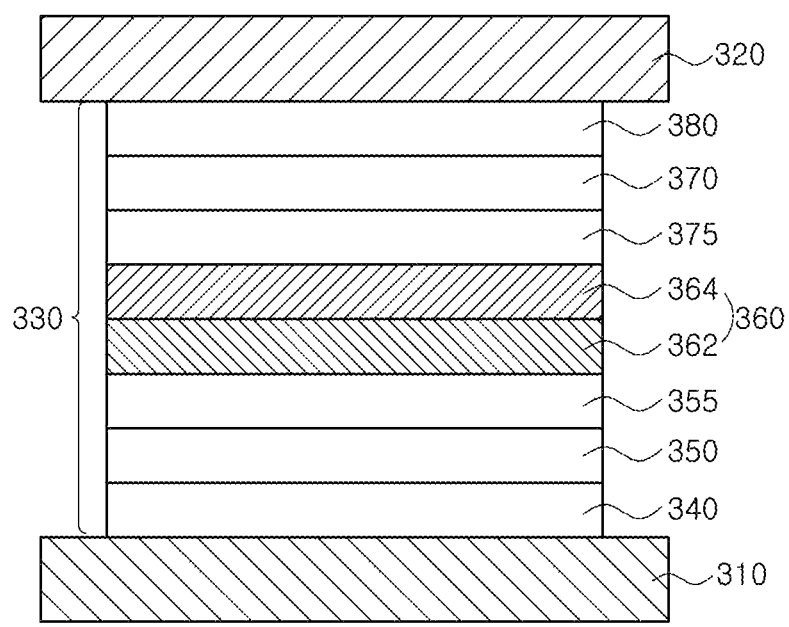
FIG. 8 is a schematic cross-sectional view illustrating an organic light-emitting diode in accordance with another exemplary embodiment of the present disclosure.

The OLEDs in accordance with the previous embodiments have only single emitting material layer. Alternatively, an OLED in accordance with the present disclosure may include multiple-layered emitting material layer. FIG. 8 is a schematic cross-sectional view illustrating an organic light-emitting diode having a host, a delayed fluorescent material and an organic compound as a fluorescent dopant in a double-layered EML in accordance with another exemplary embodiment of the present disclosure.

As illustrated in FIG. 8, the OLED 300 in accordance with an exemplary fourth embodiment of the present disclosure include first and second electrodes 310 and 320 facing each other and an emitting layer 330 disposed between the first and second electrodes 310 and 320.

In one exemplary embodiment, the emitting layer 330 include an HIL 340, an HTL 350, and EML 360, an ETL 370 and an EIL 380 each of which is laminated sequentially over the first electrode 310. In addition, the emitting layer 330 may include an EBL 355 as a first exciton blocking layer disposed between the HTL 350 and the EML 360, and/or an HBL 375 as a second exciton blocking layer disposed between the EML 360 and the ETL 370.

In this embodiment, the EML 360 includes a first EML (EML1) 362 disposed between the EBL 355 and the HBL 375 and a second EML (EML2) 364 disposed between the EML1 362 and the HBL 375. One of the EML1 362 and the EML2 364 includes the organic compound represented by any one of Chemical Formulae 1 to 4 as a fluorescent dopant (first fluorescent dopant, F dopant), and the other of the EML1 362 and the EML2 364 includes a delayed fluorescent dopant (T dopant). Hereinafter, the EML 360, where the EML1 362 includes the fluorescent dopant and the EML2 364 includes the delayed fluorescent dopant, will be explained.

The EML1 362 may include a first host and a first fluorescent dopant that is the organic compound represented by any one of Chemical Formulae 1 to 4. While the organic compound represented by any one Chemical Formulae 1 to 4 has a narrow FWHM and therefore, and can enhance its color purity, its luminous efficiency is limited because its triplet excitons cannot be involved in the emission process.

In contrast, the EML2 364 may include a second host and the delayed fluorescent dopant. The delayed fluorescent dopant in the EML2 364 has little energy bandgap between the excited state triplet energy level $T_1^{TD}$ and the excited state singlet energy level $S_1^{TD}$, i.e. equal to or less than about 0.5 eV, and its exited state triplet energy can be transferred to its excited state singlet energy by RISC. While the delayed fluorescent dopant has high quantum efficiency, it shows poor color purity owing to its wide FWHM.

However, in this exemplary embodiment, both the singlet energy and the triplet energy of the delayed fluorescent dopant in EML2 364 can be transferred to the first fluorescent dopant comprised in the EML1 362 disposed adjacently to the EML2 364 by FRET (Forster resonance energy transfer) that transfers energy non-radially through electrical fields by dipole-dipole interactions. Accordingly, the ultimate emission is done at the first fluorescent dopant in the EML1 362.

Figure 9:
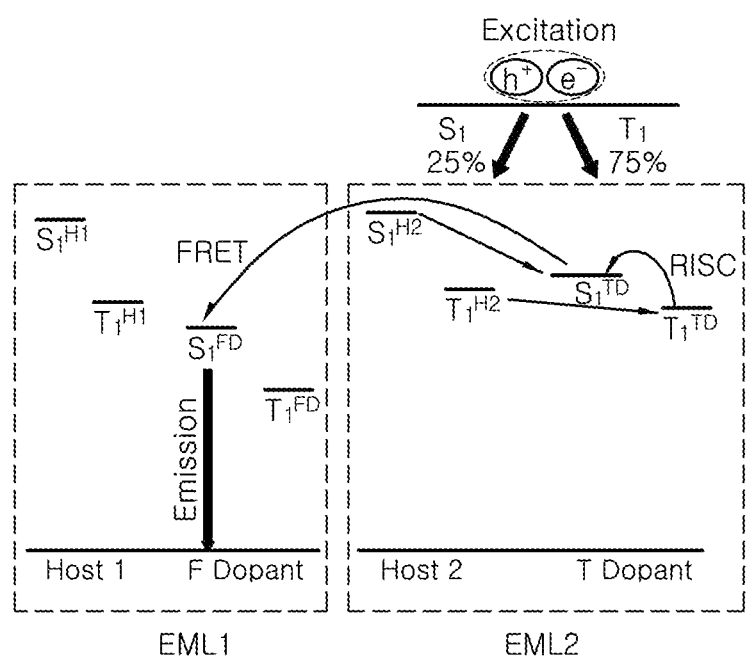
FIG. 9 is a schematic diagram illustrating a luminous mechanism by an energy level bandgap among a host, a delayed fluorescent dopant and a fluorescent material in double-layered EML in accordance with another exemplary embodiment of the present disclosure.

In other words, the triplet energy of the delayed fluorescent dopant is converted to the singlet energy of the delayed fluorescent dopant in the EML2 364 by RISC, and the singlet energy of the delayed fluorescent dopant is transferred to the singlet energy of the first fluorescent dopant because the excited state singlet energy level $S_1^{TD}$ of the delayed fluorescent dopant is higher than the excited state singlet energy level $S_1^{FD}$ of the first fluorescent dopant (See, FIG. 9). The first fluorescent dopant in the EML1 362 can emit light both using the singlet energy and the triplet energy. Therefore, the OLED 300 enhance luminous efficiency and color purity owing to the narrow FWHM of the first fluorescent dopant.

In this case, the delayed fluorescent dopant only acts as transferring energy to the first fluorescent dopant. The EML2 364 including the delayed fluorescent dopant is not involved in the ultimate emission process, while the EML1 362 including the first fluorescent dopant emits light.

Each of the EML1 362 and the EML2 364 includes the first host and the second host, respectively. For example, each of the first host and the second host may respectively be, but is not limited to, mCP-CN, CBP, mCBP, MCP, DPEPO, PPT, TmPyPB, PYD-2CZ, DCzDBT, DCzTPA, pCzB-2CN, mCzB-2CN, TPSO1, CCP, 4-(3-(triphenylen-2-yl)phenyl)dibenzo[b,d]thiophene, 9-(4-(9H-carbazol-9-yl)phenyl)-9H-3,9'-bicarbazole, 9-(3-(9H-carbazol-9-yl)phenyl)-9H-3,9'-bicarbazole and/or 9-(6-(9H-carbazol-9-yl)pyridin3-yl)-9H-3,9'-bicabazole. Particularly, each of the first host and the second host may be, but is not limited to, any one of H1 to H5 represented by Chemical Formula 5 above.

In addition, the delayed fluorescent dopant, which can be included in the EML2 364, may be, but is not limited to, Cz2BP, DcrTrZ, 4-DcrTrZ, 10-(4-(4,6-diphenyl-1,3,5-triazin-2-yl)phenyl)-10H-spiro[acridine-9,9'-xanthene], 2CzPN, 4CzIPN, 4CzPN, Px-VPN, TczTRZ and/or 32alC-TRZ). Particularly, the delayed fluorescent dopant may be, but is not limited to, any one of Chemical Formula 6 above.

In one exemplary embodiment, each of the first and second hosts may have more weight ratio than the first fluorescent dopant and the delayed fluorescent dopant in the EML1 362 and the EML2 364, respectively. In addition, the weight ratio of the delayed fluorescent dopant in the EML2 364 may be more than the weight ratio of the first fluorescent dopant in the EML1 362. In this case, it is possible to transfer enough energy from the delayed fluorescent dopant in the EML2 364 to the first fluorescent dopant in the EML1 362.

Now, energy level relationships among the materials in the EML 360, which including double-layered EMLs 362 and 364 in accordance with fourth embodiment of the present disclosure, will be explained. FIG. 9 is a schematic diagram illustrating luminous mechanism by energy level bandgap among a host, a delayed fluorescent dopant and a fluorescent material in a double-layered EML in accordance with another exemplary embodiment of the present disclosure. As illustrated in FIG. 9, an excited state singlet energy level $S_1^{H1}$ of the first host is higher than an excited state singlet energy level $S_1^{FD}$ of the fluorescent dopant in the EML1 362.

Also, each of an excited state singlet energy level $S_1^{H2}$ and an excited state triplet energy level $T_1^{H2}$ of the second host are higher than an excited state singlet energy level $S_1^{TD}$ and an excited state triplet energy level $T_1^{TD}$ of the delayed fluorescent dopant in the EML2 364, respectively. In addition, the excited state singlet energy level $S_1^{TD}$ of the delayed fluorescent dopant in the EML2 364 is higher than the excited state singlet energy level $S_1^{FD}$ of the fluorescent dopant in the EML1 362.

If the EML 360 does not satisfy the above-mentioned energy level conditions, there exists a quenching phenomenon at both the delayed fluorescent dopant and the fluorescent dopant and/or the energy cannot transfer to the fluorescent dopant from the delayed fluorescent dopant. As a result, the quantum efficiency of the OLED 300 may be reduced.

In one exemplary embodiment, the energy bandgap between the excited state singlet energy level $S_1^{TD}$ and the excited state triplet energy level $T_1^{TD}$ may be equal to or less than about 0.3 eV. In addition, an energy level bandgap ($|HOMO^H - HOMO^{TD}|$) between a Highest Occupied Molecular Orbital energy level ($HOMO^H$) of the first and/or second hosts and a Highest Occupied Molecular Orbital energy level ($HOMO^H$) of the delayed fluorescent dopant, or an energy level bandgap ($|LUMO^H - LUMO^{TD}|$) between a Lowest Unoccupied Molecular Orbital energy level (LUMO$^H$) of the first and/or second hosts and a Lowest Unoccupied Molecular Orbital energy level (LUMO$^{TD}$) of the first dopant may be equal to or less than about 0.5 eV.

In an alternatively exemplary embodiment, the first host, which is included in the EML1 362 together with the first fluorescent dopant, i.e. the organic compound represented by any one of Chemical Formulae 1 to 4, may be the same material as the EBL 355. In this case, the EML1 362 may have an electron blocking function as well as an emission function. In other words, the EML1 362 can act as a buffer layer for blocking electrons. In one embodiment, the EBL 355 may be omitted where the EML1 362 may be an electron blocking layer as well as an emitting material layer.

In another exemplary embodiment, the EML1 362 may include the second host and the delayed fluorescent dopant, while the EML2 364 may include the first host and the first fluorescent dopant that is the organic compound represented by any one of Chemical Formulae 1 to 4. In this embodiment, the first host in the EML2 364 may be the same material as the HBL 375. In this case, the EML2 364 may have a hole blocking function as well as an emission function. In other words, the EML2 364 can act as a buffer layer for blocking holes. In one embodiment, the HBL 375 may be omitted where the EML2 364 may be a hole blocking layer as well as an emitting material layer.

Figure 10:
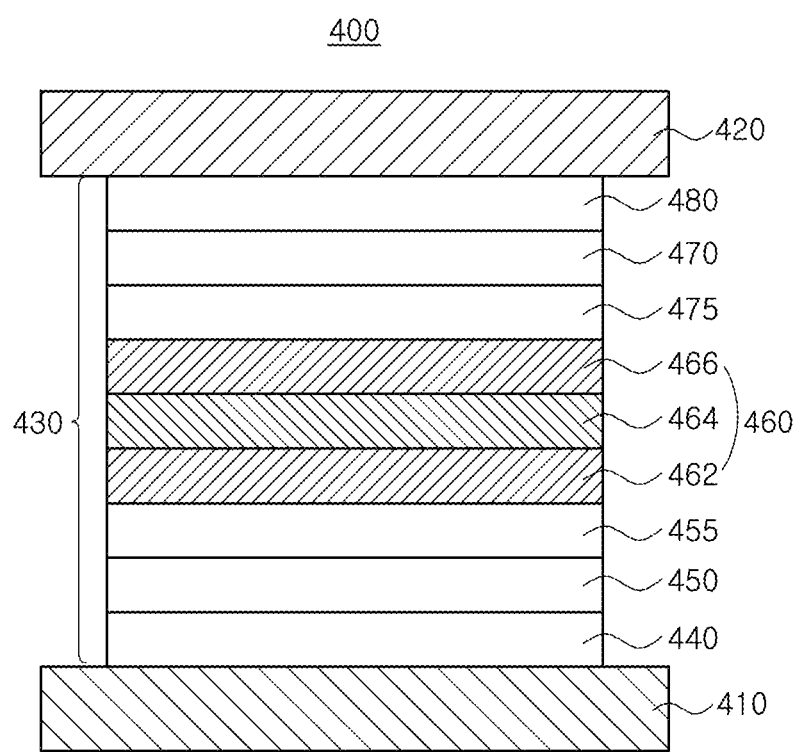
FIG. 10 is a schematic cross-sectional view illustrating an organic light-emitting diode in accordance with another exemplary embodiment of the present disclosure.

An OLED having three-layered EMLs will be explained. FIG. 10 is a schematic cross-sectional view of an organic light-emitting diode having a host, a delayed fluorescent material and an organic compound as a fluorescent dopant in a triple-layered EML in accordance with another exemplary embodiment of the present disclosure. As illustrated in FIG. 10, an OLED 400 in accordance with fifth embodiment of the present disclosure includes first and second electrodes 410 and 420 facing each other and an emitting layer 430 disposed between the first and second electrodes 410 and 420.

In one exemplary embodiment, the emitting layer 430 includes an HIL 440, an HTL 450, and EML 460, an ETL 470 and an EIL 480 each of which is laminated sequentially over the first electrode 410. In addition, the emitting layer 430 may include an EBL 455 as a first exciton blocking layer disposed between the HTL 450 and the EML 460, and/or an HBL 475 as a second exciton blocking layer disposed between the EML 460 and the ETL 470.

In this embodiment, the EML 460 includes a first EML (EML1) 462 disposed between the EBL 455 and the HBL 475, a second EML (EML2) 464 disposed between the EML1 462 and the HBL 475 and a third EML (EML3) 466 disposed between the EML2 464 and the HBL 475. Each of the EML1 462 and the EML3 466 includes a first fluorescent dopant (F dopant 1) and a second fluorescent dopant 2 (F dopant 2), respectively, and the second EML2 464 includes a delayed fluorescent dopant. For example, each of the first fluorescent dopant and the second fluorescent dopant may be the organic compound represented by any one of Chemical Formulae 1 to 4, respectively. In this case, an excited state singlet energy level $S_1^{TD}$ of the delayed fluorescent dopant in the EML2 464 may be higher than excited state energy levels $S_1^{FD1}$ and $S_1^{FD2}$ of the first and second fluorescent dopants each of which is included in the EML1 462 and EML3 466, respectively (See, FIG. 11). Each of the EML1 462, EML2 464 and EML3 466 further include a first host, a second host and a third host, respectively.

In accordance with this embodiment, both the singlet energy and the triplet energy of the delayed fluorescent dopant in EML2 464 can be transferred to the first and second fluorescent dopants each of which is included in the EML1 462 and EML3 466 disposed adjacently to the EML2 464 by FRET energy transfer mechanism. Accordingly, the ultimate emission is done both at the first and second fluorescent dopants in the EML1 462 and the EML3 466.

Figure 11:
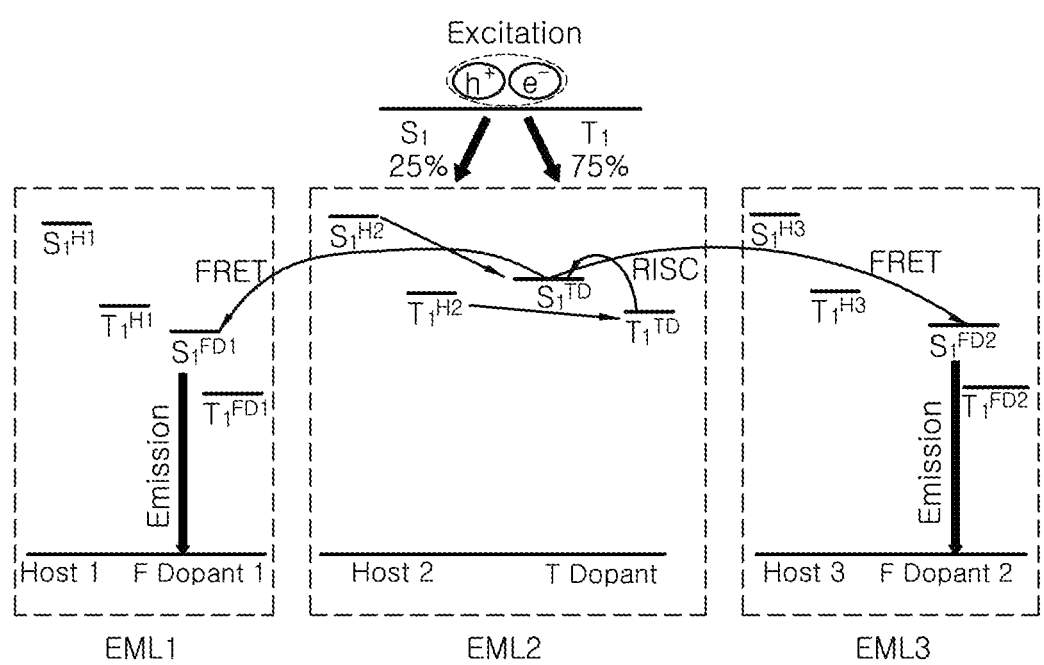
FIG. 11 is a schematic diagram illustrating a luminous mechanism by an energy level bandgap among a host, a delayed fluorescent dopant and a fluorescent material in a triple-layered EML in accordance with another exemplary embodiment of the present disclosure.

In other words, the triplet energy of the delayed fluorescent dopant is converted to the singlet energy of the delayed fluorescent dopant in the EML2 464 by RISC, and the singlet energy of the delayed fluorescent dopant is transferred to the singlet energy of the first and second fluorescent dopants because the excited state singlet energy level $S_1^{TD}$ of the delayed fluorescent dopant is higher than the excited state singlet energy levels $S_1^{FD1}$ and $S_1^{FD2}$ of the first and second fluorescent dopants (See, FIG. 11). The first and second fluorescent dopants in the EML1 462 and EML3 466 can emit light both using the singlet energy and the triplet energy. Therefore, the OLED 400 enhance its luminous efficiency and color purity owing to the narrow FWHM of the first and second fluorescent dopants.

In this case, the delayed fluorescent dopant only acts as transferring energy to the first and second fluorescent dopants. The EML2 464 including the delayed fluorescent dopant is not involved in the ultimate emission process, while both the EML1 462 including the first fluorescent dopant and the EML3 466 including the second fluorescent dopant emit light.

Each of the EML1 462, the EML2 464 and the EML3 466 includes the first host, the second host and the third host, respectively. For example, each of the first host, the second host and the third host may respectively be, but is not limited to, mCP-CN, CBP, mCBP, MCP, DPEPO, PPT, TmPyPB, PYD-2CZ, DCzDBT, DCzTPA, pCzB-2CN, mCzB-2CN, TPSO1, CCP, 4-(3-(triphenylen-2-yl)phenyl)dibenzo[b,d]thiophene, 9-(4-(9H-carbazol-9-yl)phenyl)-9H-3,9'-bicarbazole, 9-(3-(9H-carbazol-9-yl)phenyl)-9H-3,9'-bicarbazole and/or 9-(6-(9H-carbazol-9-yl)pyridin3-yl)-9H-3,9'-bicabazole. Particularly, each of the first host, the second host and the third host may be, but is not limited to, any one of H1 to H5 represented by Chemical Formula 5 above.

In addition, the delayed fluorescent dopant, which can be included in the EML2 464, may be, but is not limited to, Cz2BP, DcrTrZ, 4-DcrTrZ, 10-(4-(4,6-diphenyl-1,3,5-triazin-2-yl)phenyl)-10H-spiro[acridine-9,9'-xanthene], 2CzPN, 4CzIPN, 4CzPN, Px-VPN, TczTRZ and/or 32alC-TRZ). Particularly, the delayed fluorescent dopant may be, but is not limited to, any one of Chemical Formula 6 above.

In one exemplary embodiment, each of the first to third hosts may have more weight ratio than the first fluorescent dopant, the delayed fluorescent dopant and the second fluorescent dopant in the EML1 462, the EML2 464 and the EML3 466, respectively. In addition, the weight ratio of the delayed fluorescent dopant in the EML2 464 may be more than the weight ratio of the first fluorescent dopant in the EML1 462 and of the second fluorescent dopant in the EML3 464. In this case, it is possible to transfer enough energy from the delayed fluorescent dopant in the EML2 464 to the first fluorescent dopant in the EML1 462 and to the second fluorescent dopant in the EML3 466.

An energy level relationships among the materials in the EML 460 includes there two EMLs 462, 464 and 466 in accordance with fifth embodiment of the present disclosure will be explained. FIG. 11 is a schematic diagram illustrating luminous mechanism by energy level bandgap among a host, a delayed fluorescent dopant and a fluorescent material in a triple-layered EML in accordance with another exemplary embodiment of the present disclosure. As illustrated in FIG. 11, an excited state singlet energy level $S_1^{TD}$ of the first host is higher than an excited state singlet energy level $S_1^{FD1}$ of the first fluorescent dopant in the EML1 462. In addition, an excited state singlet energy level $S_1^{TD}$ of the third host is higher than an excited state singlet energy level $S_1^{FD2}$ of the second fluorescent dopant in the EML3 466.

Also, each of an excited state singlet energy level $S_1^{H2}$ and an excited state triplet energy level $T_1^{H2}$ of the second host are higher than an excited state singlet energy level $S_1^{TD}$ and an excited state triplet energy level $T_1^{TD}$ of the delayed fluorescent dopant in the EML2 464, respectively. In addition, each of an excited state triplet energy level $T_1^{H1}$ of the first host in the EML1 462 and an excited state triplet energy level $T_1^{H3}$ of the third host in the EML3 466 is higher than the excited state triplet energy level $T_1^{TD}$ of the delayed fluorescent dopant in the EML2 464. In addition, the excited state singlet energy level $S_1^{TD}$ of the delayed fluorescent dopant in the EML2 464 is higher than the excited state singlet energy levels $S_1^{FD1}$ and $S_1^{FD2}$ of the first and second fluorescent dopants in the EML1 462 and the EML3 466.

In one exemplary embodiment, the energy bandgap between the excited state singlet energy level $S_1^{TD}$ and the excited state triplet energy level $T_1^{TD}$ may be equal to or less than about 0.3 eV. In addition, an energy level bandgap (|HOMO$^H$-HOMO$^{TD}$|) between a Highest Occupied Molecular Orbital energy level (HOMO$^H$) of the first, second and/or third hosts and a Highest Occupied Molecular Orbital energy level (HOMO$^H$) of the delayed fluorescent dopant, or an energy level bandgap (|LUMO$^H$-LUMO$^{TD}$|) between a Lowest Unoccupied Molecular Orbital energy level (LUMO$^H$) of the first, second and/or third hosts and a Lowest Unoccupied Molecular Orbital energy level (LUMO$^{TD}$) of the first dopant may be equal to or less than about 0.5 eV.

In an alternatively exemplary embodiment, the first host, which is included in the EML1 462 together with the first fluorescent dopant, i.e., the organic compound represented by any one of Chemical Formulae 1 to 4, may be the same material as the EBL 455. In this case, the EML1 462 may have an electron blocking function as well as an emission function. In other words, the EML1 462 can act as a buffer layer for blocking electrons. In one embodiment, the EBL 455 may be omitted where the EML1 462 may be an electron blocking layer as well as an emitting material layer.

In another exemplary embodiment, the third host, which is included in the EML3 466 together with the second fluorescent dopant, i.e., the organic compound represented by any one of Chemical Formulae 1 to 4, may be the same material as the HBL 475. In this case, the EML3 466 may have a hole blocking function as well as an emission function. In other words, the EML3 466 can act as a buffer layer for blocking holes. In one embodiment, the HBL 475 may be omitted where the EML3 466 may be a hole blocking layer as well as an emitting material layer.

In still another exemplary embodiment, the first host in the EML1 462 may be the same material as the EBL 455 and the third host in the EML3 466 may be the same material as the HBL 475. In this embodiment, the EML1 462 may have an electron blocking function as well as an emission function, and the EML3 466 may have a hole blocking function as well as an emission function. In other words, each of the EML1 462 and the EML3 466 can act as a buffer layer for blocking electrons or hole, respectively. In one embodiment, the HBL 455 and the EBL 475 may be omitted where the EML1 462 may be an electron blocking layer as well as an emitting layer and the EML3 466 may be a hole blocking layer as well as an emitting material layer.

SYNTHESIS EXAMPLE 1

Synthesis of Compound 2

(1) Synthesis of Intermediate A-1 (2-(4-boropheyl)-1,4,5-triphenyl-1H-imidazole)

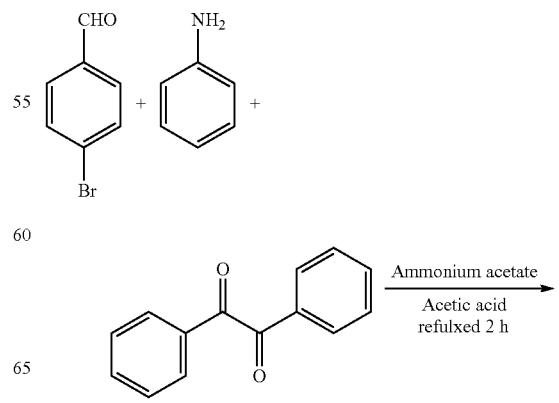

-continued

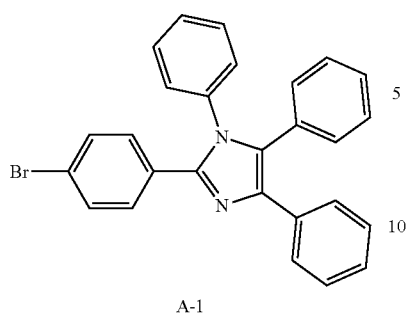

A-1

5.00 g (27.03 mmol) of 4-bromobenzaldehyde, 12.58 g (135.13 mmol) of aniline, 5.68 g (27.03 mmol) of benzil and 8.33 g (108.10 mmol) of ammonium acetate were placed in 500 mL 2-neck flask and dissolved in 250 mL of acetic acid. Then, the reaction mixture was refluxed and stirred for 3 hours. After the reaction was completed, precipitated sold was filter and washed with acetic acid/water (3:1) solution to give 9.15 g of white powder A-1 (yield: 75).

(2) Synthesis of Intermediate A-2 (1,4,5-triphenyl-2-(4-(4,4,5,5-tetramethyl-1,3,2-dioxaborolan-2-yl)phenyl)-1H-imdiazole)

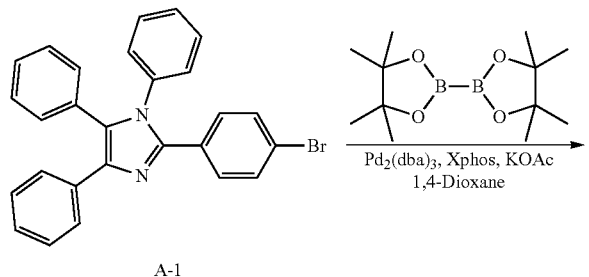

A-1

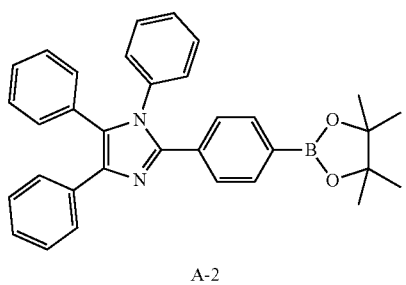

A-2

5.00 g (11.08 mmol) of intermediate A-1, 8.44 g (33.23 mmol) of bis(pinacolato)diboran, 0.30 g (0.33 mmol) of Pd2(dba)₃ (tris(dibenzylideneacetone)dipalladium(0)), 0.32 g (0.66 mmol) of XPhos (2-dicyclohexylphosphine-2',4',6'-triisopropylbiphenyl), 3.81 g (38.77 mmol) of KOAc (potassium acetate) were placed in 500 mL 2-neck flask and dissolved in 200 mL of 1,4-dioxane. Then, the reaction mixture was refluxed and stirred for 12 hours. After the reaction was completed, column chromatography was performed using hexane/ethyl acetate (10:1) as a developing solvent to give 4.80 g of solid A-2 (yield: 88.07%).

(3) Synthesis of Intermediate B-2 (4,4,5,5-tetramethyl-2-(spiro[benzo[d,e]anthracene-7,9'-fluoren]-9-yl)-1,3,2-dioxaborolane)

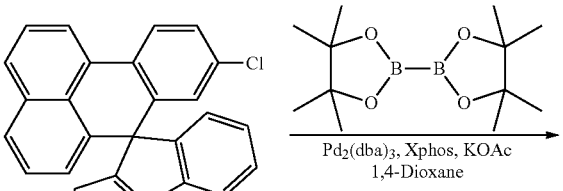

B-1

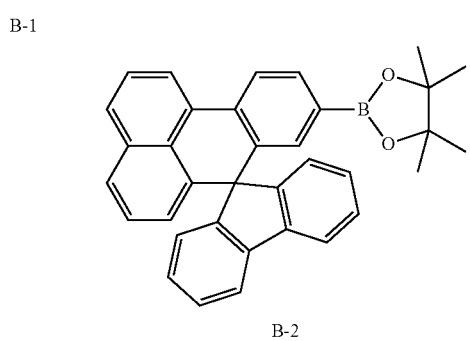

B-2

2.00 g (4.99 mmol) of compound B-1, 3.80 g (14.97 mmol) of bis(pinacolato)diboran, 0.14 g (0.15 mmol) of Pd2(dba)3, 0.14 g (0.30 mmol) of XPhos and 1.71 g (17.46 mmol) of KOAc were placed in 250 mL 2-neck flask and dissolved in 70 mL of 1,4-dioxane. Then, the reaction mixture was refluxed and stirred for 12 hours. After the reaction was completed, column chromatography was performed using hexane/ethyl acetate (10:1) as a developing solvent to give 2.1 g of solid B-2 (yield: 85.5%).

(3) Synthesis of Intermediate B-3 (Methyl-5-bromo-2-(spiro[benzo[d,e]anthracene-7,9'-fluoren]-9-yl-benzoate)

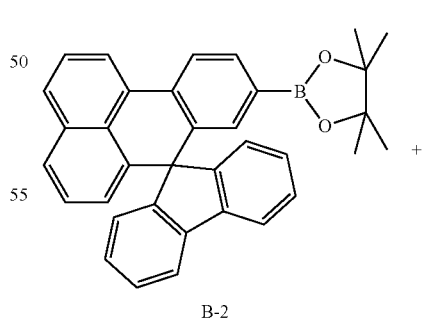

B-2

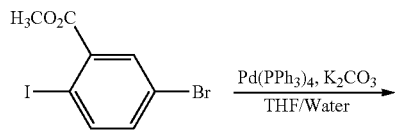

-continued

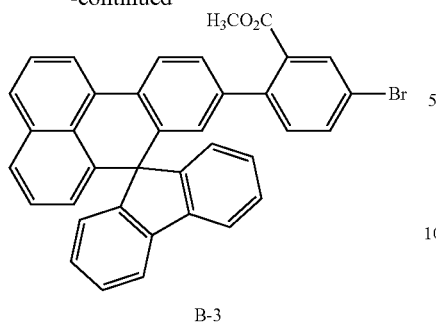

B-3

2.00 g (4.06 mmol) of intermediate B-2, 1.66 g (4.87 mmol) of methyl-5-bromo-2-iodobenzoate, 2.81 g (20.31 mmol) of $K_2CO_3$, 0.14 g (0.12 mmol) of $Pd(PPh_3)_4$ (tetrakis(triphenylphosphine)palladium(0)) were placed in 250 mL 2-neck flask and dissolved in 70 mL of a mixed solvent THF/water (3:1). Then, the reaction mixture was refluxed and stirred for 12 hours. After the reaction was completed, column chromatography was performed using methylene chloride (MC)/hexane (3:7) as developing solvent to give 1.8 g of solid B-3 (yield: 54.68%).

(5) Synthesis of Intermediate B-4 (2-(5-Chloro-2-(spiro[benzo[d,e]anthracene-7,9'-fluoren]-9-yl)phenyl)propan-2-ol)

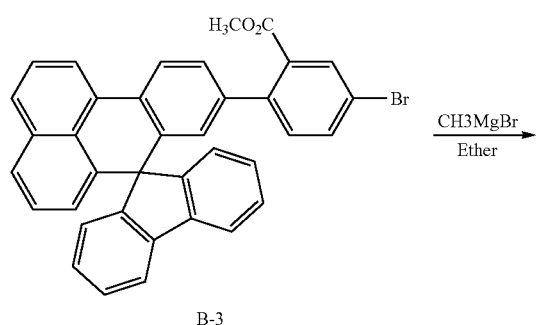

1.80 g (3.11 mmol) of intermediate B-3 was place in 250 mL 2-neck flask, dissolved in 70 mL of ether and cooled to 0° C. Then, 1.11 g (9.32 mmol, 3M) of $CH_3MgBr$ was added dropwise into the flask and was raised slowly to room temperature. After the reaction was completed, water is added and the resulting solid was filtered to give 1.75 g of intermediate B-4 (yield: 97.2%).

(6) Synthesis of Intermediate B-5 (11-Bromo-13,13,-dimethyl-13H-spiro[benzo[f,g]indeno[1,2-b]anthracene-7,9'-fluorene])

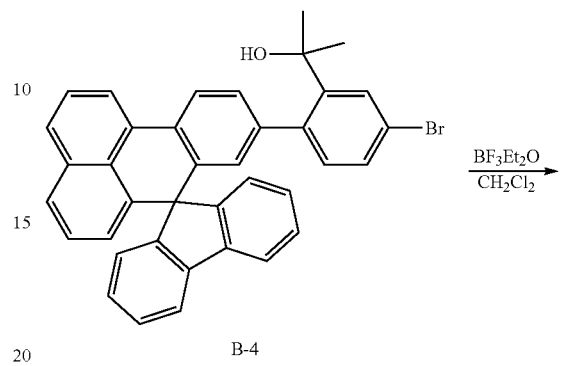

B-4

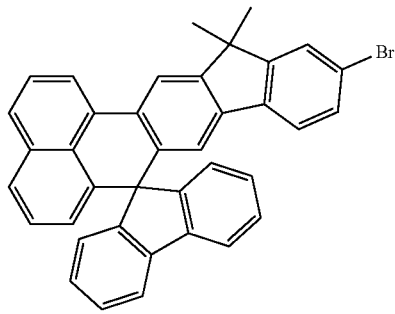

B-5

1.80 g (3.11 mmol) of intermediate B-4 was placed in 250 mL 2-neck flask, dissolved in 70 mL of ether and cooled to 0° C. Then, 0.22 g (1.55 mmol) of $BF_3Et_2O$ was added dropwise into the flask, was raised slowly to room temperature, and stirred for 5 hours. After the reaction was completed, column chromatography was performed using MC/hexane as a developing solvent to give 1.0 g of solid B-5 (yield: 57.34%).

(7) Synthesis of Compound 2 (2-4(13,13-dimethyl-13H-spiro[benzo[f,g]indeno[1,2-b]anthracene-7,9'-fluoren]-11-yl)phenyl-1,4,5-triphenyl-1H-imidazole)

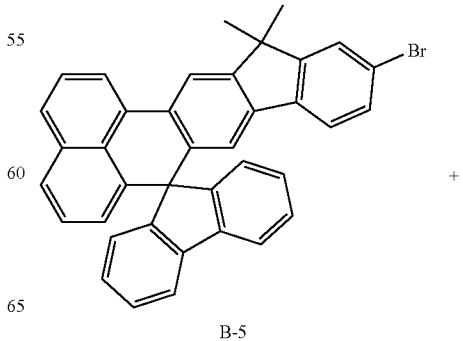

B-5

+

-continued

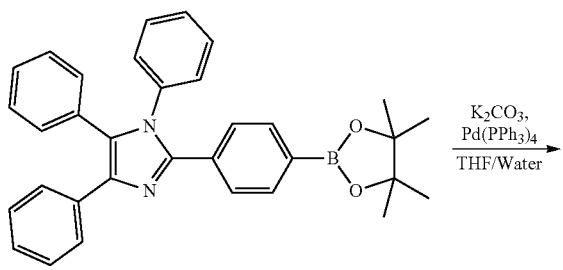

A-2

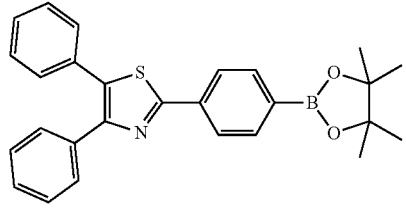

C-1

3.30 g (8.41 mmol) of 2-(4-bromophenyl)-4,5-diphenylthiazole, 6.41 g (25.24 mmol) of bis(pinacolato)diboran, 0.23 g (0.25 mmol) of $Pd_2(dba)_3$, 0.24 g (0.50 mmol) of XPhos and 2.89 g (29.44 mmol) of KOAc were placed in 500 mL 2-neck flask and dissolved 80 mL of 1,4-dioxane. Then, the reaction mixture was refluxed and stirred for 12 hours. After the reaction was completed, column chromatograph using hexane/ethyl acetate (10:1) as a developing solvent to give 2.72 g of solid C-1 (yield: 73.5%).

(2) Synthesis of Compound 3 (2-(4-(13,13-Dimethyl-13H-spiro[benzo[f,g]indeno[1,2-b]anthracene-7,9'-fluoren]-11-yl)phenyl)-4,5-diphenylthiazole)

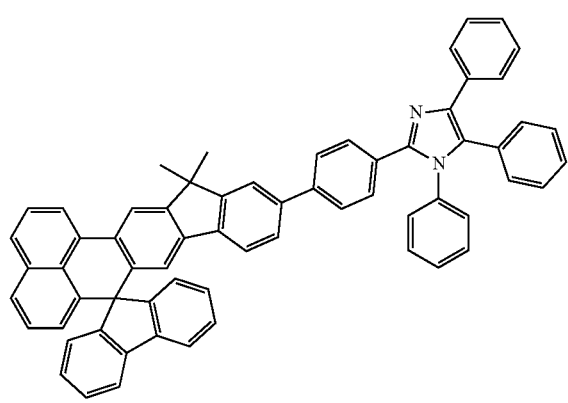

compound 2

1.00 g (1.78 mmol) of intermediate B-5, 1.07 g (2.14 mmol) of intermediate A-2, 1.23 g (8.90 mmol) of $K_2CO_3$ and 0.06 g (0.05 mmol) of $Pd(PPh_3)_4$ were placed in 250 mL 2-neck flaks and dissolved in 80 mL of a mixed solution THF/water (3:1). Then, the reaction mixture was refluxed and stirred for 12 hours. After the reaction was completed, column chromatograph was performed using MC/hexane (3:1) as a developing solvent to give 0.7 g of solid compound 2 (yield: 46.0%).

SYNTHESIS EXAMPLE 2

Synthesis of Compound 3

(1) Synthesis of Intermediate C-1 (4,5-Diphenyl-2-(4-(4,4,5,5-tetramethyl-1,3,2-dioxaborolan-2-yl)phenyl)thiazole)

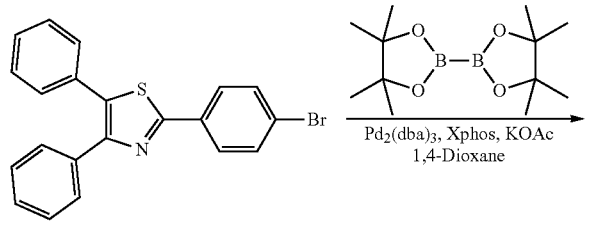

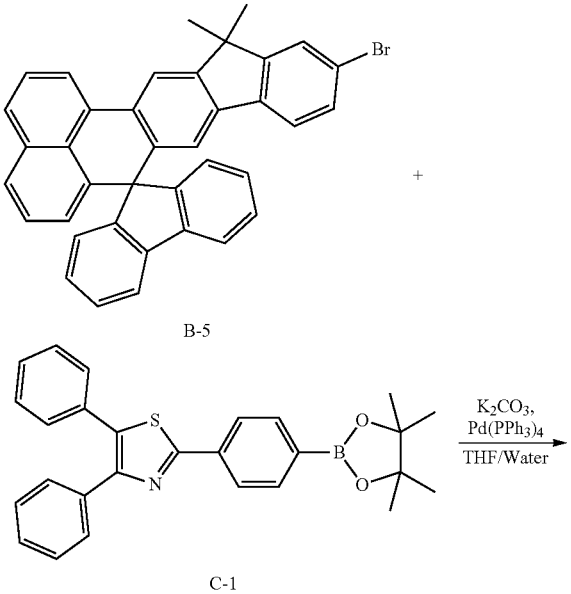

B-5

+

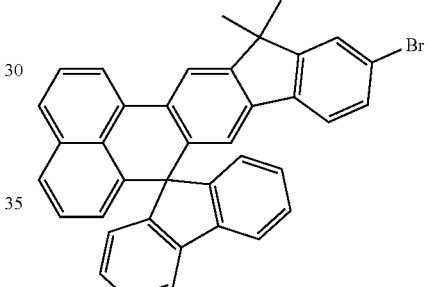

C-1

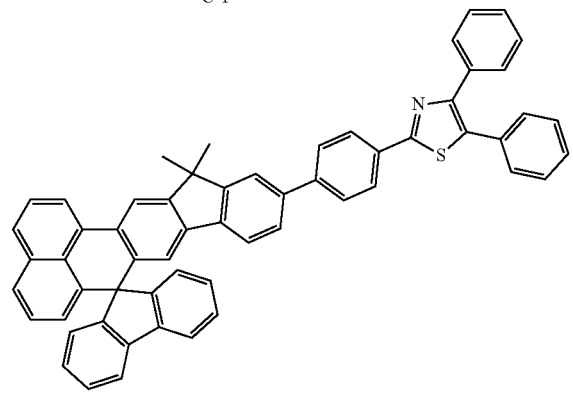

compound 3

1.00 g (1.78 mmol) of intermediate B-5, 0.94 g (2.14 mmol) of intermediated C-1, 1.23 g (8.90 mmol) of K₂CO₃ and 0.06 g (0.05 mmol) of Pd(PPh₃)₄ were placed in 250 mL 2-neck flask and dissolved in 80 mL of a mixed solution THF/water (3:1). Then, the reaction mixture was refluxed and stirred for 12 hours. After the reaction was completed, column chromatograph was performed using MC/hexane (2:1) as a developing solvent to give 1.0 g of solid compound 3 (yield: 70.7%).

SYNTHESIS EXAMPLE 3

Synthesis of Compound 5

(1) Synthesis of Intermediate E-2 (3-Bromo-13,13-dimethyl-13H-spiro[benzo[f,g]indeno[1,2-b]anthracene-7,9'-fluorene])

(2) Synthesis of Compound 5 (2-(4-(13,13-Dimethyl-13H-spiro[benzo[f,g]indeno[1,2-b]anthracene-7,9'-fluoren]3-yl)phenyl)-1,4,5-triphenyl-1H-imidazole

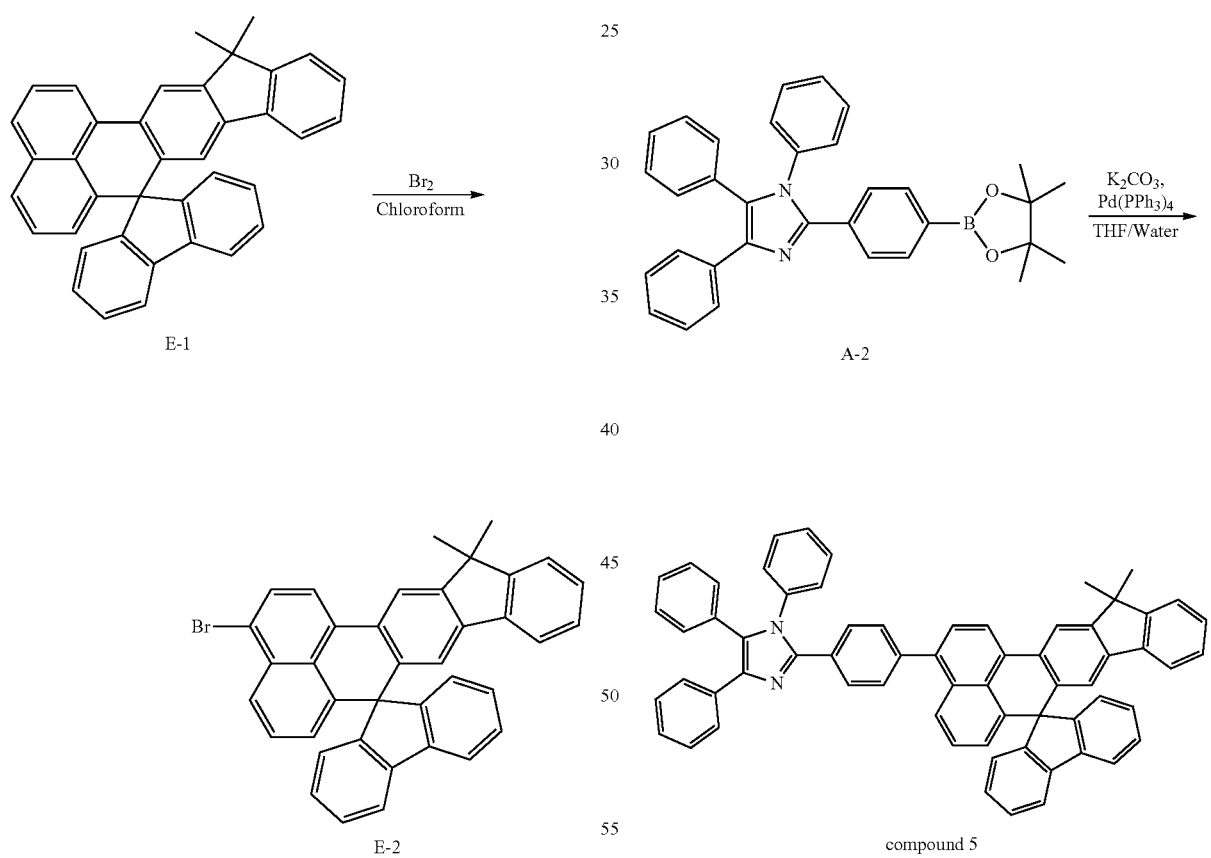

0.05 g (1.04 mmol) of compound E-1 was placed in 250 mL 2-neck flask, dissolved in 50 mL of chloroform and 0.17 g (0.055 mmol) of bromine was added slowly into the flask. Then, the reaction mixture was stirred at room temperature for 24 hours. After the reaction was completed, solvent was dried and column chromatography was performed using MC/hexane (1:9) as a developing solvent to give 0.50 g of white solid E-2 (yield: 85.9%).

1.00 g (1.78 mmol) of intermediate E-2, 1.07 g (2.14 mmol) of intermediate A-2, 1.23 g (8.90 mmol) of K₂CO₃ and 0.06 g (0.05 mmol) of Pd(PPh₃)₄ were placed in 250 mL 2-neck flask and dissolved in 80 mL of a mixed solution THF/water (3:1). Then, the reaction mixture was refluxed and stirred for 12 hours. After the reaction was completed, column chromatograph was performed using MC/hexane (2:1) as a developing solvent to give 1.3 g of solid compound 5 (yield: 85.5%).

SYNTHESIS EXAMPLE 4

Synthesis of Compound 6

Synthesis of Compound 6 (2-(4-(13,13-Dimethyl-13H-spiro[benzo][f,g]indeno[1,2-b]anthracene-7,9'-fluoren)phenyl)-4,5-diphenylthiazole

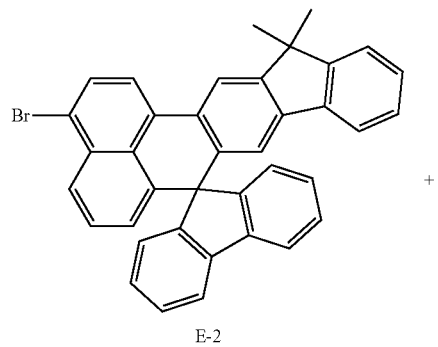

E-2

SYNTHESIS EXAMPLE 5

Synthesis of Compound 7

Synthesis of Compound 7 (N,N,13'-triphenyl-13'H-spiro[fluorene-9,7'-phenaeno[1,2-b]carbazole]-10'-amine

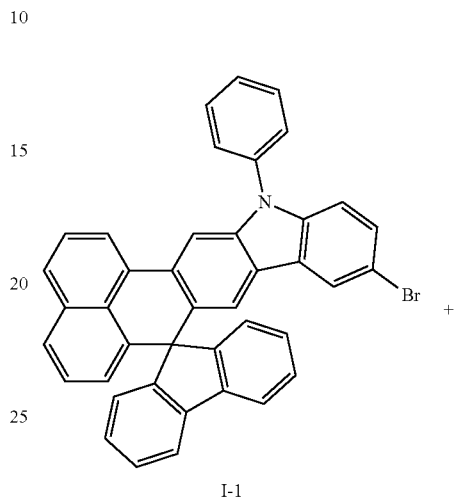

I-1

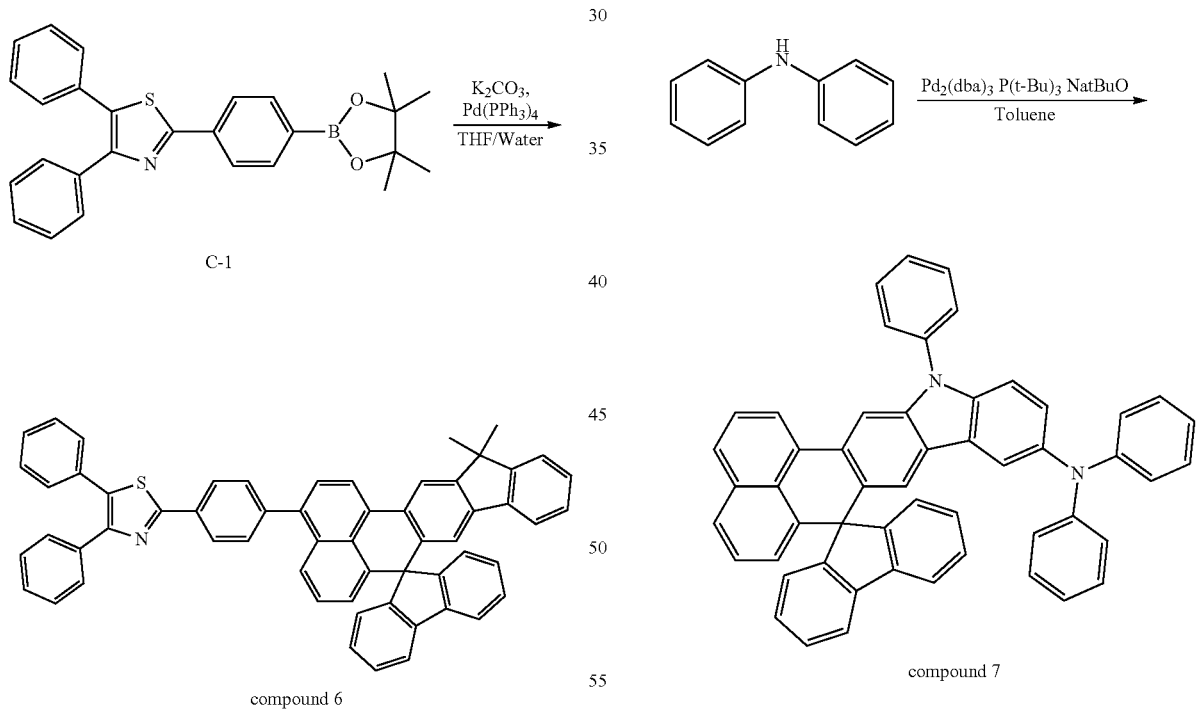

1.15 g (2.05 mmol) of intermediate E-2, 1.08 g (2.46 mmol) of intermediate C-1, 1.42 g (10.24 mmol) of $K_2CO_3$ and 0.07 g (0.06 mmol) of Pd(PPh$_3$)$_4$ were placed in 250 mL 2-neck flask and dissolved in 120 mL of a mixed solution THF/water (3:1). Then, the reaction mixture was refluxed and stirred for 12 hours. After the reaction was completed, column chromatograph was performed using MC/hexane (1:1) as a developing solvent to give 1.2 g of solid compound 6 (yield: 73.7%).

1.2 g (1.97 mmol) of compound I-1, 0.40 g (2.36 mmol) of diphenylamine, 0.05 g (0.06 mmol) of Pd$_2$(dba)$_3$, 0.01 g (0.06 mmol) of P(t-Bu)$_3$ (tri-tert-butylphosphine), 0.57 g (5.90 mmol) of NatBuO (sodium tert-butoxide) were placed in 250 mL 2-neck flask and dissolved in 100 mL of toluene. Then, the reaction mixture was refluxed and stirred for 12 hours. After the reaction was completed, column chromatography was performed using MC/hexane (3:7) as a developing solvent to give 0.7 g of solid compound 7 (yield: 51.0%).

SYNTHESIS EXAMPLE 6

Synthesis of Compound 8

Synthesis of Compound 8 (13'-Phenyl-10'-(4-(1,4,5-triphenyl-1H-imidazol-2-yl)phenyl)-13'H-spiro[fluorene-9,7'-phenaleno[1,2-b]carbazole

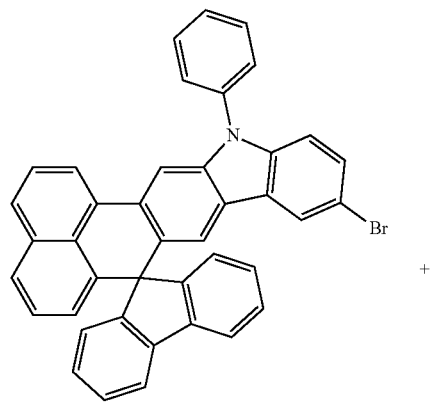

I-1

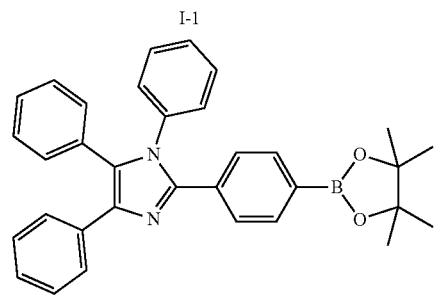

A-2 compound 8

1.10 g (1.80 mmol) of compound I-1, 1.08 g (2.16 mmol) of intermediate A-2, 1.25 g (9.01 mmol) of $K_2CO_3$ and 0.06 g (0.05 mmol) of $Pd(PPh_3)_4$ were placed in 250 mL 2-neck flask and dissolved in 80 mL of a mixed solution THF/water (3:1). Then, the reaction mixture was refluxed and stirred for 12 hours. After the reaction was completed, column chromatography was performed using MC/hexane (3:7) as a developing solvent to give 1.00 g of solid compound 8 (yield: 65.1%).

SYNTHESIS EXAMPLE 7

Synthesis of Compound 13

Synthesis of Compound 13 (N,N-Diphenylspiro[benzo[8,9]anthrax[2,3-b]benzofuran-7,9'-fluoren]-11-amine

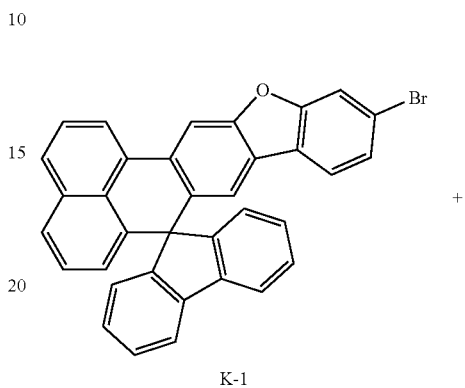

K-1

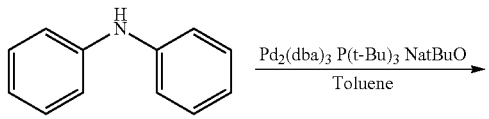

compound 13

1.5 g (2.80 mmol) of compound K-1, 0.57 g (3.36 mmol) of diphenylamine, 0.08 g (0.08 mmol) of $Pd_2(dba)_3$, 0.02 g (0.08 mmol) of $P(t-Bu)_3$ and 0.81 g (8.40 mmol) of NatBuO were placed in 250 mL 2-neck flask and dissolved in 100 mL of toluene. Then, the reaction mixture was refluxed and stirred for 12 hours. After the reaction was completed, column chromatograph was performed using MC/hexane (3:7) as a developing solution to give 1.2 g of solid compound 13 (yield: 62.3%).

SYNTHESIS EXAMPLE 8

Synthesis of Compound 19

Synthesis of Compound 19 (N,N,13'-Triphenyl-13'H-spiro[fluorene-9,7'-phenaleno[1,2-b]carbazole]-10'-amine

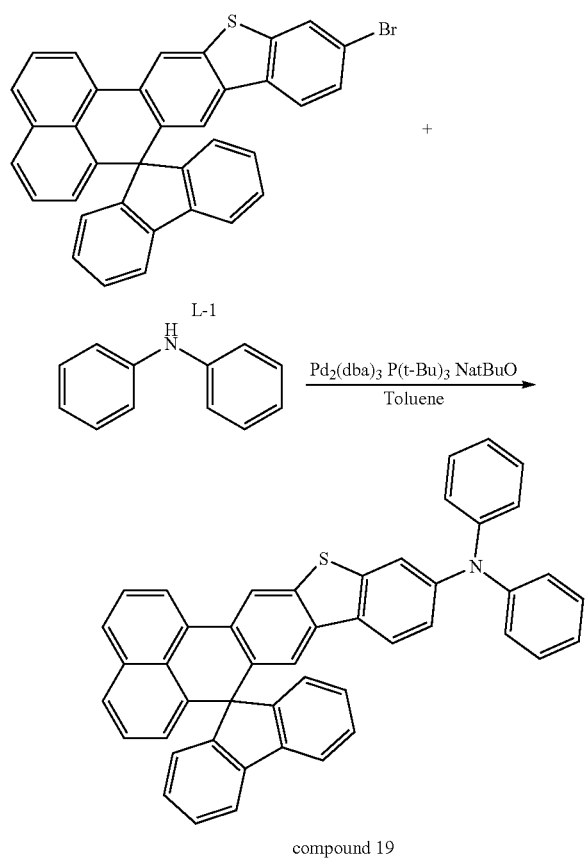

compound 19

1.1 g (1.99 mmol) of compound L-1, 0.41 g (2.30 mmol) of diphenylamine, 0.05 g (0.06 mmol) of $Pd_2(dba)_3$, 0.01 g (0.06 mmol) of $P(t-Bu)_3$ and 0.58 g (5.98 mmol) of NatBuO were placed in 250 mL 2-neck flask and dissolved in 100 mL of toluene. Then, the reaction mixture was refluxed and stirred for 12 hours. After the reaction was completed, column chromatograph was performed using MC/hexane (3:7) as a developing solution to give 0.8 g of solid compound 19 (yield; 58.3%).

EXPERIMENTAL EXAMPLE 1

FWHM Measurement of Organic Compounds

The FWHM (full width at half maximum) of the compound 2, compound 3, compound 5, compound 6, compound 7 and compound 8 synthesized respectively in the Synthesis Examples 1 to 6 were measured. Also, the FWHM of a delayed fluorescent material, i.e. 4CzIPN was measured for the comparison. The measurement results are shown in Table 1 below. As indicated in Table 1, all the organic compounds synthesized in the Synthesis Examples had a narrower FWHM than that of 4CzIPN, and were expected to enhance their color purity.

TABLE 1

Luminous FWHM of Organic Compound

| Sample | FWHM (nm) |
| --- | --- |
| 4CzIPN | 85 |
| Compound 2 | 54 |
| Compound 3 | 51 |
| Compound 5 | 65 |
| Compound 6 | 70 |
| Compound 7 | 71 |
| Compound 8 | 68 |

EXAMPLE 1

Manufacture of Organic Light-Emitting Diode (OLED)

An organic light-emitting diode was manufactured using Compound 2 synthesized in the Synthesis Example 1 as a dopant in an emitting material layer (EML). A glass substrate, to which ITO electrode (including a reflective plate) were attached and which has a size of 40 nm×40 nm×0.5 mm, was washed by ultra-sonication using isopropyl alcohol, acetone and DI (distilled water) as a cleaning solvent for 5 minutes and dried in an oven at 100° C. After cleaning the substrate, the substrate was treated $O_2$ plasma for 2 minutes and was transferred to a vacuum chamber for depositing emitting layer. Subsequently, an emitting layer and a cathode were deposited as the following order: A hole injection layer (HIL) (HAT-CN; 7 nm); a hole transport layer (HTL) (NPB, 55 nm); a electron blocking layer (EBL) (mCBP; 10 nm); an emitting material layer (EML) (4-(3-(triphenylen-2-yl)phenyl)dibenzo[b,d]thiophene: Compound 2 (95:5 by weight); 25 nm); a hole blocking layer (HBL) (B3PYMPM; 10 nm); an electron transport layer (ETL) (TPBi; 20 nm); an electron injection layer (EIL) (LiF); and a cathode (Al).

And then, cappling layer (CPL) was deposited over the cathode and the device was encapsulated by glass. After deposition of emissive layer and the cathode, the OLED was transferred from the deposition chamber to a dry box for film formation, followed by encapsulation using UV-curable epoxy and moisture getter. The manufacture organic light-emitting diode had an emission area of 9 $mm^2$.

EXAMPLES 2 to 6

Manufacture of OLED

An organic light-emitting diode was manufactured as the same process and the same materials as in Example 1, except that Compound 3 (Example 2) synthesized in the Synthesis Example 2, Compound 5 (Example 3) synthesized in the Synthesis Example 3, Compound 6 (Example 4) synthesized in the Synthesis Example 4, Compound 7 (Example 5) synthesized in the Synthesis Example 5 and Compound 8 (Example 6) synthesized in the Synthesis Example 6 was used as the dopant in the EML instead of the Compound 2.

COMPARATIVE EXAMPLE

Manufacture of OLED

An organic light-emitting diode was manufactured as the same process and the same materials as in Example 1, except that the following compound was used as the dopant instead of Compound 1.

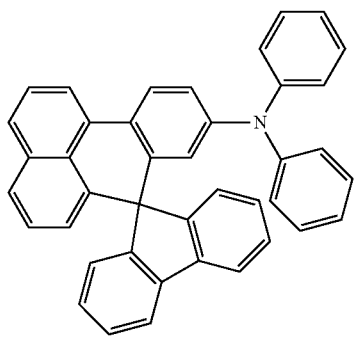 [SMILES: c1ccc(N(c2ccccc2)c2ccc3c(c2)C2(c4ccccc4-c4ccccc42)c2cccc4cccc-3c24)cc1]

EXPERIMENTAL EXAMPLE 2

Measurement of Luminous Properties of OLED

Each of the organic light-emitting diodes manufactured by Examples 1 to 6 and Comparative Example was connected to an external power source, and luminous properties of all the diodes were evaluated using a constant current source (KEITHLEY) and a photometer PR650 at room temperature. In particular, driving voltage (V), current efficiency (Cd/A), power efficiency (lm/W), external quantum efficiency (EQE; %), and color coordinates at a current density of 10 mA/cm$^2$ for a luminescence wavelength of the light-emitting diodes of Examples 1 to 6 and Comparative Example were measured. The results thereof are shown in the following Table 2.

TABLE 2

| Sample | V | cd/A | lm/W | EQE (%) | CIEx | CIEy |
|---|---|---|---|---|---|---|
| Comparative Example | 5.23 | 2.44 | 1.47 | 3.32 | 0.13 | 0.08 |
| Example 1 | 3.72 | 7.16 | 6.05 | 5.33 | 0.1538 | 0.1866 |
| Example 2 | 3.99 | 7.56 | 5.96 | 5.37 | 0.157 | 0.201 |
| Example 3 | 3.81 | 6.53 | 5.38 | 5.07 | 0.1538 | 0.1761 |
| Example 4 | 3.55 | 7.45 | 6.60 | 5.54 | 0.1528 | 0.1883 |
| Example 5 | 4.74 | 5.30 | 3.51 | 3.95 | 0.156 | 0.184 |
| Example 6 | 4.48 | 10.77 | 7.55 | 6.54 | 0.167 | 0.255 |

As indicated in Table 2, compared to the OLED using 4CzIPN as the dopant in the Comparative Example, the OLED using the organic compounds of the present disclosure as the dopant in Examples 1 to 6 has lowered the driving voltage maximally by 32.1%. In addition, compared to the OLED using 4CzIPN as the dopant in the Comparative Example, the OLED using the organic compounds of the present disclosure as the dopant in Examples 1 to 6 has enhanced current efficiency maximally by 341.3%, power efficiency maximally by 413.6% and external quantum efficiency maximally by 97.0%. In addition, the OLED using the organic compounds as the dopant can implement high color purity of cyan color as indicate by the color coordinates.

From these results, it was confirmed that an organic light-emitting diode and an organic light-emitting device such as an organic light-emitting display device and an organic lighting device can lower their driving voltages and enhance significantly their luminous efficiency by applying the organic compound of the present disclosure into the emitting layer.

While the present disclosure has been described with reference to exemplary embodiments and examples, these embodiments and examples are not intended to limit the scope of the present disclosure. Rather, it will be apparent to those skilled in the art that various modifications and variations can be made in the present disclosure without departing from the spirit or scope of the invention. Thus, it is intended that the present disclosure cover the modifications and variations of the present disclosure provided they come within the scope of the appended claims and their equivalents.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An organic compound represented by the following Chemical Formula 1:

Chemical Formula 1

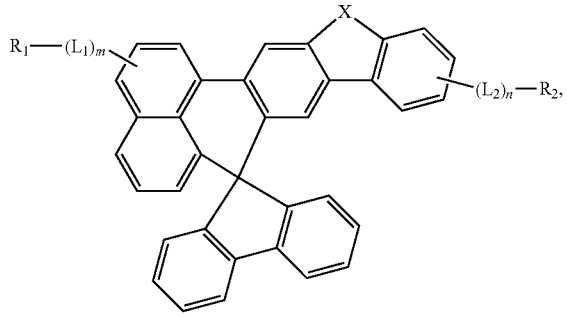

wherein each of $R_1$ and $R_2$ is independently selected from the group consisting of hydrogen, deuterium, tritium, amino group unsubstituted or substituted with a $C_4$-$C_{30}$ aromatic or heteroaromatic group, a $C_6$-$C_{30}$ aryl group unsubstituted or substituted with a $C_4$-$C_{30}$ aromatic or heteroaromatic group, a $C_4$-$C_{30}$ heteroaryl group unsubstituted or substituted with a $C_4$-$C_{30}$ aromatic or heteroaromatic group, a $C_6$-$C_{30}$ aralkyl group unsubstituted or substituted with a $C_4$-$C_{30}$ aromatic or heteroaromatic group, a $C_4$-$C_{30}$ heteroaralkyl group unsubstituted or substituted with a $C_4$-$C_{30}$ aromatic or heteroaromatic group, a $C_6$-$C_{30}$ aryloxyl group unsubstituted or substituted with a $C_4$-$C_{30}$ aromatic or heteroaromatic group and a $C_4$-$C_{30}$ heteroaryloxyl group unsubstituted or substituted with a $C_4$-$C_{30}$ aromatic or heteroaromatic group, and at least one of $R_1$ and $R_2$ is not hydrogen, deuterium and tritium, wherein $R_2$ is a $C_6$-$C_{30}$ aryl group unsubstituted or substituted with a $C_4$-$C_{30}$ aromatic or heteroaromatic group, a $C_6$-$C_{30}$ aralkyl group unsubstituted or substituted with a $C_4$-$C_{30}$ aromatic or heteroaromatic group, a $C_6$-$C_{30}$ aryloxyl group unsubstituted or substituted with a $C_4$-$C_{30}$ aromatic or heteroaromatic group, an imidazolyl group unsubstituted or substituted with a $C_4$-$C_{30}$ aromatic or heteroaromatic group or a thiazolyl group unsubstituted or substituted with a $C_4$-$C_{30}$ aromatic or heteroaromatic group when X is $NR_5$, wherein each of $L_1$ and $L_2$ is independently selected from the group consisting of a $C_6$-$C_{30}$ arylene group unsubstituted or substituted with a $C_4$-$C_{30}$ aromatic or heteroaromatic group, a $C_4$-$C_{30}$ heteroarylene group unsubstituted or substituted with a $C_4$-$C_{30}$ aromatic or heteroaromatic group, a $C_6$-$C_{30}$ aralkylene group unsubstituted or substituted with a $C_4$-$C_{30}$ aromatic or heteroaromatic group, a $C_4$-$C_{30}$ heteroaralkylene group unsubstituted or substituted with a $C_4$-$C_{30}$ aromatic or heteroaromatic group, a $C_6$-$C_{30}$ aryloxylene group unsubstituted or substituted with a $C_4$-$C_{30}$ aromatic or heteroaromatic group and a $C_4$-$C_{30}$ heteroaryloxylene group unsubstituted or substituted with a $C_4$-$C_{30}$ aromatic or heteroaromatic group, wherein $L_2$ is selected from the group consisting of a $C_6$-$C_{30}$ arylene group unsubstituted or substituted with a $C_4$-$C_{30}$ aromatic or heteroaromatic group, a $C_6$-$C_{30}$ aralkylene group unsubstituted or substituted with a $C_4$-$C_{30}$ aromatic or heteroaromatic group and a $C_6$-$C_{30}$ aryloxylene group unsubstituted or substituted with a $C_4$-$C_{30}$ aromatic or heteroaromatic group when X is $NR_5$, and each of m and n is independently 0 (zero) or 1, and wherein X is $CR_3R_4$, $NR_5$, O or S, and each of $R_3$ to $R_5$ is independently selected from the group consisting of hydrogen, a linear or branched $C_1$-$C_{20}$ alkyl group, a $C_6$-$C_{30}$ aryl group unsubstituted or substituted with a $C_4$-$C_{30}$ aromatic or heteroaromatic group, a $C_4$-$C_{30}$ heteroaryl group unsubstituted or substituted with a $C_4$-$C_{30}$ aromatic or heteroaromatic group, a $C_6$-$C_{30}$ aralkyl group unsubstituted or substituted with a $C_4$-$C_{30}$ aromatic or heteroaromatic group, a $C_4$-$C_{30}$ heteroaralkyl group unsubstituted or substituted with a $C_4$-$C_{30}$ aromatic or heteroaromatic group, a $C_6$-$C_{30}$ aryloxyl group unsubstituted or substituted with a $C_4$-$C_{30}$ aromatic or heteroaromatic group, a $C_4$-$C_{30}$ heteroaryloxyl group unsubstituted or substituted with a $C_4$-$C_{30}$ aromatic or heteroaromatic group, a $C_6$-$C_{30}$ arylamino group unsubstituted or substituted with a $C_4$-$C_{30}$ aromatic or heteroaromatic group and a $C_4$-$C_{30}$ heteroaryl amino group unsubstituted or substituted with a $C_4$-$C_{30}$ aromatic or heteroaromatic group.

2. The organic compound of claim 1, wherein the organic compound has the following structure of Chemical Formula 2:

Chemical Formula 2

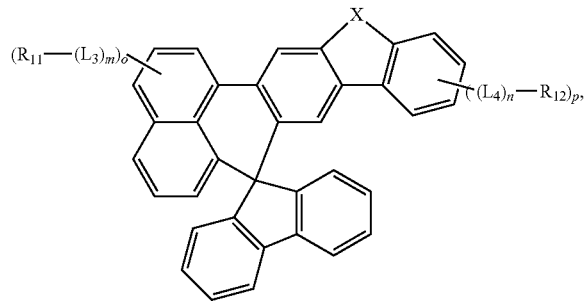

wherein each of $R_{11}$ and $R_{12}$ is independently selected from the group consisting of a $C_6$-$C_{30}$ aryl group unsubstituted or substituted with a $C_4$-$C_{30}$ aromatic or heteroaromatic group and a $C_4$-$C_{30}$ heteroaryl group unsubstituted or substituted with a $C_4$-$C_{30}$ aromatic or heteroaromatic group, wherein $R_{12}$ is selected from the group consisting of a $C_6$-$C_{30}$ aryl group unsubstituted or substituted with a $C_4$-$C_{30}$ aromatic or heteroaromatic group, an imidazolyl group unsubstituted or substituted with a $C_4$-$C_{30}$ aromatic or heteroaromatic group and a thiazolyl group unsubstituted or substituted with a $C_4$-$C_{30}$ aromatic or heteroaromatic group when X is $NR_5$, and each of $L_3$ and $L_4$ is independently selected from the group consisting of a $C_6$-$C_{30}$ arylene group unsubstituted or substituted with a $C_4$-$C_{30}$ aromatic or heteroaromatic group and a $C_4$-$C_{30}$ heteroarylene group unsubstituted or substituted with $C_4$-$C_{30}$ aromatic or heteroaromatic group, wherein $L_4$ is a $C_6$-$C_{30}$ arylene group unsubstituted or substituted with a $C_4$-$C_{30}$ aromatic or heteroaromatic group when X is $NR_5$, wherein each of o and p is independently 0 (zero) or 1, and at least one of o and p is 1, and wherein each of m, n and X is identical as defined in Chemical Formula 1.

3. The organic compound of claim 1, wherein the organic compound has the following structure of Chemical Formula 3:

Chemical Formula 3

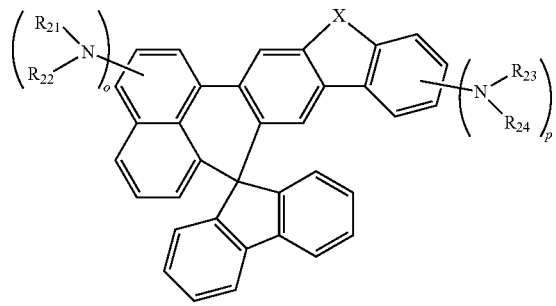

wherein each of $R_{21}$ to $R_{24}$ is independently selected from the group consisting of a $C_6$-$C_{30}$ aryl group unsubstituted or substituted with a $C_4$-$C_{30}$ aromatic or heteroaromatic group and a $C_4$-$C_{30}$ heteroaryl group unsubstituted or substituted with a $C_4$-$C_{30}$ aromatic or heteroaromatic group, and o is 1 and p is 0 (zero) or 1, and wherein at least one of o and p is 1, and X is identical as defined in Chemical Formula 1.

4. The organic compound of claim 1, wherein the organic compound has one of the following structures of Chemical Formula 4:
Chemical Formula 4
Compound 1
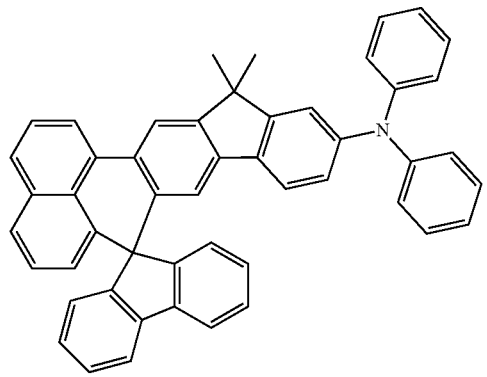
compound 2
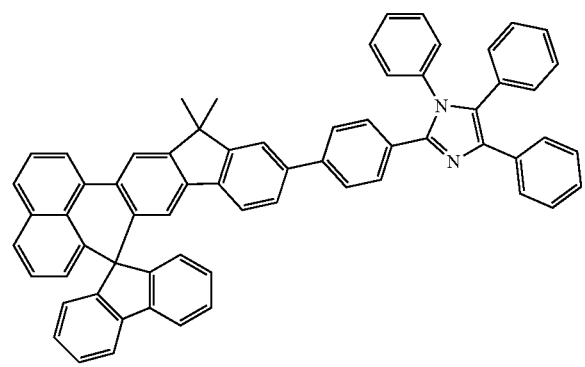
compound 3
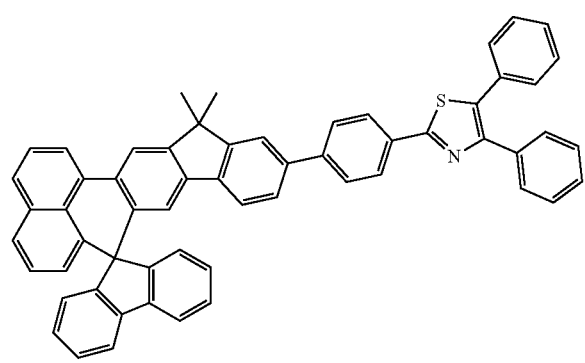
compound 4
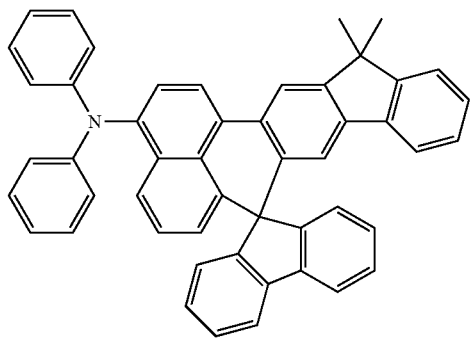
compound 5
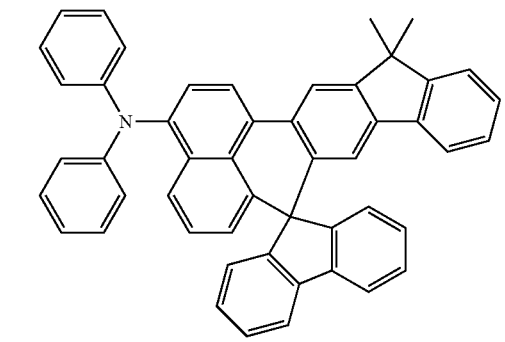
compound 6
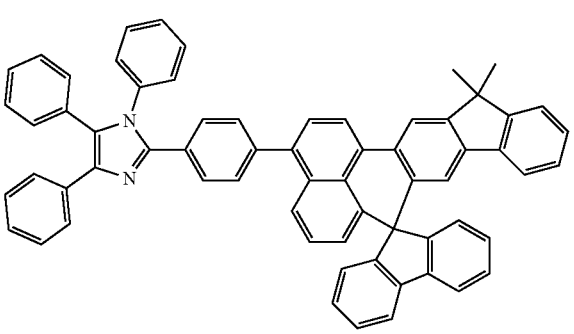
compound 8
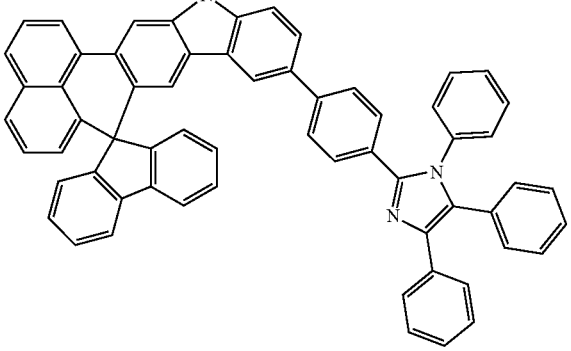

compound 9
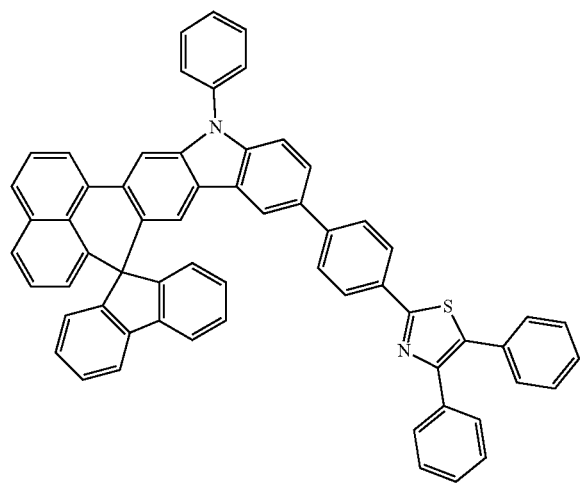
compound 10
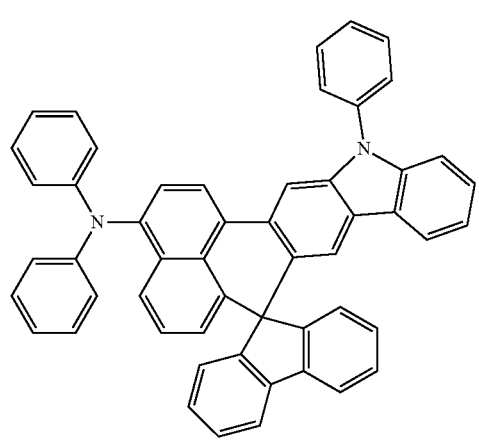
compound 11
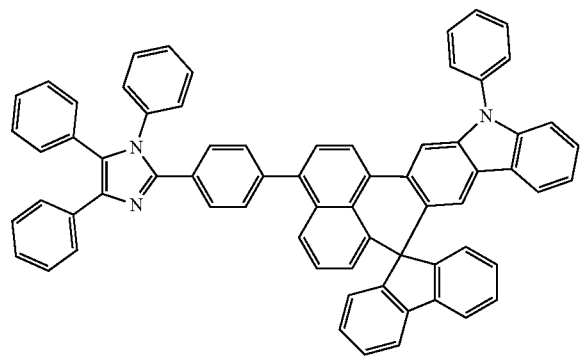
compound 12
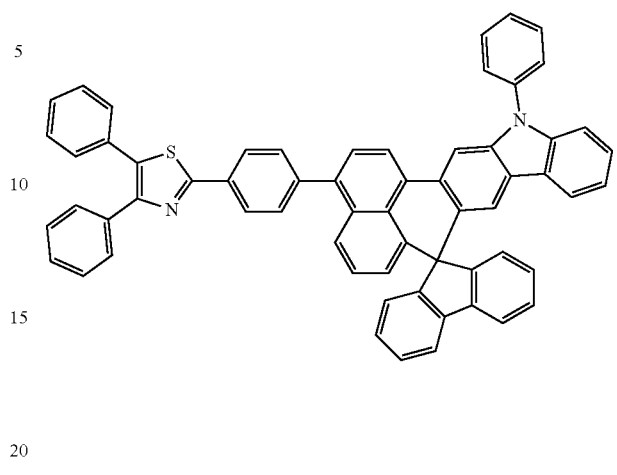
compound 13
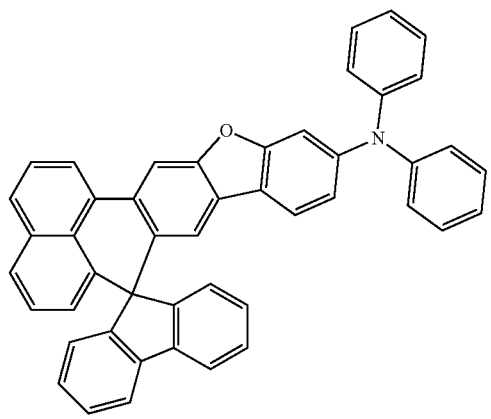
compound 14
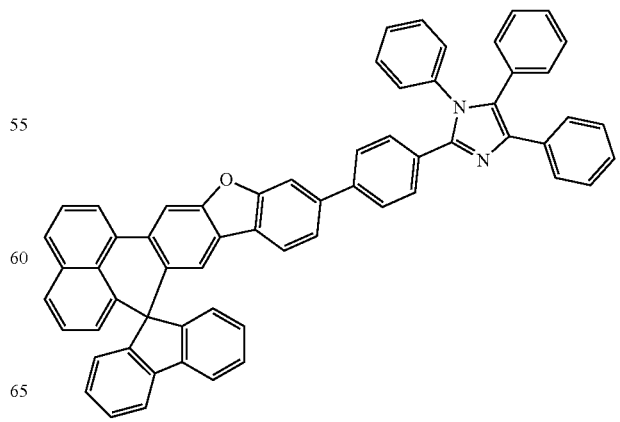

-continued
compound 15
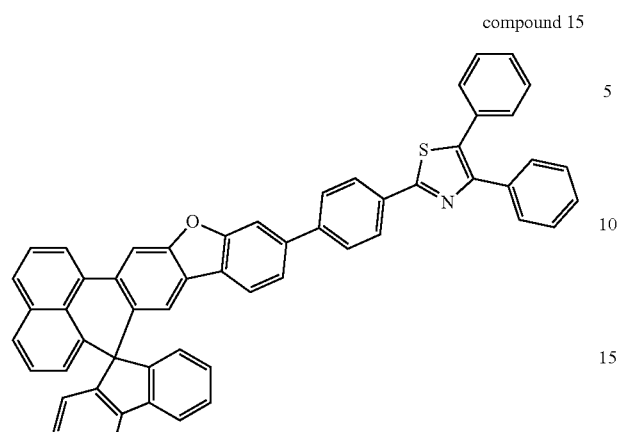
compound 16
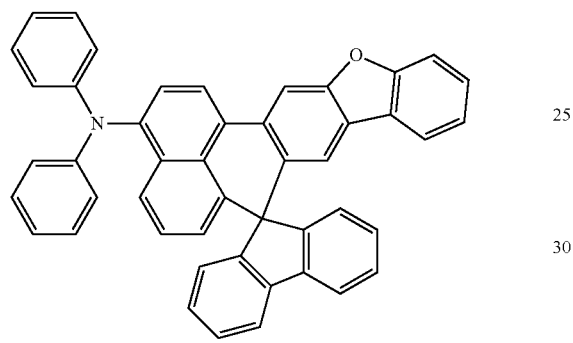
compound 17
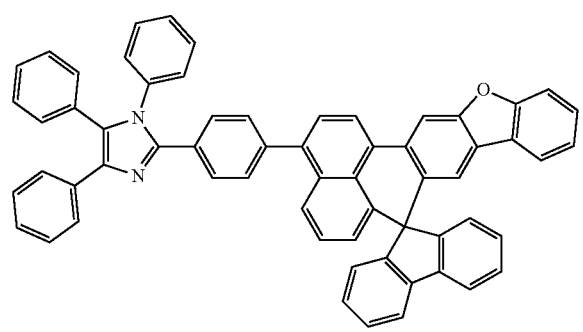
compound 18
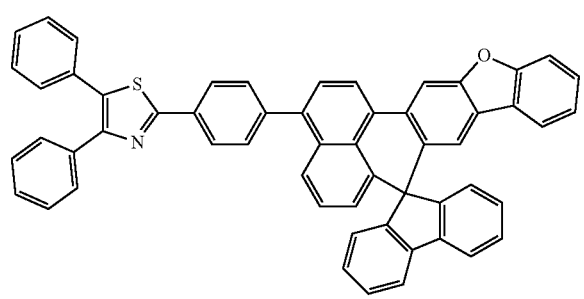
-continued
compound 19
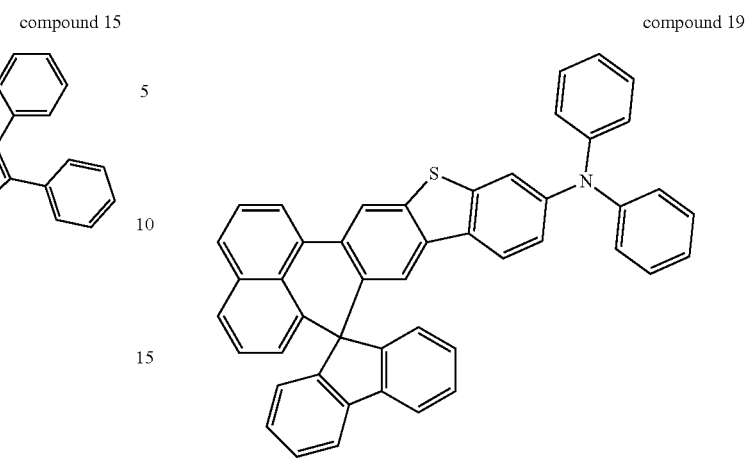
compound 20
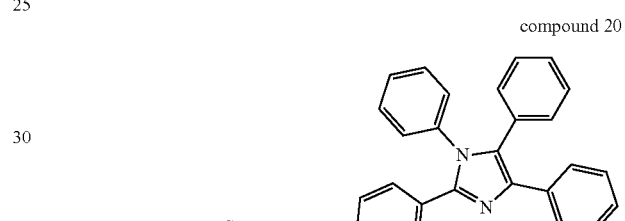
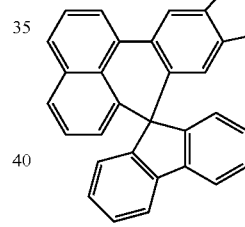
compound 21
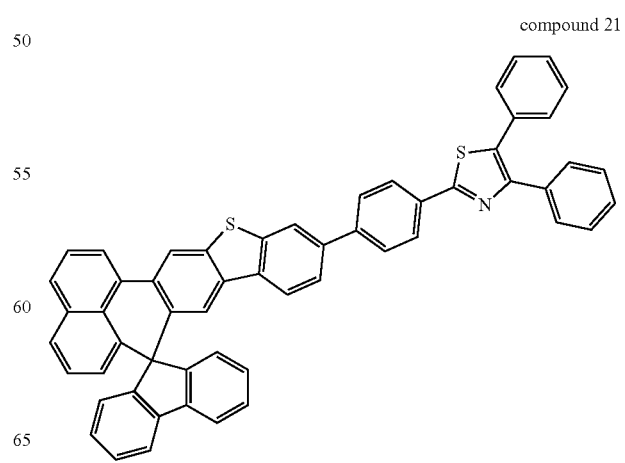

compound 22
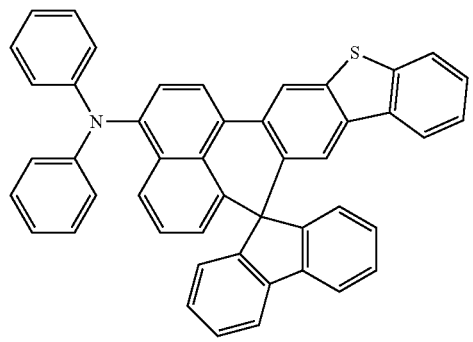
compound 23
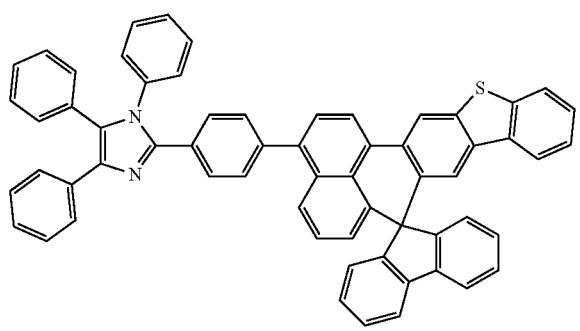
compound 24
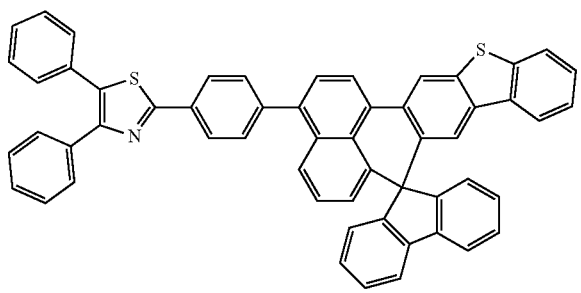
compound 25
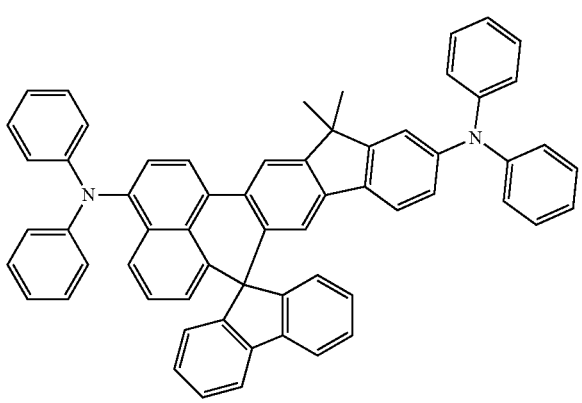
compound 26
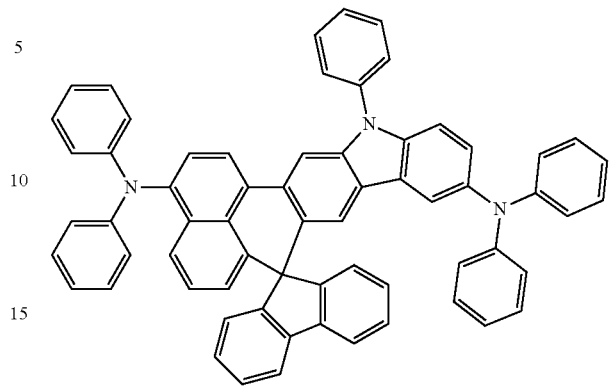
compound 27
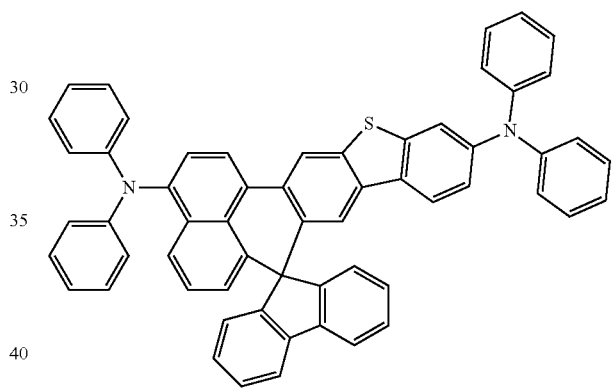
compound 28
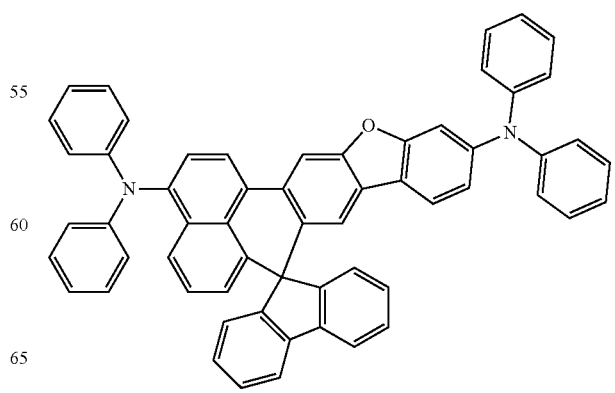

compound 29
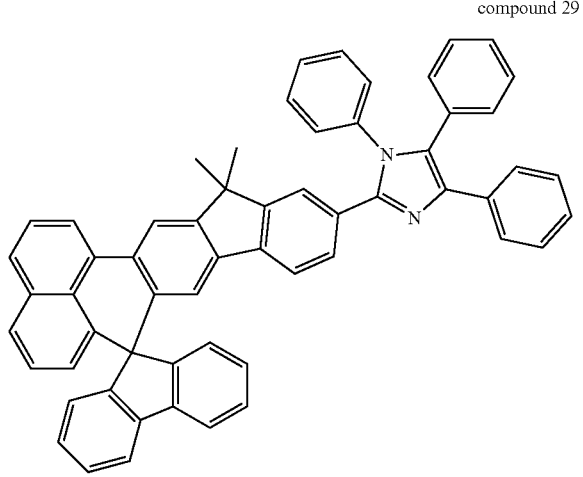
compound 30
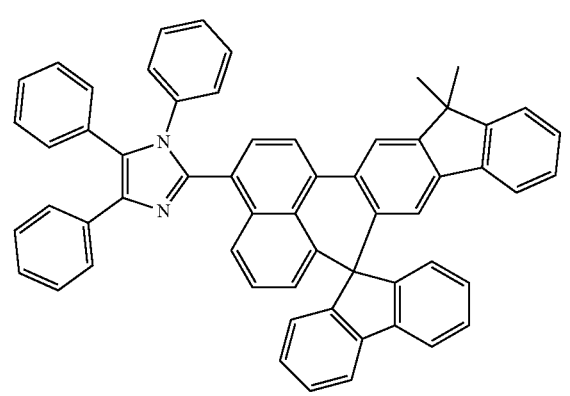
compound 31
compound 32
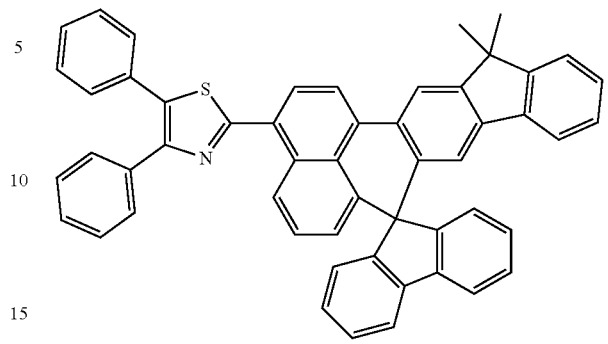
compound 33
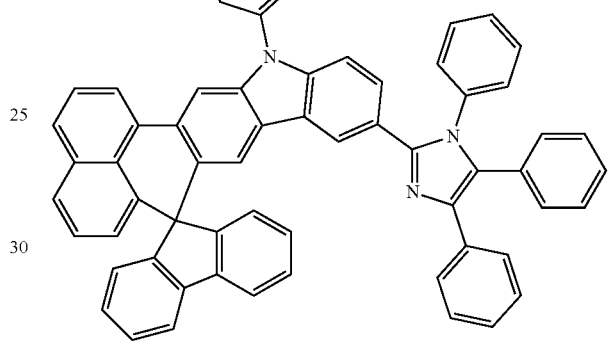
compound 34
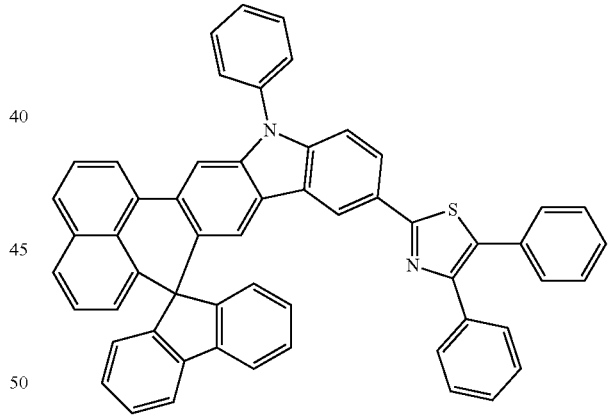
compound 35
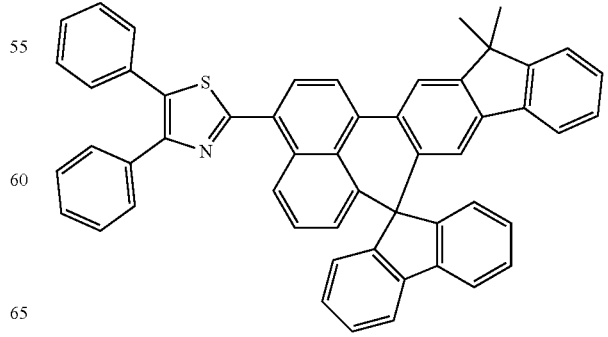

compound 36
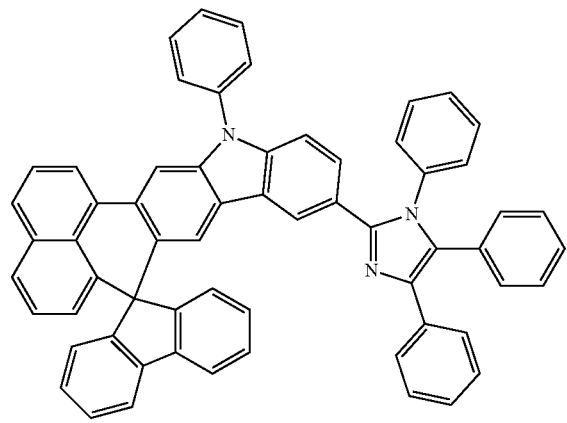
compound 37
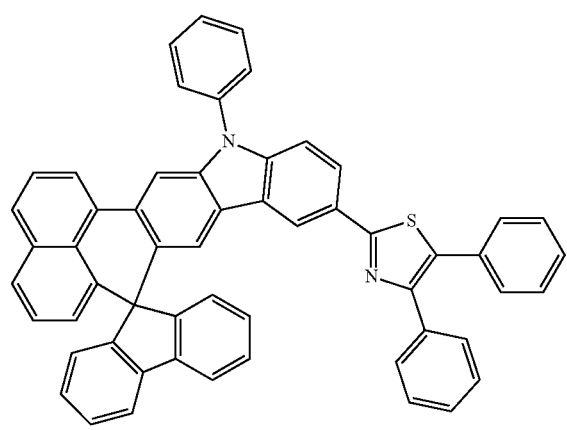
compound 38
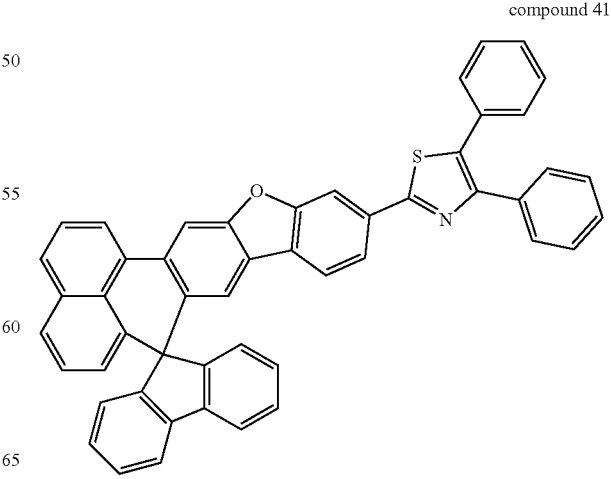
compound 39
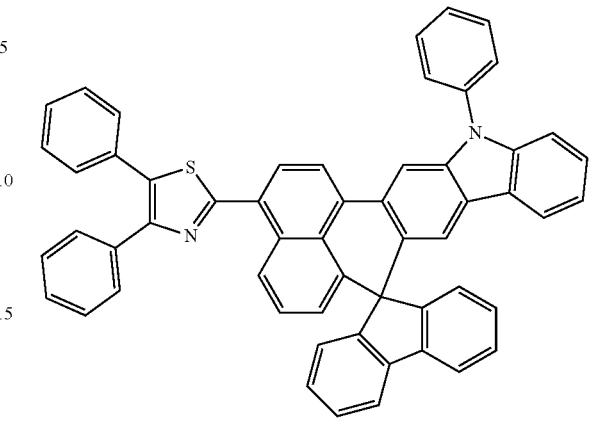
compound 40
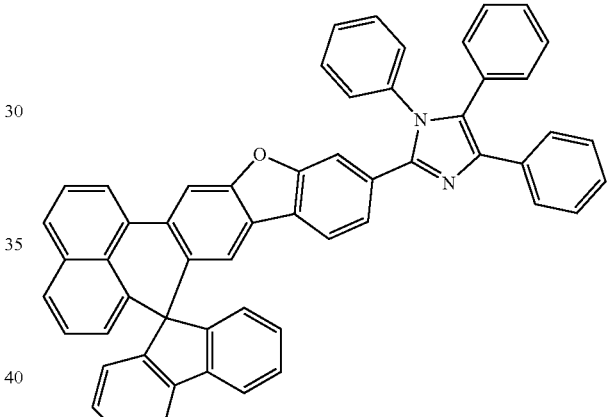
compound 41

-continued compound 42

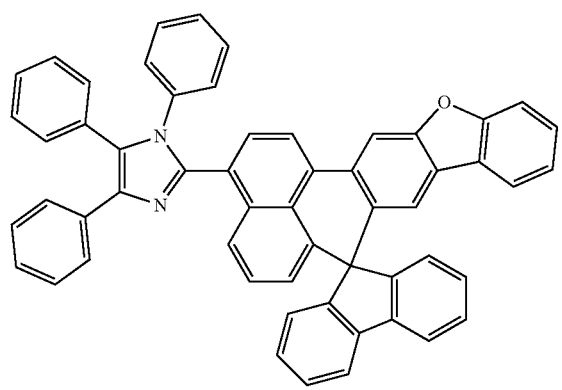

compound 43

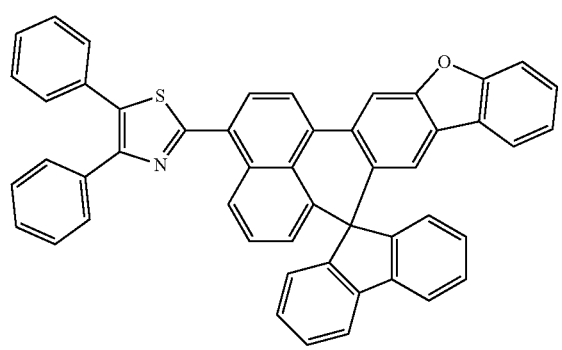

compound 44

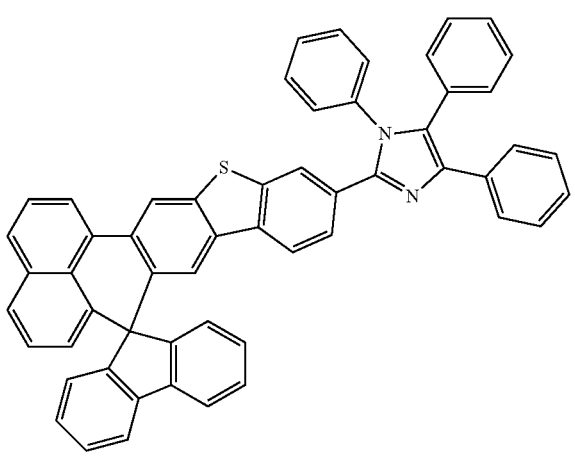

-continued compound 45

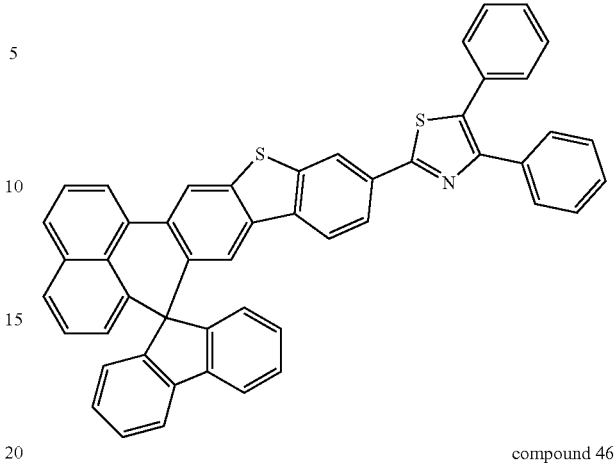

compound 46 compound 47

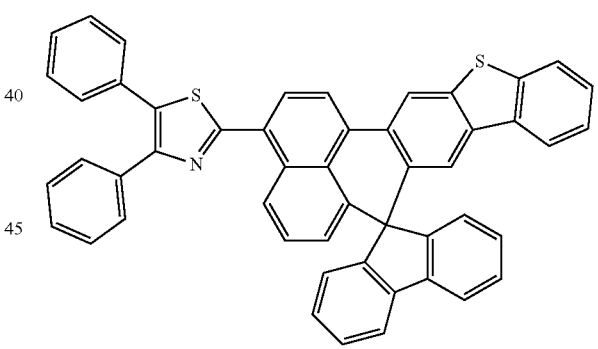

5. An organic light-emitting diode, comprising:
a first electrode;
a second electrode facing the first electrode; and
a first emitting material layer between the first and second electrode,
wherein the first emitting material layer includes an organic compound according to claim 1.

6. The organic light-emitting diode of claim 5, wherein the first emitting material layer further includes a first host, wherein the organic compound is used as a first fluorescent dopant.

7. The organic light-emitting diode of claim 5, wherein the first emitting material layer further includes a first host and a first dopant, wherein the organic compound is used as a second dopant.

8. The organic light-emitting diode of claim 7, wherein an excited state singlet energy level of the first dopant is higher than an excited state singlet energy level of the second dopant.

9. The organic light-emitting diode of claim 7, wherein an energy bandgap between an excited state singlet energy level of the first dopant and an excited state triplet energy level of the first dopant is equal to or less than about 0.3 eV.

10. The organic light-emitting diode of claim 7, an energy bandgap between a Highest Occupied Molecular Orbital energy level of the first host and a Highest Occupied Molecular Orbital energy level of the first dopant or an energy bandgap between a Lowest Unoccupied Molecular Orbital energy level of the first host and a Lowest Unoccupied Molecular Orbital energy level of the first dopant is equal to or less than about 0.5 eV.

11. The organic light-emitting diode of claim 7, wherein an excited state triplet energy level of the first dopant is lower than an excited state triplet energy level of the first host and higher than an excited state triplet energy level of the second dopant.

12. The organic light-emitting diode of claim 6, further comprising: a second emitting material layer between the first electrode and the first emitting material layer or between the first emitting material layer and the second electrode, wherein the second emitting material layer includes a second host and a delayed fluorescent dopant.

13. The organic light-emitting diode of claim 12, wherein the second emitting material layer is disposed between the first emitting material layer and the second electrode, and further comprising an electron blocking layer between the first electrode and the first emitting material layer.

14. The organic light-emitting diode of claim 13, wherein the first host is the same material as the electron blocking layer.

15. The organic light-emitting material of claim 12, wherein the second emitting material layer is disposed between the first electrode and the first emitting material layer, and further comprising a hole blocking layer between the first emitting material layer and the second electrode.

16. The organic light-emitting diode of claim 15, wherein the first host is the same material as the hole blocking layer.

17. The organic light-emitting diode of claim 12, wherein an excited state singlet energy level of the delayed fluorescent dopant is higher than an excited state singlet energy level of the first fluorescent dopant.

18. The organic light-emitting diode of claim 12, wherein an excited state singlet energy level of the first host is higher than an excited state singlet energy level of the first fluorescent dopant, and each of an excited state singlet energy level and an excited state triplet energy level of the second host is respectively higher than an excited state singlet energy level and an excited state triplet energy level of the delayed fluorescent dopant.

19. The organic light-emitting diode of claim 12, further comprising a third emitting material layer disposed oppositely to the first emitting material layer with respect to the second emitting material layer, wherein the third emitting material layer includes a third host and a second fluorescent dopant.

20. The organic light-emitting diode of claim 19, wherein the second emitting material layer is disposed between the first emitting material layer and the second electrode, and the third emitting material layer is disposed between the second emitting material layer and the second electrode, and further comprising an electron blocking layer between the first electrode and the first emitting material layer.

21. The organic light-emitting diode of claim 20, wherein the first host is the same material as the electron blocking layer.

22. The organic light-emitting diode of claim 19, wherein the second emitting material layer is disposed between the first emitting material layer and the second electrode, and the third emitting material layer is disposed between the second emitting material layer and the second electrode, and further comprising a hole blocking layer between the third emitting material layer and the second electrode.

23. The organic light-emitting diode of claim 20, wherein the third host is the same material as the hole blocking layer.

24. The organic light-emitting diode of claim 19, wherein an excited state singlet energy level of the delayed fluorescent dopant is higher than an excited state singlet energy level of the first fluorescent dopant and an excited state singlet energy level of the second fluorescent dopant.

25. The organic light-emitting diode of claim 19, wherein an excited state singlet energy level of the first host is higher than an excited state singlet energy level of the first fluorescent dopant, wherein each of an excited state singlet energy level and an excited state triplet energy level of the second host is respectively higher than an excited state singlet energy level and an excited state triplet energy level of the delayed fluorescent dopant, and wherein an excited state singlet energy level of the third host is higher than an excited state singlet energy level of the second fluorescent dopant.

26. An organic light-emitting device, comprising:
a substrate; and
an organic light-emitting diode according to claim 5 over the substrate.

27. An organic compound represented by the following Chemical Formula 1:

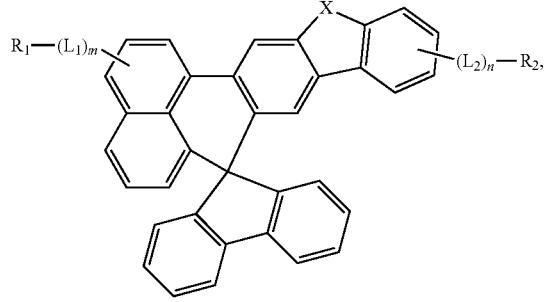

Chemical Formula 1 wherein each of $R_1$ and $R_2$ is independently selected from the group consisting of hydrogen, deuterium, tritium, amino group unsubstituted or substituted with a $C_4$-$C_{30}$ aromatic or heteroaromatic group, a $C_6$-$C_{30}$ aryl group unsubstituted or substituted with a $C_4$-$C_{30}$ aromatic or heteroaromatic group, a $C_4$-$C_{30}$ heteroaryl group unsubstituted or substituted with a $C_4$-$C_{30}$ aromatic or heteroaromatic group, a $C_6$-$C_{30}$ aralkyl group unsubstituted or substituted with a $C_4$-$C_{30}$ aromatic or heteroaromatic group, a $C_4$-$C_{30}$ heteroaralkyl group unsubstituted or substituted with a $C_4$-$C_{30}$ aromatic or heteroaromatic group, a $C_6$-$C_{30}$ aryloxyl group unsubstituted or substituted with a $C_4$-$C_{30}$ aromatic or heteroaromatic group and a $C_4$-$C_{30}$ heteroaryloxyl group unsubstituted or substituted with a $C_4$-$C_{30}$ aromatic or heteroaromatic group, and at least one of $R_1$ and $R_2$ is not hydrogen, deuterium and tritium, wherein each of $L_1$ and $L_2$ is independently selected from the group consisting of a $C_6$-$C_{30}$ arylene group unsubstituted or substituted with a $C_4$-$C_{30}$ aromatic or heteroaromatic group, a $C_4$-$C_{30}$ heteroarylene group unsubstituted or substituted with a $C_4$-$C_{30}$ aromatic or heteroaromatic group, a $C_6$-$C_{30}$ aralkylene group unsubstituted or substituted with a $C_4$-$C_{30}$ aromatic or heteroaromatic group, a $C_4$-$C_{30}$ heteroaralkylene group unsubstituted or substituted with a $C_4$-$C_{30}$ aromatic or heteroaromatic group, a $C_6$-$C_{30}$ aryloxylene group unsubstituted or substituted with a $C_4$-$C_{30}$ aromatic or heteroaromatic group and a $C_4$-$C_{30}$ heteroaryloxylene group unsubstituted or substituted with a $C_4$-$C_{30}$ aromatic or heteroaromatic group, and each of m and n is independently 0 (zero) or 1, and wherein X is $CR_3R_4$, O or S, and each of $R_3$ to $R_4$ is independently selected from the group consisting of hydrogen, a linear or branched $C_1$-$C_{20}$ alkyl group, a $C_6$-$C_{30}$ aryl group unsubstituted or substituted with a $C_4$-$C_{30}$ aromatic or heteroaromatic group, a $C_4$-$C_{30}$ heteroaryl group unsubstituted or substituted with a $C_4$-$C_{30}$ aromatic or heteroaromatic group, a $C_6$-$C_{30}$ aralkyl group unsubstituted or substituted with a $C_4$-$C_{30}$ aromatic or heteroaromatic group, a $C_4$-$C_{30}$ heteroaralkyl group unsubstituted or substituted with a $C_4$-$C_{30}$ aromatic or heteroaromatic group, a $C_6$-$C_{30}$ aryloxyl group unsubstituted or substituted with a $C_4$-$C_{30}$ aromatic or heteroaromatic group, a $C_4$-$C_{30}$ heteroaryloxyl group unsubstituted or substituted with a $C_4$-$C_{30}$ aromatic or heteroaromatic group, a $C_6$-$C_{30}$ arylamino group unsubstituted or substituted with a $C_4$-$C_{30}$ aromatic or heteroaromatic group and a $C_4$-$C_{30}$ heteroaryl amino group unsubstituted or substituted with a $C_4$-$C_{30}$ aromatic or heteroaromatic group.

28. The organic compound of claim 27, wherein the organic compound has the following structure of Chemical Formula 2:

Chemical Formula 2

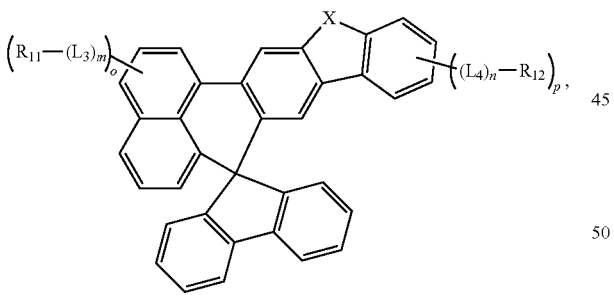

wherein each of $R_{11}$ and $R_{12}$ is independently selected from the group consisting of a $C_6$-$C_{30}$ aryl group unsubstituted or substituted with a $C_4$-$C_{30}$ aromatic or heteroaromatic group and a $C_4$-$C_{30}$ heteroaryl group unsubstituted or substituted with a $C_4$-$C_{30}$ aromatic or heteroaromatic group, and each of $L_3$ and $L_4$ is independently selected from the group consisting of a $C_6$-$C_{30}$ arylene group unsubstituted or substituted with a $C_4$-$C_{30}$ aromatic or heteroaromatic group and a $C_4$-$C_{30}$ heteroarylene group unsubstituted or substituted with $C_4$-$C_{30}$ aromatic or heteroaromatic group, wherein each of o and p is independently 0 (zero) or 1, and at least one of o and p is 1, and wherein each of m, n and X is identical as defined in Chemical Formula 1.

29. The organic compound of claim 27, wherein the organic compound has the following structure of Chemical Formula 3:

Chemical Formula 3

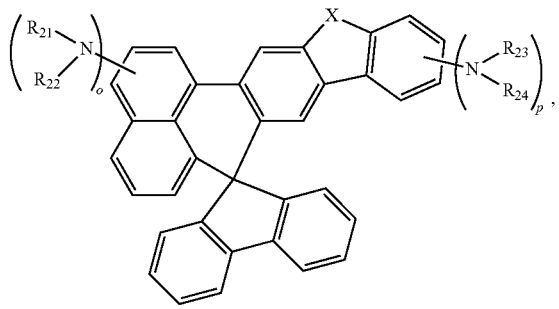

wherein each of $R_{21}$ to $R_{24}$ is independently selected from the group consisting of a $C_6$-$C_{30}$ aryl group unsubstituted or substituted with a $C_4$-$C_{30}$ aromatic or heteroaromatic group and a $C_4$-$C_{30}$ heteroaryl group unsubstituted or substituted with a $C_4$-$C_{30}$ aromatic or heteroaromatic group, and o is 1 and p is 0 (zero) or 1, and wherein at least one of o and p is 1, and X is identical as defined in Chemical Formula 1.

* * * * *